US010357537B2

(12) United States Patent
Gruber et al.

(10) Patent No.: US 10,357,537 B2
(45) Date of Patent: Jul. 23, 2019

(54) CYCLOTIDES AS IMMUNOSUPPRESSIVE AGENTS

(71) Applicants: Medizinische Universitat Wien, Vienna (AT); Universitatsklinikum Freiburg, Freiburg (DE)

(72) Inventors: Christian Werner Gruber, Klosterneuburg (AT); Carsten Gruendemann, Freiburg (DE)

(73) Assignees: Medizinische Universitat Wien, Wien (AT); Universitatsklinikum Freiburg, Freiburg (DE)

( * ) Notice: Subject to any disclaimer, the term of this patent is extended or adjusted under 35 U.S.C. 154(b) by 0 days.

(21) Appl. No.: 16/174,428

(22) Filed: Oct. 30, 2018

(65) Prior Publication Data

US 2019/0046607 A1 Feb. 14, 2019

Related U.S. Application Data

(60) Division of application No. 15/244,244, filed on Aug. 23, 2016, now Pat. No. 10,159,710, which is a continuation of application No. 14/366,427, filed as application No. PCT/EP2012/076739 on Dec. 21, 2012, now Pat. No. 9,453,052.

(30) Foreign Application Priority Data

Dec. 22, 2011 (EP) ..................... 11195413
Dec. 13, 2012 (EP) ..................... 12196918

(51) Int. Cl.
A61K 39/00 (2006.01)
A61K 38/16 (2006.01)
A61K 38/12 (2006.01)
C07K 14/415 (2006.01)
A61K 45/06 (2006.01)
A61K 51/08 (2006.01)
C07K 14/00 (2006.01)
G01N 33/50 (2006.01)
A61P 37/06 (2006.01)

(52) U.S. Cl.
CPC ............ A61K 38/168 (2013.01); A61K 38/12 (2013.01); A61K 38/16 (2013.01); A61K 45/06 (2013.01); A61K 51/08 (2013.01); A61P 37/06 (2018.01); C07K 14/00 (2013.01); C07K 14/415 (2013.01); G01N 33/5023 (2013.01)

(58) Field of Classification Search
None
See application file for complete search history.

(56) References Cited

U.S. PATENT DOCUMENTS 4,711,955 A 12/1987 Ward et al.
4,880,635 A 11/1989 Janoff et al.
5,525,711 A 6/1996 Hawkins et al.
5,792,608 A 8/1998 Swaminathan et al.
7,592,533 B1 9/2009 Lee
2008/0194543 A1 8/2008 Chou
2010/0298528 A1* 11/2010 Craik .................... C07K 14/001
530/321
2011/0143996 A1 6/2011 Yount et al.

FOREIGN PATENT DOCUMENTS

EP 0302175 A2 8/1989
WO WO 2011/005598 A1 1/2001
WO WO 2006/032436 A2 3/2006
WO WO 2007/149052 12/2007

OTHER PUBLICATIONS

Abraham, "Mammalian target of rapamycin: immunosuppressive drugs uncover a novel pathway of cytokine receptor signaling," 1998, Curr Opin Immunol, 10(3):330-336.
Albouz-Abo et al., "A conformational study of the human and rat encephalitogenic myelin oligodendrocyte glycoprotein peptides 35-55" 1997 Eur J Biochem, 246:59-70.
Ayers et al., "Early glial responses in murine models of multiple sclerosis," 2004 Neurochem Int, 45(2-3):409-419.
Barbeta et al., "Plant cyclotides disrupt epithelial cells in the midgut of lepidopteran larvae," Jan. 2008 Proc Natl Acad Sci USA, 105(4):1221-1225.
Barry et al., "Linearization of a Naturally Occurring Circular Protein Maintains Structure but Eliminates Hemolytic Activity," 2003 Biochemistry, 42(22):6688-6695.
Bernard et al., "Do antibodies to myelin basic protein isolated from multiple sclerosis cross-react with measles and other common virus antigens?" 1983 Clin Exp Immunol, 52(1): 98-106.

(Continued)

Primary Examiner — Jeanette M Lieb
(74) Attorney, Agent, or Firm — Mueting, Raasch & Gebhardt, P.A.

(57) ABSTRACT

The present invention relates to a pharmaceutical composition comprising a cyclotide for use in immune suppression as well as to a method for immune suppression comprising the step of administering an effective amount of a pharmaceutical composition comprising such a cyclotide to a subject in need thereof. The present invention also relates to a pharmaceutical composition comprising a cyclotide for use in treating or preventing a disorder selected from the group consisting of (i) an autoimmune disorder; (ii) a hypersensitivity disorder; and (iii) a lymphocyte-mediated inflammation. Likewise, the present invention also relates to a method for treating or preventing a disorder selected from the group consisting of (i) an autoimmune disorder; (ii) a hypersensitivity disorder; and (iii) a lymphocyte-mediated inflammation. The present invention further relates to a method of screening for and/or selecting an immunosuppressive cyclotide or a mutation which results in a mutated cyclotide having an induced or enhanced immunosuppressive activity. The present invention further relates to a method of producing an immunosuppressive cyclotide or an immunosuppressive pharmaceutical composition. The present invention further relates to a mutated cyclotide having immunosuppressive activity and a pharmaceutical composition comprising the same.

Figure 1:
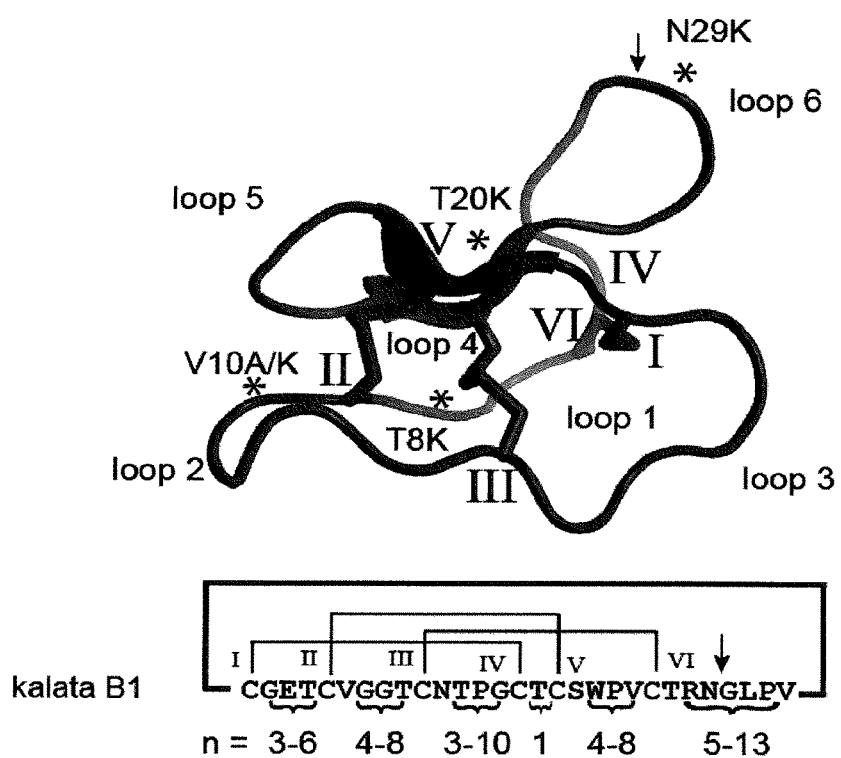

20 Claims, 36 Drawing Sheets
Specification includes a Sequence Listing.

(56) References Cited

OTHER PUBLICATIONS

Bernard et al., "Multiple sclerosis: an autoimmune disease of multifactorial etiology," 1992 *Curr Opin Immunol*, 4(6):760-765.
Bernard et al., "Myelin oligodendrocyte glycoprotein: a novel candidate autoantigen in multiple sclerosis," 1997 *J Mol Med*, 75(2):77-88.
Bettadapura et al., "Expression, Purification, and Encephalitogenicity of Recombinant Human Myelin Oligodendrocyte Glycoprotein," 1998 *J Neurochem*,70(4):1593-1599.
Betts et al., "Sensitive and viable identification of antigen-specific CD8+ T cells by a flow cytometric assay for degranulation," 2003 *J Immunol Methods*, 281:65-78.
Burman et al., "Evaluation of Toxicity and Antitumor Activity of Cycloviolacin O2 in Mice," 2010 *Biopolymers Pept Sci*, 94:626-34.
Callan et al., "CD8(+) T-cell selection, function, and death in the primary immune response in vivo," Nov. 2000 *J Clin Invest*, 106(10), 1251-1261.
Čemažar et al., "Factors Influencing the Stability of Cyclotides: Proteins with a circular Backbone and Cystine Knot Motif," Sep. 2006 *Internat J Peptide Research and Therapeutics*, 12(3):253-260.
Čemažar et al., "Knots in Rings. The circular knotted protein Momordica cochinchinensis trypsin inhibitor-II folds via a stable two-disulfide intermediate," Mar. 2006 *J Biol Chem*, 281(12), 8224-8232.
Čemažar et al., "Sequential Overlapping Fractionation (SOFT) approach to Molecular Grafting yields Novel Cyclic Peptides for the Treatment of Multiple Sclerosis," 20th American-Peptide-Society Symposium; Montreal, Canada, Jun. 26-30, 2007, *Biopolymers* 88(4), SI:523.
Cerdan et al., "CD28 costimulation regulates long-term expression of the three genes (alpha, beta, gamma) encoding the high-affinity IL2 receptor," 1995 *Res Immunol*, 146(3):164-168.
Chen et al., "Isolation and Characterization of Novel Cyclotides from *Viola hederaceae*: Solution Structure and Anti-Hiv Activity of vhl-1, a Leaf-Specific Expressed Cyclotide," Jun. 2005 *J Biol Chem*, 280(23):22395-22405.
Clark et al., "Structural plasticity of the cyclic-cystine-knot framework: implications for biological activity and drug design," 2006 *Biochem J*, 394:85-93.
Clark et al., "The Engineering of an Orally Active Conotoxin for the Treatment of Neuropathic Pain" 2010, *Angew Chem Int Ed*, 49(51), 6545-6548.
Clark et al., "Native Chemical Ligation Applied to the Synthesis and Bioengineering of Circular Peptides and Proteins," 2010 *Biopolymers (Pept Sci)*, 94(4):414-422.
Cole-Strauss et al., "Correction of the Mutation Responsible for Sickle Cell Anemia by an RNA-DNA Oligonucleotide," 1996 *Science*, 273(5280):1386-9.
Colgrave et al., "Thermal, Chemical, and Enzymatic Stability of the Cyclotide Kalata B1: The Importance of the Cyclic Cystine Knot," 2004 *Biochemistry*, 43(20):5965-5975.
Colgrave et al., "Peptide quantification by matrix-assisted laser desorption ionisation time-of-flight mass spectrometry: investigations of the cyclotide kalata B1 in biological fluids," 2005 *J Chromatogr A*, 1091:187-193.
Colgrave et al., "Cyclotides: Natural, Circular Plant Peptides that Possess Significant Activity Against Gastrointestinal Nematode Parasites of Sheep," 2008 *Biochemistry*, 47(20):5581-5589.
Colgrave et al., "Anthelmintic activity of cyclotides: In vitro studies with canine and human hookworms," 2009 *Acta Trop*, 109(2):163-166.
Colgrave et al., "A New "Era" for Cyclotide Sequencing," 2010 *Biopolymers (Pept Sci)*, 94(5):592-601.
Craik et al., "Plant Cyclotides: A Unique Family of Cyclic and Knotted Proteins that Defines the Cyclic Cystine Knot Structural Motif," 1999 *J Mol Biol*, 294(5):1327-1336.
Craik, "Plant cyclotides: circular, knotted peptide toxins," 2001 *Toxicon*, 39(12):1809-1813.
Craik et al., "The cystine knot motif in toxins and implications for drug design," 2001 *Toxicon*, 39(1):43-60.

Craik, "Chemistry. Seamless Proteins Tie Up Their Loose Ends," Mar. 2006 *Science*, 311:1563-1564.
Craik et al., "The Cyclotide Family of Circular Miniproteins: Nature's Combinatorial Peptide Template," 2006 *Biopolymers*, 84(3):250-266.
Craik et al., "The chemistry and biology of cyclotides," 2007 *Curr Opin Drug Discov Devel*, 10(2):176-184.
Craik et al., "Cyclotides: macrocyclic peptides with applications in drug design and agriculture," 2010 *Cell. Mol. Life Sci*, 67:9-16.
Daly et al., "Chemical Synthesis and Folding Pathways of Large Cyclic Polypeptides: Studies of the Cystine Knot Polypeptide Kalata B1," 1999 *Biochemistry*, 38(32):10606-10614.
Daly et al., "The role of the cyclic peptide backbone in the anti-HIV activity of the cyclotide kalata B1," 2004 *FEBS Lett*, 574(1-3):69-72.
Dawson et al., "Synthesis of Proteins by Native Chemical Ligation," 1994 *Science*, 266:776-779.
De Mattos et al., "Nephrotoxicity of immunosuppressive drugs: long-term consequences and challenges for the future," Feb. 2000 *Am J Kidney Dis*, 35(2):333-346.
DeVries et al., "On the edge: the physiological and pathophysiological role of chemokines during inflammatory and immunological responses," 1999 *Semin Immunol*, 11:95-104.
Dos Santos et al., "CCL2 and CCL5 mediate leukocyte adhesion in experimental autoimmune encephalomyelitis—an intravital microscopy study," 2005 *J Neuroimmunol*, 162:122-129.
Dubois et al., "Interferon beta in multiple sclerosis: experience in a British specialist multiple sclerosis centre," 2003 *J Neurol Neurosurg Psychiatry*,74:946-949.
Ewing et al., "Insights into the aetiology and pathogenesis of multiple sclerosis," 1998 *Immunol Cell Biol*, 76:47-54.
Gerlach et al., "Anticancer and Chemosensitizing Abilities of Cycloviolacin 02 From Viola Odorata and Psyle Cyclotides from Psychotria Leptothyrsa," 2010 *Biopolymers*, 94:617-25.
Gillon et al., "Biosynthesis of circular proteins in plants," 2008 *Plant J*, 53:505-515.
Gonzalo, "Cutting edge: the related molecules CD28 and inducible costimulator deliver both unique and complementary signals required for optimal T cell activation," 2001 *J Immunol*, 166:1-5.
Göransson et al., "Reversible Antifouling Effect of the Cyclotide Cycloviolacin O2 Against Barnacles," 2004 *J Nat Prod*, 67:1287-1290.
Gran, "An Oxytocic Principle Found in Oldenlandia Affinis DC," Dec. 1970 *Medd Nor Farm Selsk*, 12:173-180.
Gran, "On the Effect of a Polypeptide Isolated from "Kalata-Kalata" (*Oldenlandia affinis DC*) on the Oestrogen Dominated Uterus", 1973, *Acta pharmacol. et toxicol.*, 33:400-408.
Gruber et al., "A Novel Plant Protein-Disulfide Isomerase Involved in the Oxidative Folding of Cystine Knot Defense Proteins," Jul. 2007 *J Biol Chem*, 282(28):20435-20446.
Gruber et al., "Insecticidal plant cyclotides and related cystine knot toxins," 2007 *Toxicon*, 49: 561-575.
Gruber et al., "Distribution and Evolution of Circular Miniproteins in Flowering Plants," Sep. 2008 *Plant Cell*, 20:2471-2483.
Gruber et al., "Ligand-Based Peptide Design and Combinatorial Peptide Libraries to Target G Protein-Coupled Receptors," 2010 *Curr Pharm Des*, 16:3071-3088.
Gruber, "Global Cyclotide Adventure: A Journey Dedicated to the Discovery of Circular Peptides from Flowering Plants," 2010 *Biopolymers (Pepti Sci)*, 94(5):565-572.
Gruber et al., "Uterotonic Plants and their Bioactive Constituents," Feb. 2011 *Planta Med*, 77(3):207-220.
Grundemann et al., "An aqueous birch leaf extract of *Betula pendula* inhibits the growth and cell division of inflammatory lymphocytes." 2011 *J Ethnopharmacol*, 136(3):444-451.
Gründemann et al., "Do Plant Cyclotides Have Potential As Immunosuppressant Peptides?" 2012 *J Nat Prod* 75:167-174.
Gründemann et al., "Cyclotides Suppress Human T-Lymphocyte Proliferation by an Interleukin 2-Dependent Mechanism", 2013, *PLOS One* 8, 1-12.

(56) References Cited

OTHER PUBLICATIONS

Gunasekera et al., "Engineering Stabilized Vascular Endothelial Growth Factor-A Antagonists: Synthesis, Structural Characterization, and Bioactivity of Grafted Analogues of Cyclotides," 2008 *J Med Chem*, 51:7697-704.
Henriques et al., "Decoding the Membrane Activity of the Cyclotide Kalata B1: The Importance of Phosphatidylethanolamine Phospholipids and Lipid Organization on Hemolytic and Anti-HIV Activities," Jul. 2011 *J Biol Chem*, 286(27):24231-24241.
Henry et al., "Structure and evolution of the extended B7 family," 1999 *Immunol Today*, 20(6):285-288.
Herrmann et al., "The alpine violet, *Viola biflora*, is a rich source of cyclotides with potent cytotoxicity," *Phytochemistry*, Jan. 14, 2008; 69(4):939-952.
Horn et al., "Interleukin-6 Signal Transduction and Lymphocyte Function," 2000 *Immunobiology*, 202:151-167.
Huang, "Lysine-scanning mutagenesis reveals an amendable face of the cyclotide kalata B1 for the optimization of nematocidal activity," Apr. 2010 *J Biol Chem*, 285(14):10797-10805.
Hvas et al., "Perivascular T Cells Express the Pro-Inflammatory Chemokine Rantes Mrna in Multiple Sclerosis Lesions," 1997 *Scand J Immunol*, 46:195-203.
Ichikawa et al., "Antibody response in Lewis rats injected with myelin oligodendrocyte glycoprotein derived peptides," 1996 *Int Immunol*, 8(11):1667-1674.
Ichikawa et al., "Analysis of the fine B cell specificity during the chronic/relapsing course of a multiple sclerosis-like disease in Lewis rats injected with the encephalitogenic myelin oligodendrocyte glycoprotein peptide 35-55," 1996 *J Immunol*, 157:919-926.
Ichikawa et al., "IgG Subclass Switching is Associated with the Severity of Experimental Autoimmune Encephalomyelitis Induced with Myelin Oligodendrocyte Glycoprotein Peptide in NOD Mice," 1999 *Cell Immunol*, 191:97-104.
Ihle, "Cytokine receptor signalling," 1995 *Nature*, 377:591-594.
Ireland et al., "A novel suite of cyclotides from Viola odorata: sequence variation and the implications for structure, function and stability," 2006 *Biochem J*, 400:1-12.
Ireland et al., "Cyclotides as Natural Anti-HIV Agents," 2007 *Biopolymers (Pept Sci)*, 90(1):51-60.
Ireland et al., "Isolation, Sequencing, and Structure-Activity Relationships of Cyclotides," 2010 *J Nat Prod*, 73:1610-1622.
Jain et al., "Transcriptional regulation of the IL-2 gene," 1995 *Curr Opin Immunol*, 7:333-342.
Janeway et al., "Signals and Signs for Lymphocyte Responses," 1994 *Cell*, 76:275-285.
Jennings et al., "Biosynthesis and insecticidal properties of plant cyclotides: The cyclic knotted proteins from *Oldenlandia affinis*," Sep. 2001 *Proc Natl Acad Sci USA*, 98(19):10614-10619.
Johns et al., "Binding of complement component C1q to myelin oligodendrocyte glycoprotein: a novel mechanism for regulating CNS inflammation," 1997 *Mol Immunol*, 34(1):33-38.
Kimura et al., "Biosynthesis of the Cyclotide Kalata B1 by Using Protein Splicing," 2006 *Angew Chem Int Ed*, 45:973-976.
Kolmar, "Biological diversity and therapeutic potential of natural and engineered cystine knot miniproteins," 2009 *Curr Opin Pharmacol*, 9:608-614.
Krause et al., "Grafting of thrombopoietin-mimetic peptides into cystine knot miniproteins yields high-affinity thrombopoietin antagonists and agonists," 2007 *FEBS J*, 274:86-95.
Larsson et al., "Gram positive bacteria induce IL-6 and IL-8 production in human alveolar macrophages and epithelial cells," 1999 *Inflammation*, 23(3):217-230.
Lindholm et al., "Cyclotides: a Novel Type of Cytotoxic Agents," 2002 *Mol Cancer Ther*, 1:365-369.
Liu et al., "TNF is a potent anti-inflammatory cytokine in autoimmune-mediated demyelination," Jan. 1998, *Nat Med*, 4(1):78-83.
Luckett et al., "High-Resolution Structure of a Potent, Cyclic Proteinase Inhibitor from Sunflower Seeds," 1999 *J Mol Biol*, 290:525-533.
Martin et al., "Rational design of a CD4 mimic that inhibits HIV-1 entry and exposes cryptic neutralization epitopes," Jan. 2003 *Nat Biotechnol*, 21:71-76.
Martinez-Bueno et al., "Determination of the Gene Sequence and the Molecular Structure pf the Enterococcal Peptide Antibiotic AS-48," Oct. 1994 *J Bacteriol*, 176(20):6334-6339.
Matsuda et al., "Mechanisms of action of cyclosporine," 2000 *Immunopharmacology*, 47:119-125.
McQualter et al., "Granulocyte Macrophage Colony-Stimulating Factor: A New Putative Therapeutic Target in Multiple Sclerosis," Oct. 2001 *J Exp Med*, 194(7), 873-881.
Menon et al., "Demyelinating Antibodies to Myelin Oligodendrocyte Glycoprotein and Galactocerebroside Induce Degradation of Myelin Basic Protein in Isolated Human Myelin," 1997 *J Neurochem*, 69:214-222.
Minami et al., "The IL-2 Receptor Complex: Its Structure, Function, and Target Genes," 1993 *Annu. Rev. Immunol*, 11:245-268.
Mylne et al., "Albumins and their processing machinery are hijacked for cyclic peptides in sunflower," Mar. 2011 *Nat Chem Biol*, 7:257-259.
Nguyen et al., "Discovery and Characterization of Novel Cyclotides Originated from Chimeric Precursors Consisting of Albumin-1 Chain a and Cyclotide Domains in the Fabaceae Family," Jul. 2011 *J Biol Chem*, 286(27):24275-24287.
Nicholson et al., "Manipulation of the Th1/Th2 balance in autoimmune disease," 1996 *Curr Opin Immunol*, 8:837-842.
Ohta et al., "A2A Adenosine Receptor May Allow Expansion of T Cells Lacking Effector Functions in Extracellular Adenosine-Rich Microenvironments," 2009 *J Immunol*, 183:5487-5493.
Okuda et al., "The Development of Autoimmune Encephalomyelitis Provoked by Myelin Oligodendrocyte Glycoprotein is Associated with an Upregulation of Both Proinflammatory and Immunoregulatory Cytokines in the Central Nervous System," 1998 *J Interferon Cytokine Res*, 18:415-421.
Okuda et al., "The suppression of T cell apoptosis influences the severity of disease during the chronic phase but not the recovery from the acute phase of experimental autoimmune encephalomyelitis in mice," 2002 *J Neuroimmunol*, 131:115-125.
Onuki et al., "Axonal Degeneration is an Early Pathological Feature in Autoimmune-Mediated Demyelination in Mice," 2001 *Microsc Res Tech*, 52:731-739.
Orlinick et al., "TNF-related ligands and their receptors," 1998 *Cell Signal* 10(8):543-551.
Owens, "The enigma of multiple sclerosis: inflammation and neurodegeneration cause heterogeneous dysfunction and damage," 2003 *Curr Opin Neurol*, 16:259-265.
Pedersen et al., "Flow Microfluorometry Detects IgM Autoantibody to Oligodendrocytes in Multiple Sclerosis," 1983 *J Neuroimmunol*, 5:251-259.
Plan et al., "The Cyclotide Fingerprint in *Oldenlandia Affinis*: Elucidation of Chemically Modified, Linear and Novel Macrocyclic Peptides," 2007 *ChemBioChem*, 8:1001-1011.
Poth et al., "Discovery of an unusual biosynthetic origin for circular proteins in legumes," Jun. 2011 *Proc Nall Acad Sci USA*, 108(25):10127-10132.
Poth et al., "Discovery of cyclotides in the fabaceae plant family provides new insights into the cyclization, evolution, and distribution of circular proteins," 2011 *ACS Chem Biol*, 6:345-355.
Pratt et al., "Melittin-induced membrane permeability: a nonosmotic mechanism of cell death," 2005 *In Vitro Cell Dev Biol Anim*, 41(10):349-355.
Reiss et al., "Inhibition of platelet aggregation by grafting RGD and KGD sequences on the structural scaffold of small disulfide-rich proteins," 2006 *Platelets*, 17(3):153-157.
Romagnani, "Th1/Th2 Cells," 1999 *Inflamm Bowel Dis*, 5:285-294.
Romanic et al., "T Cell Adhesion to Endothelial Cells and Extracellular Matrix is Modulated Upon Transendothelial Cell Migration," 1997 *Lab Invest*, 76(1):11-23.
Rosengren et al., "Twists, Knots, and Rings in Proteins. Structural Definition of the Cyclotide Framework," Mar. 2003 *J Biol Chem*, 278(10):8606-8616.

(56) References Cited

OTHER PUBLICATIONS

Rosengren et al., "Microcin J25 Has a Threaded Sidechain-To-Backbone Ring Structure and Not a Head-To-Tail Cyclized Backbone," 2003 *J Am Chem Soc*, 125:12464-12474.

Saska et al., "An Asparaginyl Endopeptidase Mediates in Vivo Protein Backbone Cyclization," Oct. 2007 *J Biol Chem*, 282(40):29721-29728.

Schnölzer et al., "In situ neutralization in Boc-chemistry solid phase peptide synthesis. Rapid, high yield assembly of difficult sequences," 1992 *Int J Pept Protein Res*, 40:180-193.

Schreiber, "Chemistry and Biology of the Immunophilins and their Immunosuppressive Ligands," Jan. 1991 *Science*, 251:283-287.

Seydel et al., "Formation of cyclotides and variations in cyclotide expression in *Oldenlandia affinis* suspension cultures," 2007 *Appl. Microb. Biotechnol*, 77:275-284.

Simonsen et al., "A Continent of Plant Defense Peptide Diversity: Cyclotides in Australian *Hybanthus* (Violaceae)," Nov. 2005 *Plant Cell*, 17:3176-3189.

Simonsen et al., "Alanine Scanning Mutagenesis of the Prototypic Cyclotide Reveals a Cluster of Residues Essential for Bioactivity," Apr. 2008 *J Biol Chem*, 283(15):9805-9813.

Slavin et al., "Induction of a Multiple Sclerosis-Like Disease in Mice with an Immunodominant Epitope of Myelin Oligodendrocyte Glycoprotein," 1998 *Autoimmunity*, 28:109-120.

Smith et al., "Cyclotides: a patent review," *Expert Opinion on Therapeutic Patents*, Informa Healthcare; Nov. 1, 2011; 21(11):1657-1672.

Stein et al., "Arthritis & Rheumatism," vol. 40, No. 10, Oct. 1997, pp. 1843-1851.

Svanborg et al., "Cytokine responses during mucosal infections: role in disease pathogenesis and host defence," 1999 *Curr Opin Microbiol*, 2:99-105.

Svangård et al., "Cytotoxic Cyclotides from *Viola tricolor*," 2004 *J Nat Prod*, 67(2):144-147.

Tang et al., "A Cyclic Antimicrobial Peptide Produced in Primate Leukocytes by the Ligation of Two Truncated Alpha-Defensins," Oct. 1999 *Science*, 286(5439):498-502.

Thongyoo et al., "Chemical and biomimetic total syntheses of natural and engineered MCoTI cyclotides," 2008 *Org Biomol Chem*, 6:1462-70.

Trabi et al., "Variations in Cyclotide Expression in *Viola* Species," 2004 *J Nat Prod*, 67:806-810.

Vlieghe et al., "Synthetic therapeutic peptides: science and market," Jan. 2010 *Drug Discov Today*, 15(1/2):40-56.

Wang et al., "Anti-HIV Cyclotides from the Chinese Medicinal Herb *Viola yedoensis*," 2008 *J Nat Prod*, 71(1):47-52.

Wang et al., "CyBase: a database of cyclic protein sequences and structures, with applications in protein discovery and engineering," 2008 *Nucleic Acids Res*, 36:D206-D210.

Werle et al., "Evaluation and improvement of the properties of the novel cystine-knot microprotein McoEeTI for oral administration," 2007 *Int J Pharm*, 332:72-79.

Wong et al., "Orally Active Peptidic Bradykinin $B_1$ Receptor Antagonists Engineered from a Cyclotide Scaffold for Inflammatory Pain Treatment," 2012 *Angew Chem Int Ed*, 51(23):5620-5624.

Zhou, "Identification of a Ca2+-Binding Domain in the Rubella Virus Nonstructural Protease," Jul. 2007 *J Virol*, 81(14):7517-7528.

International Search Report and Written Opinion issued in connection with International Patent Application No. PCT/EP2012/076739, filed Dec. 21, 2012: 23 pgs.

Extended European Search Report for Application No. 18172126.7 dated Dec. 3, 2018 (9 pages).

\* cited by examiner

A

B

```
kalata B1    GLPVCGETCVGGTCNTPGCTCSWPVCTRN
kalata B2    GLPVCGETCFGGTCNTPGCSCTWPICTRD
```

A

B

A

B

C

24h

36h

24h

36h

A

B

| | | | | |
|---|---|---|---|---|
| A. T20K | 10 mg/kg T20K | PBS | i.p. | n=10 |
| B. T20K | 10 mg/kg T20K | PBS | i.p. | n=10 |
| C. T20K | 10 mg/kg T20K | PBS | i.p. | n=10 |
| D. Naïve | | | | n=10 |

A

B

C

D

E

A

B

C

D

E

F

G

H

I

J

A

B

A

B

C

D

CYCLOTIDES AS IMMUNOSUPPRESSIVE AGENTS

CROSS-REFERENCE

This application is a divisional of U.S. application Ser. No. 15/244,244, filed Aug. 23, 2016 and which is a continuation application of U.S. application Ser. No. 14/366,427, filed Jun. 18, 2014 and now U.S. Pat. No. 9,453,052, and which is a § 371 U.S. National Stage Entry of International Application No. PCT/EP2012/076739, filed 21 Dec. 2012, which claims priority to European Application No. 12196918.2 filed 13 Dec. 2012, and claims priority to European Application No. 11195413.7 filed 22 Dec. 2011, each of which is incorporated by reference herein in its entirety. A certified copy of European Application No. 12196918.2 filed 13 Dec. 2012 and European Application No. 11195413.7 filed 22 Dec. 2011, was provided in, and is available in, U.S. patent application Ser. No. 14/366,427 for which certified copy is available in PAIR.

SEQUENCE LISTING

This application contains a Sequence Listing electronically submitted via EFS-Web to the United States Patent and Trademark Office as an ASCII text file entitled "258-00270103-SequenceListing_ST25.txt" having a size of 11 kilobytes and created on Oct. 2, 2018. The information contained in the Sequence Listing is incorporated by reference herein.

The present invention relates to a pharmaceutical composition comprising a cyclotide for use in immune suppression as well as to a method for immune suppression comprising the step of administering an effective amount of a pharmaceutical composition comprising such a cyclotide to a subject in need thereof. The present invention also relates to a pharmaceutical composition comprising a cyclotide for use in treating or preventing a disorder selected from the group consisting of (i) an autoimmune disorder; (ii) a hypersensitivity disorder; and (iii) a lymphocyte-mediated inflammation. Likewise, the present invention also relates to a method for treating or preventing a disorder selected from the group consisting of (i) an autoimmune disorder; (ii) a hypersensitivity disorder; and (iii) a lymphocyte-mediated inflammation. The present invention further relates to a method of screening for and/or selecting an immunosuppressive cyclotide or a mutation which results in a mutated cyclotide having an induced or enhanced immunosuppressive activity. The present invention further relates to a method of producing an immunosuppressive cyclotide or an immunosuppressive pharmaceutical composition. The present invention further relates to a mutated cyclotide having immunosuppressive activity and a pharmaceutical composition comprising the same.

Naturally-occurring circular peptides with potential pharmaceutical applications have been found in various organisms (summarized in Craik, 2006, Science, 311, 1563-1564), such as bacteria (e.g., bacteriocin AS-48 (Martinez-Bueno, 1994, J Bacteriol, 176, 6334-6339) and Microcin J25 (Rosengren, 2003, J Am Chem Soc, 125, 12464-12474)), plants (e.g. sunflower trypsin inhibitors (Luckett, 1999, J Mol Biol, 290, 525-533; Mylne, 2011, Nat Chem Biol, 7, 257-259)) and animals (e.g. rhesus monkey θ-defensins (Tang, 1999, Science, 286, 498-502)). One of the largest, but mostly unexplored, group of natural circular peptides are the plant cyclotides (Gruber, 2010, Curr Pharm Des, 16, 3071-3088).

In general, cyclotides are head-to-tail cyclized peptides representing an abundant and diverse group of (ribosomally-) synthesized plant peptides containing a cyclic cystine-knotted structure. Moreover, cyclotides are a natural combinatorial library of circular cystine-knot peptides with great stability. Cyclotides are explored for their distribution in plants, although little is known about the individual peptide content of a single species.

The circular cyclotide chain usually consists of ~30 amino acids, including six conserved cysteines that form three disulfide bonds arranged in a cyclic cystine-knot (CCK) motif (Craik, 1999, J Mol Biol, 294, 1327-1336), whereas the inter-cysteine sequences can tolerate a wide range of residue substitutions and, hence, the cyclotide scaffold may serve as a natural combinatorial peptide template (Clark, 2006, Biochem J, 394, 85-93).

The remarkable structural features make cyclotides extremely resistant to enzymatic, chemical and thermal degradation (Colgrave, 2004, Biochemistry, 43, 5965-5975). In contrast to non-ribosomal synthesized plant metabolites, cyclotides are true gene products and their biosynthesis involves ribosomal precursor synthesis, enzymatic processing (Gillon, 2008, Plant J, 53, 505-515; Saska, 2007, J Biol Chem, 282, 29721-29728) and protein folding events (Gruber, 2007, J Biol Chem, 282, 20435-20446). Furthermore, cyclotides possess a wide range of biological activities, e.g., insecticidal (Barbeta, 2008, Proc Natl Acad Sci USA, 105, 1221-1225; Gruber, 2007, Toxicon, 49, 561-575), nematocidal (Colgrave, 2008, Biochemistry, 47, 5581-5589; Colgrave, 2009, Acta Trop, 109, 163-166), anti-fouling (Goransson, 2004, J Nat Prod, 67, 1287-1290), and anti-HIV (Wang, 2008, J Nat Prod, 71, 47-52; Ireland, 2008, Biopolymers, 90, 51-60) activities, as well as cytotoxicity to lymphoma cell lines (Svangard, 2004, J Nat Prod, 67, 144-147; Lindholm, 2002, Mol Cancer Ther, 1, 365-369).

The discovery of the first cyclotide, kalata B1, was based on its presence in tea/extract from the Rubiaceae species *Oldenlandia affinis* (R&S) DC. used in African indigenous medicine to accelerate childbirth (Gran, 1970, Medd Nor Farm Selsk, 12, 173-180; 1973, Acta Pharmacol Toxicol (Copenh), 33, 400-408; Gruber, 2011, Planta Med, 77, 207-220). The plant *O. affinis* (Rubiaceae) is commonly known to scientists in the field of ethnopharmacology and peptide chemistry as a prototypical source of cyclotides.

Since their discovery in the coffee-family (Rubiaceae), cyclotides have been extensively studied in the violets (Violaceae), and have recently been found in legumes (Fabaceae) (Poth, 2011, Proc Natl Acad Sci USA, 108, 10127-10132; Poth, 2011, ACS Chem Biol, 6, 345-355; Nguyen, 2011, J Biol Chem, 286, 24275-24287). There is an increasing effort to screen plants of different families for the occurrence and distribution of cyclotides. Today it is evident that many other cyclotides exist. Recently it has been estimated that there are at least 50,000 novel cyclotides to be discovered in Rubiaceae (Gruber, 2008, Plant Cell, 20, 2471-2483) and another ~9,000 in Violaceae (Simonsen, 2005, Plant Cell, 17, 3176-3189; Trabi, 2004, J Nat Prod, 67, 806-810), but researchers are only at the beginning to understand their variety and distribution in plants (Gruber, 2010, Biopolymers, 94, 565-572). Biologically, cyclotides are mainly explored for applications in agriculture and drug design due to their enormous stability (Craik, 2001, Toxicon, 39, 1809-1813; Craik, 2007, Curr Opin Drug Discov Devel, 10, 176-184; Craik, 2006, Biopolymers, 84, 250-266; Craik, 2001, Toxicon, 39, 43-60). The cyclotide kalata B1 has earlier been reported to cause hemolysis and membrane disruption at concentrations above ~50 μM (Barry, 2003, Biochemistry, 42, 6688-6695; Henriques, 2011, J Biol Chem, 286, 24231-24241).

With respect to the therapeutic applications of cyclotides, the scientific and patent literature is primarily related to the use of cystine knot scaffolds for the production of peptide-based drugs. For example, U.S. Pat. No. 7,960,340 B2 is based on the concept that the cyclotide molecular framework is ultra-stable and that it is possible to modify loops of the framework by replacing them with pharmaceutically relevant bioactive sequences, thereby stabilizing this bioactive sequences. Several recent papers have reported examples of this cyclotide grafting strategy. Subsequently, various studies applied cyclotides as scaffolds for therapeutically active peptides (see, for instance, Smith, 2011, Expert Opin. Ther. Patents 21, 1657-1672; Gunasekera, 2008, J Med Chem, 51, 7697-704; Thonbyoo, 2008, Org Biomol Chem, 6, 1462-70; and Cemazar (20th American-Peptide-Society Symposium; Montreal, CANADA, Jun. 26-30, 2007, Biopolymers 88, 4, SI, 2007, 523. Examples include the development of an inhibitor of angiogenesis with applications in cancer therapy by the grafting of an antiangiogenic sequence onto the cyclotide kalata B1 (Gunasekera; 2008; J Med Chem; 51; 7697-704) and the development of an inhibitor of a protease from foot-and-mouth disease virus onto the MCoTI-II cyclotide framework (Thonbyoo; 2008; Org Biomol Chem; 6; 1462-70). It has also been shown that cyclotides have the activity of inhibiting tryptase, the major secretory protease of human mast cells (WO 06032436). Furthermore, cyclotides were shown to exhibit cytotoxic activities and their selective toxicity to cancer cell lines has opened the possibility of anti-cancer applications (Hermann; 2008; Phytochemistry; 69; 939-52, Lindholm; 2002; Mol Cancer Ther; 1; 365-9, Svangard; 2004; J Nat Prod; 67; 144-7; Burman; 2010; Biopolymers Pept Sci; 94; 626-34; Gerlach; 2010; Biopolymers; 94; 617-25). However, cytotoxicity effects are known to cause side effects.

The body's immune system is a very powerful weapon against pathogens, but malfunctioning can cause an over-reactivity of this defense machinery and, in some instances, lead to auto-immune diseases, such as rheumatoid arthritis (RA) or Crohn's disease. Immunosuppression, the targeted reduction of the activation or efficacy of the immune system, is a potential approach for the treatment of these conditions. Because T-lymphocytes have the greatest powerful impact during defence response of the immune system, most immunosuppressive medications aim to act on these cells. One of the clinically used immunosuppressive drugs of choice to treat or suppress an "over-activity" of lymphocytes, for example after transplantation surgery or in cases of severe RA, is the fungal, cyclic non-ribosomal peptide cyclosporine A (de Mattos, 2000, Am J Kidney Dis, 35, 333-346; Matsuda, 2000, Immunopharmacology, 47, 119-125; Schreiber, 1991, Science, 251, 283-287). However, cyclosporine A has many and sometimes severe side effects (de Mattos, 2000, Am J Kidney Dis, 35, 333-346). In addition, leaf extracts of *Betula pendula* have been traditionally used for treating RA or osteoarthritis.

Beside this, further problems have to be faced when trying to suppress the immune system. For example, the proof of anti-proliferative effects by holding the cells in an "inactive" state at which they are still viable, but aren't able to grow and proliferate, without causing cell death is a crucial precondition to classify a substance as immunosuppressant, because cytotoxicity would cause side effects. Moreover, therapeutic peptides often lack oral bioavailability due to fast degradation upon ingestion and have poor drug permeation due to their hydrophilic nature.

Thus, the technical problem underlying the present invention is the provision of improved means and methods for suppressing the immune system/for immunosuppression and for treating/preventing corresponding diseases/disorders.

The technical problem is solved by providing the embodiments characterized herein and in the appended claims.

In the context of the present invention, the proof of principle was made that cyclotides and related cystine-knot peptides or cyclotide mutants/variants can be used for suppressing the immune system/immune suppression, as immunosuppressive agents or for the suppression/reduction of the efficacy of the immune system. This provides for the possibility to make use of the superior, advantageous (pharmacological) features of cyclotides also in the field of suppression of the immune system/immune suppression.

In particular, it was surprisingly found in the context of this invention that there are cyclotides existing which are capable to decrease or arrest proliferation of (activated) immune cells/cells of the immune system (for example peripheral blood mononuclear cells (PBMC) or (T-)lymphocytes). Furthermore, the anti-proliferative effect induced by the cyclotides was shown not to cause cell death by either apoptosis or necrosis, but to inhibit the growth of the immune cells in a cytostatic fashion. In addition, vaccination with a cyclotide (for example kalata B1) resulted in a reduction in the incidence and severity of Experimental Autoimmune Encephalomyelitis (EAE) in an EAE mouse model for multiple sclerosis (MS). Moreover, it was shown that vaccination with a cyclotide (for example kalata B1), leads to the production of an anti-inflammatory T-cell response.

Accordingly, the present invention relates to a pharmaceutical composition comprising (as the active ingredient) a cyclotide, in particular an anti-immune cell-proliferative cyclotide, for use in immune suppression. Moreover, the present invention relates to a method for immune suppression comprising the step of administering an effective amount of a pharmaceutical composition comprising (as the active ingredient) a cyclotide, in particular an anti-immune cell-proliferative cyclotide, to a subject/patient in need thereof.

In the context of the present invention the immunosuppressive properties of (plant) cyclotides were characterized for the first time. Combined with the unique structural features and enormous stability of cyclotides, these results open new avenues for the application of native and synthetically-optimized (plant) cyclotides in immune-related disorders, in particular in immune suppression.

In particular, it was demonstrated in the context of the present invention that there are anti-proliferative effects of an extract from the coffee-family plant *O. affinis* to cells of the human immune system (for example lymphocytes). In addition, kalata B1 was specifically identified as one active component responsible for the observed cytostatic effects. Moreover, it was demonstrated that, in a defined concentration range, no cell death by apoptosis or necrosis was caused. Moreover, it was shown that EAE mice treated with a cyclotide (for example kalata B1) displayed significantly milder clinical signs and displayed improvement in disease severity (see, for example, FIGS. 10A and B). In addition, vaccination with a cyclotide (for example kalata B1) leads to the production of an anti-inflammatory T-cell response.

The presented results have further impact to the general field of cystine-knot peptides and greatly enhance the possibilities for their potential therapeutic applications. The oral bioavailability of cyclotides and cystine-knot peptides, the availability of recombinant and synthetic production techniques as well as the plasticity of the cystine-knot framework, which is amenable to a wide range of amino acid substitutions, provides a promising basis for future mechanistic studies of their activity on immune cells (e.g. lymphocytes) and in vivo applications (for example in model systems related to malfunctioning of immune cells in general and in particular, the over-reactivity of lymphocytes).

As documented herein below and in the appended examples, the anti-proliferative effects of cyclotides, in particular plant cyclotides, on primary cells of the human immune system (primary human PBMC or T-lymphocytes) was shown using biological and immunological endpoints in cell-based test systems. It was further shown that the effects have a defined concentration range and were not due to cytotoxic effects. More particular, LC-MS quantification of the active O. affinis plant extract triggered the characterization of the anti-proliferative activity of kalata B1, one of the most abundant cyclotides in this extract, on primary activated human lymphocytes. For this purpose, a crude O. affinis cyclotide extract was analyzed using an alternative peptidomics workflow and a rapid technique for the characterization of cyclotides in plant.

It was shown in the appended examples that a cyclotide (for example the kalata B1-mutant cyclotide T20K, a cyclotide comprising SEQ ID NO. 7; 4 μM) is capable of reducing the expression level of the IL-2 receptor and the IL-2 production. The magnitude of the effect was similar to the treatment with cyclosporine A (5 μg/ml) and this anti-proliferative effect of the cyclotide could be reversed by addition of exogenous IL-2. Furthermore, it was shown that the cyclotide reduced the release of effector molecules IFN-gamma and TNF-alpha in PBMCs, however this reduction was only of transient nature. This is in contrast to CsA-treatment, which led to a retained reduction of TNF-alpha and IFN-gamma over time. A reduction in IL-2 release upon treatment with cyclotides (for example with the kalata B1-mutant cyclotide T20K, a cyclotide comprising SEQ ID NO. 7; 200 μg/100 μl/mouse) was also shown in vivo (for example in an EAE mouse model (C57BL/6J)).

Without being bound by theory, the cyclotide-mediated anti-proliferative effect is mediated through an IL-2-depending mechanism. The effector functions of (activated) PBMC (for example lymphocytes) were also reduced by cyclotide treatment (for example by treatment with T20K).

Moreover, the effect on IL-2 synthesis and IL-2 receptor expression may be directly influenced by cyclotides or independently mediated. The herein defined cyclotides may have a similar mode of action as compared to CsA. CsA is known to directly influence the IL-2 production. Further, CsA is able to form a complex with cyclophilin and the CsA-cyclophilin complex can bind to calcineurin and inhibit its function in Ca-signalling. This leads to a reduced NFATc transcription and hence IL-2 synthesis. The immunosuppressive action of CsA hence requires CsA to enter the cells and form a direct contact with cyclophillin and calcineurin. As shown in the appended Examples T20K can enter T-cells, i.e. it can pass (actively or passively) the membrane (see FIG. 24). Accordingly and without being bound by theory, T20K may interact with an extracellular target or transporter or may enter the T-cell passively and interact with an intracellular target. Also a combination of extracellular and intracellular activity of T20K is possible. Without being bound by theory, the herein defined cyclotides, in particular kalata B1 or T20K, may be able to enter cells and affect the IL-2 synthesis in CsA manner or may remain on the outside of its target cells and lead to a change in the membrane potential by interaction with surface molecules, receptors or ion-channels. Most importantly, the herein defined cyclotides, in particular kalata B1 or T20K, may interact with a T-cell receptor.

Without being bound by theory, the anti-proliferative mechanism may be due to direct interaction of the herein defined cyclotides with the IL-2 receptor (for example, T20K is able to down-regulate the IL-2 alpha-chain CD25 receptor expression on the surface of PBMCs as shown in the appended examples). For example, and also without being bound by theory, binding of the herein defined immunosuppressive cyclotides to the IL-2 alpha-chain may occupy the interaction site for binding of the beta- and gamma-chain and hence inhibit complex formation. However, this IL-receptor complex formation is important for activation of the T-lymphocyte in order to receive signals from released IL-2. Only after binding of IL-2 to its receptor, the T-lymphocytes will initiate a normal proliferation. If binding is inhibited, for example by above described mechanism, the T-cells remain in a non-proliferative state. One drug on the pharmaceutical market, i.e. Simulect®, is used as anti-proliferative agent on the basis of CD25 receptor interaction. The active principle is a chimeric monoclonal antibody, Basiliximab, which binds to the IL-2 receptor alpha chain and hence inhibits binding of endogenous IL-2.

In the context of the present invention, the anti-proliferative and cytotoxic effects of a crude O. affinis cyclotide-containing plant extract towards activated primary human lymphocytes was characterized. To identify the individual molecular peptide components of this immunosuppressive cyclotide mixture, biological in vitro analysis were combined with chemical characterization of the content of individual peptides (cyclotides) in the crude extract of this plant using an optimized rapid peptidomics workflow.

In particular, an optimized protocol for the analysis of cyclotide-containing plant extracts by combining nanoflow LC-MS/MS and automated database analysis was used to determine the content of distinct peptides (by molecular weight and peptide sequence) in the cyclotide-containing plant O. affinis.

The combination of nano LC-MS/MS and LC-MS reconstruction, as well as automated database searching (e.g. using the ERA tool (Colgrave, 2010, Biopolymers. 94, 592-601)) is a rapid and useful technique for the identification of cyclotides in crude extracts.

Compared to an earlier study from Plan (2007, ChemBioChem, 8, 1001-1011), which described the first cyclotide fingerprint of O. affinis using classical peptide purification via analytical HPLC and offline MS/MS sequencing, 8 additional known cyclotides were identified and shown to be able to provide a list of ~50 peptide masses corresponding to cyclotides of which some can be identified by peptide fingerprint analysis in CyBase (the cyclotide database (Wang, 2008, Nucleic Acids Res, 36, D206-210)). This suggests that the number of cyclotides to be found in a single species may be >70 and is, therefore, at least twice the number than earlier anticipated (on average 34 cyclotides per species (Gruber, 2008, Plant Cell, 20, 2471-2483). This, of course, has a huge impact on the determination of the overall number of cyclotides in the plant kingdom and consequently would lead to a necessary revision of the number of novel cyclotides to be discovered in plants.

Using the above described improved peptidomics workflow, nearly all currently known cyclotides and an even greater number of novel peptide masses corresponding to other known or novel cyclotides (by molecular weight)

could be identified in crude cyclotide extract from the plant *O. affinis*. The cyclotides kalata B1 and kalata B2 were found to be the main peptide components, accounting for approx. 34% of the overall cyclotide content in *O. affinis*.

By using flow cytometric-based forward-side-scatter analysis, it was further demonstrated that the cyclotide-containing extract exhibits a dose-dependent (50-100 μg/mL) decrease of activated proliferating PBMC compared to untreated stimulated control (FIGS. 2A and B). Simultaneously, a constant content of viable, resting PBMC, without accumulation of dead cells was observed, showing that the applied concentrations of the cyclotide extract are not harmful to the cells.

Several additional characteristics regarding drug delivery conduce to the above described immunosuppressant potential of cyclotides: (i) retained activity upon oral administration as tea/extract (in humans) (Gran, 1970, Medd Nor Farm Selsk, 12, 173-180), (ii) great stability in plasma and against gastro-intestinal proteases (Colgrave, 2004, Biochemistry, 43, 5965-5975; Colgrave, 2005, J Chromatogr A, 1091, 187-193) and (iii) the presence of surface-exposed hydrophobic patches (Clark, 2006, Biochem J, 394, 85-93).

Generally, therapeutic peptides often lack oral bioavailability due to fast degradation upon ingestion and have poor drug permeation due to their hydrophilic nature (Vlieghe, 2010, Drug Discov Today, 15, 40-56; Werle, 2007, Int J Pharm, 332, 72-79). Cyclotides and related cystine-knot peptides are likely to overcome these problems (Kolmar, 2009, Curr Opin Pharmacol, 9, 608-614). As corresponding proofs of concept there are two examples in the literature: (i) a synthetically-engineered cyclic conotoxin has recently been confirmed as an oral active circular peptide drug for the treatment of neuropathic pain in vivo (Clark, 2010, Angew Chem Int Ed Engl, 49, 6545-6548), and (ii) a synthetic cyclotide containing the sequence motif of a bradykinin B1 antagonist has been engineered based on the native kalata B1 peptide template and has been confirmed to be orally active and bioavailable in a mouse model of inflammatory pain (Wong, 2012, Angew Chem Int Ed Engl, 51(23), 5620-4). Another feature of cyclotides with respect to applications as peptide drugs is that they are synthesized gene products (Jennings, 2001, Proc Natl Acad Sci USA, 98, 10614-10619) and can therefore be produced in large quantity by recombinant techniques (Kimura, 2006, Angew Chem Int Ed Engl, 45, 973-976) or in plant suspension cultures (Seydel, 2007, Appl. Microb. Biotechnol., 77, 275-284). These cyclotide production techniques and the availability of solid-phase peptide synthesis strategies (Clark, 2010, Biopolymers, 94, 414-422) offer opportunities for the optimization of the cyclotide-framework, which is amenable to a wide range of amino acid substitutions (see also FIG. 1).

Not at least, the proof of anti-proliferative effects by holding the cells in an "inactive" state at which they are still viable, but aren't able to proliferate, without causing cell death, in a certain dose range is a crucial precondition to classify a substance as immunosuppressant, because cytotoxicity would cause side effects.

It was further demonstrated in the context of the present invention that, upon treatment (for example of an EAE mouse model (C57BL/6J)) with cyclotides (for example with the kalata B1-mutant cyclotide T20K, a cyclotide comprising SEQ ID NO. 7; 200 μg/100 μl/mouse), the clinical score (for example the EAE score) significantly decreases (for example the weight of EAE mice). Importantly, cyclotide treatment does not cause a cytotoxic effect since cyclotide treatment does not lead to a body weight reduction.

In general, the meaning of the term "cyclotide" is known in the art and the term "cyclotide" is correspondingly used herein. In particular, "cyclotides" as used herein are head-to-tail cyclized peptides which cyclotide chain includes six conserved cysteine residues capable to form three disulfide bonds arranged in a cyclic cystine-knot (CCK) motive. The inter-cysteine sequences of a cyclotide can tolerate a wide range of residue substitutions (see, for example, Clark, loc. cit. and FIG. 1). In one aspect, the term "cyclotide" used herein refers to cyclotides as described in Craik (1999, loc. cit.), Clark (2006, loc. cit.) and, in particular, in U.S. Pat. No. 7,592,533 B1.

In particular, a cyclotide to be used in the context of this invention comprises an amino acid sequence capable of forming a cyclic backbone wherein said cyclic backbone comprises the structure of formula I:

$$\text{Cyclo}(C[X_1 \ldots X_a]C[X^I_1 \ldots X^I_b]C[X^{II}_1 \ldots X^{II}_c]C[X^{III}_1 \ldots X^{III}_d]C[X^{IV}_1 \ldots X^{IV}_e]C[X^V_1 \ldots X^V_f]) \quad (I)$$

wherein
(i) C is cysteine;
(ii) each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$, and $[X^V_1 \ldots X^V_f]$ represents one or more amino acid residues, wherein each one or more amino acid residues within or between the sequence residues may be the same or different; and
(iii) a, b, c, d, e, and f represent the number of amino acid residues in each respective sequence and each of a to f may be the same or different and range from 1 to about 20.

Preferably, a is 3 to 6, b is 4 to 8, c is 3 to 10, d is 1, e is 4 to 8, and/or f is 5 to 13.

Preferably, the cyclotide to be used herein comprises the amino acid stretch of formula II (SEQ ID NO. 17)

$$\text{Xxx}_1\text{-Leu-Pro-Val-Cys-Gly-Glu-Xxx}_2\text{-Cys-Xxx}_3\text{-Gly-Gly-Thr-Cys-Asn-Thr-Pro-Xxx}_1\text{-Cys-Xxx}_1\text{-Cys-Xxx}_1\text{-Trp-Pro-Xxx}_1\text{-Cys-Thr-Arg-Xxx}_1 \quad (II),$$

wherein $Xxx_1$, $Xxx_2$ and $Xxx_3$ is any amino acid, non-natural amino acid or peptidomimetic, preferably an aliphatic amino acid. In particular, $Xxx_2$ may be any amino acid, non-natural amino acid or peptidomimetic but not Lys and/or $Xxx_3$ may be any amino acid, non-natural amino acid or peptidomimetic but not Ala or Lys. Preferably, $Xxx_2$ and/or $Xxx_3$ of formula II are not mutated at all. More particular, $Xxx_1$ may be Gly, Thr, Ser, Val, Ile, Asn, Asp or, preferably, Lys, $Xxx_2$ may be Thr, and/or $Xxx_3$ may be Val or Phe. Even more particular, $Xxx_1$ at position 1 of formula II may be Gly, $Xxx_1$ at position 18 of formula II may be Lys or, preferably, Gly, $Xxx_1$ at position 20 of formula II may be Thr, Ser or, preferably, Lys, $Xxx_1$ at position 22 of formula II may be Ser or Thr, $Xxx_1$ at position 25 of formula II may be Val or Ile, $Xxx_1$ at position 29 of formula II may be Asn, Asp or, preferably, Lys, $Xxx_2$ of formula II may be Thr and/or $Xxx_3$ of formula II may be Val or Phe.

The specifically defined amino acid residues of formula II may also vary depending on the particular (type of) cyclotide. Hence, what has been said with respect to $Xxx_1$, $Xxx_2$ and/or $Xxx_3$, does not only apply to formula II but also to the corresponding amino acid residues of other cyclotides not comprising the particular amino acid stretch of formula II. In this context, "corresponding" particularly means amino acid residues at the same or similar position(s).

Non-limiting specific examples of a cyclotide to be used according to this invention is a cyclotide comprising:

(i) an amino acid sequence selected from the group consisting of SEQ ID NOs: 7, 5, 1, 4, 6, 2 and 3;
(ii) an amino acid sequence encoded by a nucleotide sequence selected from the group consisting of SEQ ID NOs: 11, 15, 12 and 16;
(iii) an amino acid sequence encoded by a nucleotide sequence encoding an amino acid sequence selected from the group consisting of SEQ ID NOs: 7, 5, 1, 4, 6, 2 and 3; or
(iv) an amino acid sequence that is at least 70%, preferably at least 80%, more preferably at least 90%, even more preferably at least 95%, even more preferably at least 98% and even more preferably at least 99% identical to any amino acid sequence of (i) to (iii).

Further, non-limiting examples of cyclotides to be used are cyclotides consisting of a head-to-tail cyclized form of an amino acid sequence as defined in any of (i) to (iv), supra.

In a preferred embodiment, the cyclotide to be used is kalata B or a kalata B-type cyclotide. In an even more preferred embodiment, the cyclotide is kalata B2 or, most preferably, kalata B1. The cyclotides kalata B1 and B2 differ by only five amino acid positions (see FIG. 6), namely Val to Phe (loop 2) and conservative replacements of Thr to Ser (loop 4), Ser to Thr (loop 5), Val to Ile (in loop 5) and Asn to Asp (in loop 6) in kalata B2. These substitutions have no significant structural consequences ($RMSD_{backbone\ kB1/kB2}$=0.599 Å, see FIG. 6) and the two peptides have a similar bioactivity profile (Gruber, 2007, Toxicon, 49, 561-575).

It will be understood that for the various cyclotides to be used in the context of the present invention a certain flexibility and variability in the primary sequence, i. e. the amino acid sequence backbone, is possible, as long as the overall secondary and tertiary structure of the respective peptides, which is defined by at least some fixed amino acid residues and by their spatial arrangement, is ensured (see, e.g., formulas I and II, supra).

Based on the teaching provided herein, the skilled person is, one the one hand, readily in the position to find out/identify corresponding mutants/variants of the cyclotides which act according to the invention. One the other hand, the skilled person is able to test whether a given cyclotide mutant/variant still has the desired function, for example at least one of the functions as described herein elsewhere. Corresponding experimental guidance for such tests, i.e. respective assays, are exemplarily provided and described herein, particularly in the appended examples.

Hence, in one aspect, the present invention also relates to the use of mutant or variant forms of the herein defined (native) cyclotides, in particular to the use of mutant or variant forms of the cyclotides as depicted in Table 1, more particular of mutant or variant forms of kalata B2 or, preferably, kalata B1. The mutant or variant forms may be (synthetically) optimized, i.e. they may be better suited for immunosuppression as compared to their non-mutant/non-variant form. Non-limiting examples of mutant/variant forms of cyclotides are the cyclotides as depicted in Table 1, wherein the same mutations as in any one of SEQ ID NO: 3 to 7 have been performed or corresponding mutations at amino acid positions which correspond to the amino acid positions which have been mutated in any one of SEQ ID NO: 3 to 7 have been performed.

If not mentioned differently, the term "cyclotide(s)" when used herein is envisaged to also encompass "cyclotide mutant(s)/variant(s)". Non-limiting examples of mutant/variant/modified cyclotides according to this invention are given in section (iv), supra or are cyclotides consisting of a head-to-tail cyclized form of an amino acid sequence as defined in section (iv), supra. Further examples of mutant/variant cyclotides are cyclotides comprising an amino acid sequence selected from the group consisting of SEQ ID NOs: 3 to 7 or cyclotides consisting of a head-to-tail cyclized form of an amino acid sequence selected from the group consisting of SEQ Id NOs: 3 to 7.

As to the mutants/variants of the cyclotides it is, for example, envisaged that one or more amino acids of said peptides are replaced by other one or more naturally-occurring or synthetic amino acids. In this context, it is preferred that this/these amino acid exchange(s) is/are (a)conservative amino acid exchange(s), i.e. that the replacement amino acid belongs to the same category of amino acids than the amino acid to be replaced. For example, an acidic amino acid may be replaced by another acidic amino acid, a basic amino acid may be replaced by another basic amino acid, an aliphatic amino acid may be replaced by another aliphatic amino acid, and/or a polar amino acid may be replaced by another polar amino acid.

It is particularly envisaged that the amino acid exchanges which lead to mutants/variants of the disclosed cyclotides are such that the pattern of polarity and charge within the tertiary structure of the resulting mutant/variant still (substantially) mimics/corresponds to the three-dimensional structure of the respective cyclotide.

Further examples of mutant or variant cyclotides are kalata B1 or kalata B2 (or the disclosed mutants/variants thereof) or a cyclotide consisting of a head-to-tail cyclized form of the amino acid sequence of SEQ ID NO: 1 or 2 having
(i) at least 1, 2, 3, 4, 5, 6, 7, 8, 9 or 10 of its acidic amino acid residues replaced by a different amino acid residue selected from the group consisting of acidic amino acid residue;
(ii) at least 1, 2, 3, 4, 5, 6, 7, 8, 9 or 10 of its basic amino acid residues replaced by a different amino acid residue selected from the group consisting of basic amino acid residues; and/or
(iii) at least 1, 2, 3, 4, 5, 6, 7, 8, 9 or 10 of its aliphatic amino acid residues replaced by a different amino acid residue selected from the group consisting of aliphatic amino acid residues.

Other mutant/variant cyclotides comprise the amino acid stretch of formula II, but having
(i) at least 1, 2, 3, 4, 5, 6, 7, 8, 9 or 10 of the (remaining specific) acidic amino acid residues replaced by a different amino acid residue selected from the group consisting of acidic amino acid residues;
(ii) at least 1, 2, 3, 4, 5, 6, 7, 8, 9 or 10 of the (remaining specific) basic amino acid residues replaced by a different amino acid residue selected from the group consisting of basic amino acid residues; and/or
(iii) at least 1, 2, 3, 4, 5, 6, 7, 8, 9 or 10 of the (remaining specific) aliphatic amino acid residues replaced a different amino acid residue selected from the group consisting of aliphatic amino acid residues.

In general, the meaning of the term "amino acid" or "amino acid residue" is known in the art and is used herein accordingly. Thereby, it is of note that when an "amino acid" is a component of a peptide/protein the term "amino acid" is used herein in the same sense than "amino acid residue".

Particularly, an "amino acid" or "amino acid residue" as referred to herein is envisaged to be a naturally-occurring amino acid, more preferably a naturally-occurring L-amino acid. However, albeit less preferred, an "amino acid" or "amino acid residue" in context of this invention may also be a D-amino acid or a non-naturally-occurring (i.e. a synthetic) amino acid, like, for example, norleucine, β-alanine, or selenocysteine.

Also known in the art is the meaning of the terms "acidic amino acid(s)", "basic amino acid(s)", "aliphatic amino acid(s)" and "polar amino acid(s)" (see, for example, Stryer, Biochemie, Spectrum Akad. Verlag, 1991, Item I. 2.). These terms are correspondingly used throughout this invention. Thereby, the particular provisos given herein with respect to the cyclotides of the invention also apply.

Particularly, the term "acidic amino acid(s)" as used herein is intended to mean an amino acid selected from the group comprising Asp, Asn, Glu, and Gln, the term "basic amino acid(s)" as used herein is intended to mean an amino acid selected from the group comprising Arg, Lys and His, the term "aliphatic amino acid(s)" as used herein is intended to mean any amino acid selected from the group comprising Gly, Ala, Ser, Thr, Val, Leu, Ile, Asp, Asn, Glu, Gln, Arg, Lys, Cys and Met, and the term "polar amino acid(s)" as used herein is intended to mean any amino acid selected from the group comprising Cys, Met, Ser, Tyr, Gln, Asn and Trp.

In a preferred embodiment, the cyclotides and mutant/variant cyclotides to be used in accordance with the present invention are cyclotides having at least one of their amino acid residues corresponding to $Xxx_1$ of formula II, preferably corresponding to $Xxx_1$ at position 20 and/or 29 of formula II, replaced by (a) different amino acid residue(s). Likewise, the cyclotides and mutant/variant cyclotides to be used in accordance with the present invention may also be cyclotides having at least one of their amino acid residues corresponding to amino acid position 1, 18, 20, 22, 25 and/or 29, preferably corresponding to amino acid position 20 and/or 29, replaced by (a) different amino acid residue(s). In this context, "corresponding to" particularly means the same amino acid amino acid residue(s) and/or at the same or similar position(s). Such (a) different amino acid residue(s) may, for example, be useful for labelling the respective mutant/variant cyclotides. A non-limiting example of such (a) different amino acid residue(s) is Lys. Non-limiting examples of respective mutant/variant cyclotides are mutant/variant cyclotides comprising or consisting of (a head-to-tail cyclized form of) a amino acid sequence of SEQ ID NO: 4 to 7, wherein SEQ ID NOs: 5 or 7 are preferred.

In a specific aspect, the mutant/variant cyclotides to be used according to the invention are cyclotides not having replaced one or more of their amino acid residues lying between the "first" and the "second" Cys (corresponding to the "first" and "second" Cys, respectively, as depicted in formula I, supra) and/or between the "second" and the "third" Cys (corresponding to the "second" and "third" Cys, respectively, as depicted in formula I, supra).

Preferably, in such mutant/variant cyclotides none of the amino acid residues flanking the "second" Cys, in particular neither the amino acid residue next to the "second" Cys in the N-terminal direction of formula I nor the amino acid residue next to the "second" Cys in the C-terminal direction of formula I, are replaced by another amino acid residue, in particular not by an Lys or Ala residue.

It is preferred that the used cyclotides and mutants/variants thereof lack sites susceptible for hydrolysis or cleaving proteases, like, for example, serum proteases. The meanings of the terms "hydrolysis" and "(serum) proteases" and the structure of the sites are well known in the art.

In a preferred aspect, in the mutant/variant cyclotides to be used in accordance with the present invention, in particular in the mutant/variant cyclotides more specifically defined herein elsewhere (for example, the mutant/variant cyclotides as defined in items (iv) and (i) to (iii), supra, or items (i) to (xi), infra), none of the (six) Cys residues is replaced by another amino acid residue.

However, with respect to the mutants/variants of the cyclotides, one or more of the (six) Cys residues, in particular the herein defined Cys, may also be replaced by (an)other amino acid(s), as long as the replacement still leads to an individual intramolecular linkage, like that of a disulphide bond, within the cyclopeptide, i.e. to a correct mimicry of the native cyclotide. Such amino acid may, inter alia, be a non-naturally-occurring amino acid, like a non-naturally-occurring amino acid having an —SH group able to form a disulphide bond. However, it is preferred herein that the Cys, in particular the Cys given in formula I, above, is a naturally-occurring amino acid, preferably Cys itself.

It will also be acknowledged by the ones skilled in the art that one or several of the amino acids forming the cyclotide to be employed according to the present invention may be modified. In accordance therewith any amino acid as used/defined herein may also represent its modified form. For example, an alanine residue as used herein may comprise a modified alanine residue. Such modifications may, among others, be a methylation or acylation, or the like, whereby such modification or modified amino acid is preferred as long as the thus modified amino acid and more particularly the cyclotide containing said thus modified amino acid is still functionally active as defined herein. Respective assays for determining whether such a cyclotide, i. e. a cyclotide comprising one or several modified amino acids, fulfils this requirement, are known to the one skilled in the art and, among others, also described herein, particularly in the example part.

The invention also provides the use of derivatives of the disclosed cyclotides such as salts with physiologic organic and anorganic acids like HCl, $H_2SO_4$, $H_3PO_4$, malic acid, fumaric acid, citronic acid, tatratic acid, acetic acid.

It is particularly envisaged that the herein defined cyclotides, and the herein defined mutant cyclotides and variant cyclotides (see, for example, item (iv), supra) have at least one of the desired functions according to this invention, in particular, one of the functions as mentioned in items (i) to (xii) herein below. This/these function(s) make the cyclotides and cyclotide mutants/variants being immunosuppressive cyclotides and immunosuppressive cyclotide mutants/variants in accordance with the present invention.

In one aspect, the cyclotides and cyclotide mutants/variants to be used in accordance with this invention and as defined herein (i) are anti-proliferative cyclotides, i.e. have an (dose-dependent) anti-proliferative effect on (an) immune cell(s), and/or suppress/reduce the effector function(s) of (an) immune cell(s);

(ii) are capable to inhibit, decrease or block immune cell proliferation (without accumulation of dead cells);

(iii) prevent (the onset of) activation and/or proliferation of immune cells;

(iv) lead to an inhibition, decrease or block of proliferating immune cells (without accumulation of dead cells);

(v) are capable of triggering the resting of (viable) immune cells (without accumulation of dead cells);

(vi) have a cytostatic effect on proliferating immune cells, preferably lacking a cytotoxic effect;

(vii) reduce or suppress an over-activity of immune cells;

(viii) are capable to suppress/reduce secretion/production of cytokines, in particular of IL-2, IFN-gamma and/or TNF-alpha;

(ix) are capable to suppress/reduce degranulation/cytotoxicity of PBMCs, in particular of CD107a$^+$ CD8$^+$ PBMCs;
(x) are capable to suppress/reduce expression of IL-2 surface receptor CD25 (on PBMCs);
(xi) are capable to act in a similar manner as Cyclosporine A, Muromonab-CD3 and/or Basiliximab; and/or
(xii) do not induce a change in Ca$^{2+}$ signalling and/or do not induce/increase Ca$^{2+}$ release from (animal) cells.

It is preferred that the herein defined cyclotide functions are fulfilled in the context of a cytostatic administration scheme. In the context of this administration scheme, the cyclotides, in particular kalata B1 or T20K, are capable to function without the accumulation of dead cells, i.e. without a cytotoxic effect. This particularly applies to the cyclotide functions as defined in sections (ii), (iv) and (v), supra.

The skilled person is readily in the position to test whether a given cyclotide or cyclotide mutant/variant can function in accordance with the present invention, e.g. has one or more of the functions defined in sections (i) to (xii), supra. For this purpose, the skilled person may, for example, rely on the assays described in the appended examples (e.g. examples 3 and 5, infra) and on respective assays for anti-proliferative effects as described in the art (Gruendemann, Journal of Ethnopharmacology 136, 3, SI, 2011, 444-451).

By relying on the herein described means and methods and his common general knowledge, the skilled person is also in the position to identify and isolate suitable cyclotides or cyclotide mutants/variants, for example in/from a (plant) extract. Hence, the skilled person is further able to identify and isolate not yet known cyclotides/cyclotide mutants/variants that can be used in accordance with the present invention. The use of such newly identified/isolated cyclotides in accordance with the present invention is also envisaged herein.

In a preferred embodiment, the cyclotide to be used in accordance with the present invention is a (naturally-occurring or native) non-grafted cyclotide, i.e. a cyclotide "per se" without any further (pharmaceutically) active compartments. It is known in the art that cyclotides can act as scaffolds for other (pharmaceutically) active compartments, like other therapeutic peptides (see, for example, Gunasehera, loc. cit.). Such grafted cyclotides, i.e. cyclotides comprising a further (pharmaceutically) active compartment, are less preferred in the context of the present invention. In particular, grafted cyclotides are known to be cyclotides having at least one complete loop between two cysteine residues be replaced by a further (pharmaceutically) active compartment. This is to be seen in contrast to the cyclotides and cyclotide mutants/variants to be preferably used in the context of the present invention. Specifically, these cyclotide mutants/variants are mutated so that no further (pharmaceutically) active compartment is introduced. In principle, it is also possible with respect to these peptide mutants/variants that one or more entire loops between two cysteine residues are replaced by (a stretch of) further amino acid residues, as long as no further (pharmaceutically) active compartment is introduced. The skilled person is readily in the position to distinguish between a grafted cyclotide and a non-grafted cyclotide or a grafted and non-crafted cyclotide mutant/variant.

It is preferred that the immune cells referred to in items (i) to (xii), supra, but also the immune cells referred to herein elsewhere, are primary immune cells.

Furthermore, it is preferred that the immune cells referred to in items (i) to (xii), supra, but also the immune cells referred to herein elsewhere, are activated and/or proliferating immune cells. Also preferred is that the (primary) (activated and/or proliferating) immune cells are of human origin, i.e. are human (primary) (activated and/or proliferating) immune cells. Particular examples of immune cells referred to herein are (primary, activated and/or proliferating) PBMCs and lymphocytes, preferably T-lymphocytes. Again, it is preferred that these PBMCs and (T-)lymphycytes are of human origin, i.e. human PBMCs and human (T-) lymphocytes. In one particular aspect, the PBMCs are CD107a$^+$ CD8$^+$ PBMCs.

In a further aspect, the present invention also relates to the use of a nucleic acid molecule comprising a nucleotide sequence encoding the amino acid backbone/primary amino acid sequence of a cyclotide as disclosed in context of this invention. For example, such nucleic acid molecule may comprise a nucleotide sequence as depicted in any one of SEQ ID NOs. 11, 12, 15 and 16 or a nucleotide sequence as comprised in any one of SEQ ID NOs. 11, 12, 15 and 16 and corresponding to the mature cyclotide or a nucleotide sequence which differs therefrom due to the degeneracy of the genetic code.

The meanings of the terms "nucleic acid molecule(s)", "nucleic acid sequence(s)" and "nucleotide sequence(s)" and the like are well known in the art and are used accordingly in context of the present invention.

For example, when used throughout this invention, these terms refer to all forms of naturally-occurring or recombinantly generated types of nucleotide sequences and/or nucleic acid sequences/molecules as well as to chemically synthesized nucleotide sequences and/or nucleic acid sequences/molecules. These terms also encompass nucleic acid analogues and nucleic acid derivatives such as e.g. locked DNA, PNA, oligonucleotide thiophosphates and substituted ribo-oligonucleotides. Furthermore, these terms also refer to any molecule that comprises nucleotides or nucleotide analogues.

Preferably, the terms "nucleic acid molecule(s)", "nucleic acid sequence(s)" and "nucleotide sequence(s)" and the like refer to deoxyribonucleic acid (DNA) or ribonucleic acid (RNA). The "nucleic acid molecule(s)", "nucleic acid sequence(s)" and "nucleotide sequence(s)" may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Nucleic acid molecule(s)", "nucleic acid sequence(s)" and "nucleotide sequence(s)" also refer to sense and anti-sense DNA and RNA, that is, a nucleotide sequence which is complementary to a specific sequence of nucleotides in DNA and/or RNA.

Furthermore, the terms "nucleic acid molecule(s)", "nucleic acid sequence(s)" and "nucleotide sequence(s)" and the like may refer to DNA or RNA or hybrids thereof or any modification thereof that is known in the state of the art (see, e.g., U.S. Pat. Nos. 5,525,711, 4,711,955, 5,792,608 or EP 302175 for examples of modifications). These molecules of the invention may be single- or double-stranded, linear or circular, natural or synthetic, and without any size limitation. For instance, the "nucleic acid molecule(s)", "nucleic acid sequence(s)" and/or "nucleotide sequence(s)" may be genomic DNA, cDNA, mRNA, antisense RNA, ribozymal or a DNA encoding such RNAs or chimeroplasts (Cole-Strauss Science 1996 273(5280) 1386-9). They may be in the form of a plasmid or of viral DNA or RNA. "Nucleic acid molecule(s)", "nucleic acid sequence(s)" and "nucleotide sequence(s)" and the like may also refer to (an) oligonucleotide(s), wherein any of the state of the art modifications such as phosphothioates or peptide nucleic acids (PNA) are included.

The nucleic acid molecules as provided herein are particularly useful for producing a cyclic peptide of the invention, for example by a corresponding method disclosed herein.

The nucleic acid molecule as disclosed herein and described herein may be comprised in a vector.

Said vector may be a cloning vector or an expression vector, for example, a phage, plasmid, viral or retroviral vector. Retroviral vectors may be replication competent or replication defective. In the latter case, viral propagation generally will occur only in complementing host/cells. The herein disclosed nucleic acid molecule may be joined to a particular vector containing selectable markers for propagation in a host. Generally, a plasmid vector is introduced in a precipitate, such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the disclosed nucleic acid molecule is operatively linked to expression control sequences (e.g. within the herein disclosed vector) allowing expression in prokaryotic or eukaryotic cells or isolated fractions thereof. Expression of said polynucleotide comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogen), pSPORT1 (GIBCO BRL). Preferably, said vector is an expression vector and/or a gene transfer vector. Expression vectors derived from viruses such as retroviruses, adenoviruses, vaccinia virus, adeno-associated virus, herpes viruses, or bovine papilloma virus, may be used for delivery of the polynucleotides or vector of the invention into a targeted cell population. Methods which are well known to those skilled in the art can be used to construct a vector in accordance with this invention; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the disclosed polynucleotides and vectors can be reconstituted into liposomes for delivery to target cells.

The term "isolated fractions thereof" refers to fractions of eukaryotic or prokaryotic cells or tissues which are capable of transcribing or transcribing and translating RNA from the vector. Said fractions comprise proteins which are required for transcription of RNA or transcription of RNA and translation of said RNA into a polypeptide. Said isolated fractions may be, e.g., nuclear and cytoplasmic fractions of eukaryotic cells such as of reticulocytes. Kits for transcribing and translating RNA which encompass the said isolated fractions of cells or tissues are commercially available, e.g., as TNT reticulolysate (Promega).

Again, like the disclosed nucleic acid molecules, also the disclosed vectors are particularly useful for producing a cyclic peptide of the invention, for example by a corresponding method disclosed herein.

In a further aspect, disclosed herein is a recombinant host cell comprising the nucleic acid molecule and/or the vector as disclosed herein. In context of this aspect, the nucleic acid molecule and/or the vector can, inter alia, be used for genetically engineering host cells, e.g., in order to express and isolate the amino acid backbone/primary amino acid sequence of the cyclotides disclosed herein.

Said host cell may be a prokaryotic or eukaryotic cell; see supra. The nucleic acid molecule or vector which is present in the host cell may either be integrated into the genome of the host cell or it may be maintained extra chromosomally.

The host cell can be any prokaryotic or eukaryotic cell, such as a bacterial, insect, fungal, plant, animal, mammalian or, preferably, human cell. Preferred fungal cells are, for example, those of the genus Saccharomyces, in particular those of the species *S. cerevisiae*, or those belonging to the group of hyphal fungi, for example several penicillia or aspergilla strains. The term "prokaryotic" is meant to include all bacteria which can be transformed or transfected with a nucleic acid molecule for the expression of an amino acid backbone/primary amino acid sequence of the cyclotides disclosed herein. Prokaryotic hosts may include gram negative as well as gram positive bacteria such as, for example, *E. coli, S. typhimurium, Serratia marcescens* and *Bacillus subtilis*. A nucleic acid molecule coding for an amino acid backbone/primary amino acid sequence of the cyclic cyclotides disclosed herein can be used to transform or transfect a host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of the above mentioned amino acid backbone/primary amino acid sequence in, for example, prokaryotic hosts.

In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The expressed peptides can then be isolated from the grown medium, cellular lysates, or cellular membrane fractions. The isolation and purification of the microbially or otherwise expressed peptides may be by any conventional means such as, for example, preparative chromatographic separations and immunological separations such as those involving the use of monoclonal or polyclonal antibodies (Ausubel, Current Protocols in Molecular Biology, Green Publishing Associates and Wiley Interscience, N.Y. (1994)).

Again, like the nucleic acid molecules and the vectors as disclosed and described herein, also the corresponding host cells are particularly useful for producing a cyclotide as disclosed herein, for example by the corresponding method disclosed herein.

The skilled person is readily able to provide, i.e. synthesize, the cyclotides to be used in accordance with the present invention or isolate them from, for example, extracts (for example biological extracts like plant, fungal, animal or microbial extracts).

In particular, (bio-)chemically synthesizing approaches or generation of cyclotides via recombination techniques may be employed. For example, a method for producing a cyclotide may comprise the steps of
a) (i) culturing the herein disclosed recombinant host cell under conditions such that the amino acid backbone of the herein disclosed cyclotide is expressed, and recovering said amino acid backbone; or
(ii) chemically synthesizing the amino acid backbone of the herein disclosed cyclotide; and
b) cyclization of said amino acid backbone to form the herein disclosed cyclotide.

As mentioned above, the linear peptides/amino acid backbones of the cyclotides to be produced can also be produced by recombinant engineering techniques. Such techniques are well known in the art (e. g. Sambrook, supra). As also mentioned above, by this kind of production of said linear peptides/amino acid backbones particular advantage can be taken of the herein disclosed and described nucleic acid molecules, vectors and/or host cells. The definitions correspondingly given above apply here, mutatis mutandis.

Several approaches of peptide synthesis particular synthesis approaches of cyclic peptides are known in the art. (e.g. Williams, Chemical Approaches to the Synthesis of Peptides, CRC-Press 1997; Benoiton: Chemistry of Peptide Synthesis. CRC-Press, 2005). The skilled person is readily in the position to apply the prior art knowledge to the particular requirements of the disclosed method for producing cyclic peptides, based on the herein provided teaching.

This invention also relates to the use of a cyclotide obtainable or obtained by the above described approaches or method(s) in accordance with the herein provided disclosure.

Terms like "immunosuppression", "suppression of the immune system" and "suppression/reduction of the activation or efficacy of the immune system" are used herein in a comparable manner. The corresponding meaning is known in the art and the terms are correspondingly used herein. In particular, these terms refer to the suppression or decrease of (a) parameter(s) of the immune system like, for example, (activated and/or proliferating) (an) immune cell(s) as defined herein above.

In accordance with the present invention, (a) parameter(s) of the immune system may be selected from the group consisting of a
(i) immune cells (in particular those defined herein above), in particular PBMCs, more particular lymphocytes, even more particular T-lymphocytes;
(ii) (a) effector function(s) of immune cells (in particular of those defined herein above);
(iii) cytokines, in particular the level, secretion and/or production thereof;
(iv) degranulation/cytotoxicity of immune cells, in particular of CD107a$^+$ CD8$^+$ PBMCs; and
(v) expression of (a) cytokine surface receptor (for example, IL-2 surface receptor CD25), in particular on PBMCs.

Cytokines in accordance with the present invention may be IL-2, IFN-gamma and TNF-alpha, whereby IL-2 is preferred.

"Suppression" or "reduction" in context of the present invention particularly means that the (defence) response of the immune system against a(n) antigen(s)/(a) pathogen(s) is reduced. In the context of the present invention, this is not only to be seen with respect to an activated, i.e. diseased state, of the immune system but also with respect to the non-activated, i.e. normal, healthy state of the immune system. In this context it is clear that even in the normal, healthy state the immune system has a basic level of activation due to the common baseline of antigen/pathogen impact.

Hence, in one embodiment, the "suppression" of the immune system starts from a normal, healthy state of the immune system and, in another embodiment, from an activated, diseased state of the immune system.

In particular, it is envisaged in the context of the present invention that the immune system, in particular one or more parameters thereof, is suppressed/reduced by at least 10%, preferably by at least 20%, more preferably by at least 30%, even more preferably by at least 50%, even more preferably by at least 80%, even more preferably by at least 90%, even more preferably by at least 95%, even more preferably by at least 99% and most preferably 100% of the initial status of the immune system (being either a diseased or a non-diseased status), in particular of one or more parameters thereof. Herein, suppressing/reducing the immune system particularly means suppressing/reducing proliferation of immune cells. The skilled person is readily in the position to test the degree of suppression of the immune system, for example by determining the proliferative activity of immune cells or the fraction of proliferating/activated immune cells. Moreover, the skilled person is readily in the position to determine for a given immunosuppressant/immunosuppressive drug the $IC_{50}$ for the respective immunosuppressive effect/activity.

It is clear to the skilled person that, in accordance with the present invention, the disclosed pharmaceutical composition or cyclotide may be administered in a pharmaceutically/therapeutically effective dose, which means that a pharmaceutically/therapeutically effective amount of the compound administered is reached. Preferably, a pharmaceutically/therapeutically effective dose refers to that amount of the compound administered (active ingredient) that produces amelioration of symptoms or a prolongation of survival of a subject which can be determined by the one skilled in the art doing routine testing.

It is of note that the dosage regimen of the compounds to be administered in accordance with the present invention will be determined by the attending physician and clinical factors. As is well known in the medical arts, that dosages for any one patient depends upon many factors, including the patient's size, body surface area, age, the particular compound to be administered, sex, time and route of administration, general health, and other drugs being administered concurrently. A person skilled in the art is aware of and is able to test the relevant doses, the compounds to be medically applied in accordance with the present invention are to be administered in.

It is particularly envisaged in the context of the present invention that the cyclotide is to be administered so that a cytostatic but little, preferably no, cytotoxic activity/effect occurs.

For this purpose, the cyclotide may, for example, be administered so that a (serum) concentration in the range of 1 to 50 µM, preferably in the range of 1 to 15 µM, more preferably in the range of 3 to 10 µM, more preferably in the range of 4 to 9 µM and even more preferably in the range of 5 to 9 µM is reached. In particular, the cyclotide may be administered via a particular route of administration and/or at an amount/dose to reach a (serum) concentration in the range of 1 to 50 µM, preferably in the range of 1 to 15 µM, more preferably in the range of 3 to 10 µM, more preferably in the range of 4 to 9 µM and even more preferably in the range of 5 to 9 µM.

Further, the cyclotide may, for example, be administered at a dose in the range of 0.1 to 15 mg/kg, preferably in the range of 0.1 to 12 mg/kg, more preferably in the range of 1 to 12 mg/kg, more preferably in the range of 1 to 10 mg/kg, more preferably in the range of 5 to 10 mg/kg, and even more preferably at a dose of about 10 mg/kg.

The dose may be administered on a daily, monthly or, preferably, weekly basis. The cyclotide may be administered in form of 1 or more single doses; in particular, 1, 2, 3, 4 or 5 single doses. The cyclotide may, for example, be administered intravenously or intraperitoneally. Non limiting Examples of particular administration schemes are 3 single intravenous injections of about 10 mg/kg at weekly intervals or a single intraperitoneal dose of about 10 mg/kg. Further possible administration schemes are describe herein below.

The skilled person is readily in the position to find out the particular route of administration and amount/dose of a given cyclotide to be applied in order to reach cytostatic but little/no cytotoxic activity.

In one specific embodiment, the herein described pharmaceutical composition may further comprise one or more additional immunosuppressant(s). Preferably, this (these) additional immunosuppressant(s) is (are) not a part of a grafted form of the cyclotide but is independently comprised in the pharmaceutical composition. In another specific embodiment, the additional immunosuppressant(s) is (are) administered separately. In another specific embodiment, the herein described cyclotide may be administered together with one or more additional immunosuppressant(s), i.e. prior, simultaneously or subsequently with respect to the additional immunosuppressant(s). Non-limiting examples of an additional immunosuppressant may be selected from the group consisting of Cyclosporine A, Muromonab-CD3 (Orthoclone OKT3®) and Basiliximab)(Simulect®).

The herein described pharmaceutical composition may also comprise one or more (anti-immune cell-proliferative) cyclotides. Hence, in a further specific embodiment, the herein described pharmaceutical composition may comprise at least two, three, four or five cyclotides as described herein. In a further specific embodiment, one of the herein described cyclotides is to be administered together with, i.e. prior to, simultaneously with or subsequently to another, different, of the herein described cyclotides.

In one embodiment, the pharmaceutical composition of the present invention may comprise, or be in form of, an (native) extract, in particular a (native) plant extract.

Non-limiting examples of plants from which such an extract may be obtained are *Betula pendula, Oldenlandia affinis*, plants from the Violaceae family (e.g. *Viola* sp., preferably *V. odorata* and *V. tricolor*), Squash species (Cucurbitaceae family), *Ecballium* species, legume species (Fabaceae family) and *Psychotria* species (Rubiaceae family; for example *Psychotria polyphlebia, P. poeppigiana, P. chiapensis, P. borucana, P. buchtienii, P. pillosa, P. mortomiana, P. deflexa, P. makrophylla, P. elata, P. solitudinum, P. capitata*).

As mentioned above, one embodiment of the present invention relates to (a pharmaceutical composition comprising) a cyclotide for use in immune suppression or to a method for immune suppression by administering (a pharmaceutical composition comprising) a cyclotide. In another embodiment, the present invention relates to (a pharmaceutical composition comprising) a cyclotide for use in treating or preventing a disease or disorder and a method of treating or preventing a disease or disorder, said disease or disorder is caused by the activity of the immune system, i.e. a disease or disorder which can be treated, prevented or ameliorated by immunosuppression. In this context, not only the suppression of an over-active immune system to a lower level, for example a normal, non-diseased level, is envisaged, but also the suppression of a normal, healthy-state immune system is envisaged. The latter is, for example, particularly relevant with respect to organ transplantation approaches. The skilled person knows, or at least can test for, particular diseases which can be treated or prevented by suppressing the immune system. Examples of such diseases or disorders are given in Kumar ("Clinical Medicine", $3^{rd}$ edition(1994), Baillière Tindall).

In particular, the disease or disorder to be treated or prevented in accordance with this invention is selected from the group consisting of:
(i) autoimmune disorders;
(ii) hypersensitivity disorders; and
(iii) immune cell-mediated inflammations.

The meaning and scope of "autoimmune disorder", "hypersensitivity disorder" and "immune cell-mediated inflammation" is known in the art and can, for example, be deduced from Kumar ("Clinical Medicine", $3^{rd}$ edition, 1994, Baillière Tindall).

Particular examples of autoimmune disorders to be treated or prevented are selected from the group consisting of:
(i) Multiple Sclerosis;
(ii) Psoriasis;
(iii) Systemic Lupus Erythematosus;
(iv) Sjögren's syndrome;
(v) Rheumatoid Arthritis (RA), in particular severe RA;
(vi) Idiopathic Thrombocytopenic Purpura;
(vii) Diabetes;
(viii) Vasculitis; and
(ix) Crohn's disease.

Particular examples of hypersensitivity disorders to be treated or prevented are graft-versus-host disorders and Contact Dermatitis.

A particular example of an immune cell-mediated inflammation is a lymphocyte-mediated inflammation, in particular a T-cell-mediated inflammation. Particular examples of lymphocyte-mediated inflammations to be treated or prevented are Keratoconjunctivitis sicca and Dry Eye Syndrome (DES). Corneal clarity is required for optimal vision and can be affected severely by any form of corneal inflammation. This is mediated by infiltrating leukocytes and pathological blood vessel formation in the long-run. In general, any occurring corneal inflammation is to be treated especially if the central cornea is involved. Once a corneal scar established, keratoplasty becomes necessary to restore corneal transparency that is indispensable for optimal vision.

In one embodiment, it is particularly envisaged that diseases or disorders of a sub-group of the above (or herein elsewhere) defined diseases or disorders are to be treated/prevented, said sub-group of diseases or disorders comprises those diseases or disorders which (i) come along with and/or are caused by an (over-)activated immune system and/or (over-)activated/increased parameter(s) of the immune system or
(ii) which can be treated/prevented by suppressing the immune system (starting from an (over-)activated, diseased state or from a normal, healthy state). Within this sub-group, particularly those diseases/disorders are to be treated/prevented which come along with and/or are caused by (over-)activated immune cells or which can be treated/prevented by reducing the (proliferating) activity of immune cells.

What has been said with respect to the meaning of "immune cells" and "parameter(s) of the immune system" herein elsewhere also applies here, mutatis mutandis.

In another embodiment, immune cells, in particular proliferation of the same, are/is to be suppressed in the context of the treatment/prevention of this invention. Preferably, such immune cells are (primary) activated (T-)lymphocytes and/or peripheral blood mononuclear cells (PBMC). Again, what has been said with respect to the meaning of "immune cells" herein elsewhere also applies here mutatis mutandis.

In another embodiment, (a) parameter(s) of the immune system are/is to be suppressed/reduced in the context of the treatment/prevention of this invention. What has been said with respect to the meaning of "parameter(s) of the immune system" herein elsewhere also applies here, mutatis mutandis.

In one specific aspect, the disease or disorder to be treated/prevented in accordance with this invention is a disease or disorder mediated by a cytokine pathway, in particular the IL-2 pathway (via CD25).

In another specific aspect, the disease or disorder to be treated/prevented is a disease or disorder
(i) which cannot be treated or is not to be treated by an induction or increase of $Ca^{2+}$ release; and/or
(ii) which does not come along or is not related to a change in $Ca^{2+}$ signalling.

In another specific embodiment, the disease to be treated/prevented is not a disease that can be treated/prevented by inhibiting the activity of tryptase, i.e. is a tryptase-independent disease or disorder.

Each or more of the above embodiments/aspects particularly applies/apply to the above (or herein elsewhere) defined or exemplified diseases or disorders, in particular to the diseases or disorders as defined or exemplified in sections (i) to (iii) or (i) to (ix), supra. More particular, each or more of the above embodiments/aspects applies/apply to a sub-group of these diseases or disorders.

Beside their amino acid backbone, the cyclotides to be used in accordance with the invention may further comprise (e.g. have covalently bound) (a) further substituent(s), like labels, anchors (like proteinaceous membrane anchors), tags (like HIS tags). The substituent(s) can be bound covalently or non-covalently to the cyclotides and directly or via linkers. The skilled person is readily in the position to find out appropriate linkers to be employed in this context. Moreover, appropriate substituents and methods for adding them to a cyclotide are known to those of ordinary skill in the art.

Examples of labels include, inter alia, fluorochromes (like fluorine-18, fluorescein, rhodamine, Texas Red, etc.), enzymes (like horse radish peroxidase, β-galactosidase, alkaline phosphatase), radio/radioactive isotopes (like 32P, 33P, 35S, 125I or 123I, 135I, 124I, 11C, 15O), biotin, digoxygenin, colloidal metals, chemi- or bioluminescent compounds (like dioxetanes, luminol or acridiniums). One non-limiting example of a label that may be bound to the cyclotide is a fluorochrome, like a FRET fluorochrome, for example a GFP, YFP or CFP variant (e.g. GFP, YFP, CFP, eGFP, EYFP or ECFP). A variety of techniques are available for labeling biomolecules, and comprise, inter alia, covalent coupling of enzymes or biotinyl groups, phosphorylations, biotinylations, random priming, nick-translations, tailing (using terminal transferases). Such techniques are, e.g., described in Tijssen, "Practice and theory of enzyme immunoassays", Burden and von Knippenburg (Eds), Volume 15 (1985); "Basic methods in molecular biology", Davis L G, Dibmer M D, Battey Elsevier (1990); Mayer, (Eds) "Immunochemical methods in cell and molecular biology" Academic Press, London (1987); or in the series "Methods in Enzymology", Academic Press, Inc. Corresponding detection methods comprise, but are not limited to, autoradiography, fluorescence microscopy, direct and indirect enzymatic reactions, etc.

The cyclotides as described and defined herein, in particular the above-described labelled cyclotides may be employed in biodistribution studies, i.e. studies resulting in a pattern of distribution of the cyclotide, for example in an animal or, preferably a human subject/patient. For example, such biodistribution studies may comprise imaging by single-photon or PET imaging devices.

Administration of the pharmaceutical composition or the cyclotide(s) in accordance with this invention may be effected by different ways. Such may be, for example, oral, intravenous, intraarterial, intraperitoneal, intravesical or subcutaneous administrations or administration by inhalation as well as transdermal administration. Other examples are parenteral, such as subcutaneous, intravenous, intramuscular, intraperitoneal, intrathecal, transdermal, transmucosal, transpulmonal subdural administrations, local or topical administrations and administrations via iontophoresis, sublingual administrations, administrations by inhalation spray or aerosol or rectal administrations, and the like.

In particular, for patients and/or for particular medical uses, particular administration routes like blood infusion (e.g. intravenous infusion), rectal administration (e.g. in form of enemas or suppositories) or topical administration routes (in particular when eye diseases like the dry eye syndrome are to be treated) may be indicated.

A carrier optionally comprised in the pharmaceutical composition of the invention or to be administered together with the pharmaceutical composition or the cyclotide of the invention may particularly be a pharmaceutically acceptable carrier, excipient or diluent.

Such carriers are well known in the art. The skilled person is readily in the position to find out such carriers which are particularly suitable to be employed in accordance with the present invention.

Pharmaceutically acceptable carriers/excipients that may be used in the formulation of the pharmaceutical compositions comprising the active compounds as defined herein (or a salt thereof) may generally comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-R-cyclodextrin, polyvinylpyrrolidone, low melting waxes, ion exchange resins. Other suitable pharmaceutically acceptable carriers/excipients are described in Remington's Pharmaceutical Sciences, 15$^{th}$ Ed., Mack Publishing Co., New Jersey (1991). In the following, several non-limiting administration schemes and the use of correspondingly suitable pharmaceutically acceptable carrier are described.

For an administration of the pharmaceutical composition or the cyclotides in accordance with this invention via subcutaneous (s.c.) or intravenous (i.v.)/intraarterial (i.a.) injection, cyclotides (or encoding sequences) may be formulated in aqueous solution, preferably in physiologically compatible buffers such as Hank's solution, Ringer's solution, or physiologically saline buffer. For transmucosal and transpulmonal administration, penetrants appropriate to the barrier to be permeated are used in the formulation. Such penetrants are generally known in the art.

The use of pharmaceutical acceptable carriers to formulate the cyclotides into dosages or pharmaceutical compositions suitable for systemic, i.e. intravenous/intraarterial, or subcutaneous administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for subcutaneous or oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention, or medicaments or pharmaceutical compositions comprising them, intended to be administered intracorporally/intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered near the cell surface. Delivery systems involving liposomes are disclosed in U.S. Pat. No. 4,880,635 to Janoff et al. The publications and patents provide useful descriptions of techniques for liposome drug delivery.

Pharmaceutical compositions comprising a compound according to the present invention for parenteral and/or subcutaneous administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injections suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions and to allow for a constantly slow release of the substance in the organism.

A "patient"/"subject" for the purposes of the present invention, i. e. to whom a pharmaceutical composition or cyclotide according to the present invention is to be administered or who suffers from the disease a disorder as defined and described herein, includes both humans and animals and other organisms. Thus the compositions and methods of this invention are applicable to or in connection with both, human therapy and veterinary applications including treating/preventing procedures and methods. In the preferred embodiment the patient/subject is a mammal, and in the most preferred embodiment the patient/subject is human.

The present invention further relates to a method of screening for and/or selecting an immunosuppressive cyclotide comprising the step of i) contacting a cyclotide or a (plant) extract containing a cyclotide with (a sample of) an (activated) cell of the immune system and determining the proliferative activity of said cell,
wherein a suppressed or reduced proliferative activity (as compared to a control) is indicative for the immunosuppressive activity of the cyclotide; or ii) administering to an animal model a pharmaceutically effective amount of a cyclotide or a (plant) extract containing a cyclotide and determining ((a) parameter(s) of) the immune system or (a) clinical sign(s)/the presence of a disease or disorder as defined herein,
wherein the suppression or reduction of (the parameter(s) of) the immune system or the decrease of the clinical sign(s)/amelioration of the disease or disorder (as compared to a control) is indicative for the immunosuppressive activity of the cyclotide.

The method of screening for and/or selecting may further comprise the step of isolating and/or identifying the immunosuppressive cyclotide (from/in the (plant) extract). For example, said step of isolating and/or identifying may comprise (nano) LC-MS/MS or LC-MS reconstruction, preferably a combination of both, (nano) LC-MS/MS and LC-MS reconstruction. Optionally, said step may further comprise (automated) database searching and/or manual de novo peptide sequencing by assigning b- and y-fragment ions from MS/MS spectra.

Moreover, the method of screening for and/or selecting may further comprise a step of determining the biodistribution pattern of the (isolated and/or identified) immunosuppressive cyclotide in (a sample of) a human or animal subject. Examples of corresponding biodistribution techniques are described herein above.

A suitable control as to the herein disclosed method of screening for and/or selecting an immunosuppressive cyclotide may be (a sample of) an (activated) cell of the immune system that (i) has not been contacted with the cyclotide or the (plant) extract containing a cyclotide; or (ii) has been contacted with a cyclotide not having immunosuppressive activity.

Another suitable control as to the herein disclosed method of screening for and/or selecting an immunosuppressive cyclotide may be an animal model to which (i) no such cyclotide or (plant) extract containing a cyclotide has been administered; or
(ii) a cyclotide not having immunosuppressive activity has been administered (at a comparable or the same amount).

The present invention further relates to a method of screening for and/or selecting a mutation which, when introduced into a cyclotide, results in a mutated cyclotide having an induced or enhanced immunosuppressive activity as compared to the non-mutated cyclotide, said method comprising the steps of (i) introducing a mutation into a cyclotide; and
(ii) contacting the so mutated cyclotide with (a sample of) an (activated) cell of the immune system and determining the proliferative activity of said cell, wherein a reduced proliferative activity as compared to a control indicates that the mutation confers (enhanced) immunosuppressive activity to the cyclotide; or administering to an animal model a pharmaceutically effective amount of the so mutated cyclotide and determining ((a) parameter(s) of) the immune system or (a) clinical sign(s)/the presence of a disease or disorder as defined herein, wherein the suppression or reduction of (the parameter(s) of) the immune system or the decrease of the clinical sign(s)/amelioration of the condition/disorder as compared to a control indicates that the mutation confers (enhanced) immunosuppressive activity to the cyclotide.

A suitable control as to the herein disclosed method of screening for and/or selecting a mutation may be (a sample of) an (activated) cell of the immune system that (i) has not been contacted with the mutated cyclotide; or (ii) has been contacted with the non-mutated form of the cyclotide or with a cyclotide not having immunosuppressive activity.

Another suitable control as to the herein disclosed method of screening for and/or selecting a mutation may be an animal model to which (i) no such mutated cyclotide has been administered; or (ii) the non-mutated form of the cyclotide or a cyclotide not having immunosuppressive activity has been administered Non-limiting examples of cyclotides not having immunosuppressive activity are selected from the group consisting of the Kalata B1 mutants T8K, V10A and V10K as disclosed herein.

Suppression or reduction of the proliferative activity, (the parameter(s) of) the immune system or the decrease of the clinical sign(s)/amelioration of the condition/disorder as compared to a control preferably means a suppression or reduction by at least 20%, more preferably by at least 30%, more preferably by at least 40%, more preferably by at least 50%, more preferably by at least 60%, more preferably by at least 70%, more preferably by at least 80%, more preferably by at least 90% and more preferably by at least 95% as compared to a control.

The present invention further relates to a method of producing an immunosuppressive cyclotide comprising the step of introducing a mutation screened for and/or selected according to the above method into a cyclotide.

In general, "mutation" in the context of the present invention means any change in the structure of the (native or wildtype) cyclotide, in particular in the primary amino acid sequence thereof. More particular, "mutation" means that one or more amino acid residues of the (native or wildtype) cyclotide are replaced, substituted or added. In one specific aspect, "mutation" refers to a point mutation, i.e. to the replacement, substitution or addition of one amino acid residue. In a more specific aspect, "mutation" refers to the replacement of one amino acid residue. What has been said with respect to the mutated/variant forms to be used in accordance with the present invention herein elsewhere also applies to the meaning of the term "mutation", mutatis mutandis.

If not specified differently, "induction", "induce" or "induced" in the context of this invention means starting from a baseline which is virtually zero. "Increase"/"increased" or "enhance"/"enhanced" not necessarily means starting from a baseline which is virtually zero but may also mean starting from a level which is already above zero. For example, an induced immunosuppressive activity is meant, when there initially was no immunosuppressive activity at all; an enhanced/increased immunosuppressive activity is meant, when there initially was already some immunosuppressive activity which is then further enhanced/increased.

A preferred animal model to be applied in the context of the herein disclosed method of screening for and/or selecting is an animal model for any one of the diseases or disorders as defined herein. Corresponding animal models are known in the art. For example, such an animal model may be an animal model for an autoimmune disease, like, for example, MS. A non-limiting example for an MS animal model is an EAE animal model, for example an EAE mouse model. Another example of an animal model which may be applied in this context is a (mouse, rat, and the like) model for dry eye syndrome (DES), like, for example, a model for DES using Fisher and/or Lewis rats.

The use of such animal models in the context of the screening/selection methods of the invention is described in more detail in the following non-limiting example. Corneal clarity is required for optimal vision and can be affected severely by any form of corneal inflammation. This is mediated by infiltrating leukocytes and pathological blood vessel formation in the long-run. Independently of the reasons, any occurring corneal inflammation has to be treated especially if the central cornea is involved. Once a corneal scar established, keratoplasty becomes necessary to restore corneal transparency that is indispensable for optimal vision. Orthotopic corneal transplantation may be performed between Fisher and Lewis rats. Recipient rats may either be treated with a control or the component (i.e. cyclotide) of interest. The therapy may be administered intraperitoneally (or another method described above) for, for example, 14 days. All treatments may be controlled in a syngeneic setting. Corneal grafts may be fixed with eight interrupted sutures and protected by a blepharorraphy for the initial 3 days after transplantation. After removal of the blepharorraphy, the grafts may be examined by two independent investigators for signs of opacity, vascularization, and edema according to an internationally accepted score. Opacification of the graft may be scored as follows: 0=no opacity; 1=slight opacity, details of iris clearly visible; 2=moderate opacity, some details of iris no longer visible; 3=strong opacity, pupil still recognizable; 4=total opacity. Rejection may be defined as complete graft opacification (grade 4). Additionally, all animals may be monitored daily for signs of toxic side effects, such as weight loss. Rats may be sacrificed for histological characterization of the leukocytic infiltrate in the graft. Additionally, draining and non-draining submandibular lymph nodes as well as spleen may be prepared for flow cytometric analysis of T lymphocytes activation and T cell apoptosis. Finally, the systemically induced strength of the T cell response may be determined by a mixed-leukocyte reaction in both lymph nodes mentioned.

The skilled person is readily in the position to apply and adapt the described exemplified use of an DES model also to other animal models of any one of the diseases or disorders as defined herein.

In one specific aspect, (a sample of) a (activated) cell of the immune system may be seen as an "animal model" in accordance with the present invention.

It is particularly envisaged that the cyclotide to be screened/selected is a cyclotide as defined herein. The respective definitions apply here mutatis mutandis.

In the context of the herein disclosed methods of screening/selecting, the (activated) cell or the parameter of the immune system may be an immune cell or parameter of the immune system as defined and described herein elsewhere. The respective definitions also apply here, mutatis mutandis.

A suitable "sample" in accordance with the present invention includes, but is not limited to, (a) biological or medical sample(s), like, e.g. (a) sample(s) comprising cell(s) or tissue(s). For example, such (a) sample(s) may comprise(s) biological material of biopsies. The meaning of "biopsies" is known in the art. For instance, biopsies comprise cell(s) or tissue(s) taken, e. g. by the attending physician, from a patient/subject as described herein. Exemplarily, but not limiting, the biological or medical sample to be analysed in context of the present invention is or is derived from blood, plasma, white blood cells, urine, semen, sputum, cerebrospinal fluid, lymph or lymphatic tissues or cells, muscle cells, heart cells, cells from veins or arteries, nerve cells, cells from spinal cord, brain cells, liver cells, kidney cells, cells from the intestinal tract, cells from the testis, cells from the urogenital tract, colon cells, skin, bone, bone marrow, placenta, amniotic fluid, hair, hair and/or follicles, stem cells (embryonic, neuronal, and/or others) or primary or immortalized cell lines (lymphocytes, macrophages, or cell lines). Preferred "samples" in accordance with the present invention are those derived from blood or plasma. The biological or medical sample as defined herein may also be or be derived from biopsies, for example biopsies derived from heart tissue, veins or arteries.

In one aspect of the pharmaceutical composition or methods of this invention, the anti-proliferative effect or suppression/reduction is mediated in a cytokine-depending manner, for example in an IL-2-, IFN-gamma- and/or TNF-alpha-depending manner, and/or can be antagonized by a cytokine, for example by IL-2.

The present invention further relates to a method of producing an immunosuppressive pharmaceutical composition comprising the step of mixing
(i) a cyclotide as defined herein; or
(ii) a cyclotide screened for, selected, produced, isolated or identified as described herein
with a pharmaceutically acceptable carrier.

The present invention further relates to a mutated cyclotide having immunosuppressive activity and, in particular, to a mutated cyclotide as defined and described herein (for example a mutated cyclotide comprising an amino acid sequence selected from the group consisting of SEQ ID NOs: 3 to 7 or a cyclotide consisting of a head-to-tail cyclized form of an amino acid sequence selected from the group consisting of SEQ ID NOs: 3 to 7.

Furthermore, the present invention related to a pharmaceutical composition comprising a mutated cyclotide having immunosuppressive activity and optionally a pharmaceutically acceptable carrier, excipient or diluent. Also in this context, it is particularly envisaged that the mutated cyclotide is a mutated cyclotide as defined herein above.

The present invention is further described by reference to the following non-limiting figures and examples.

The Figures show:

FIG. 1. Structure and sequence diversity of cyclotides. The structure of the typical cyclotide kalata B1 is shown in black cartoon. The six conserved cysteines are labeled with roman numerals and the resulting cysteine-knot disulfide connectivity ($C_I$-$C_{IV}$, $C_{II}$-$C_V$ and $C_{III}$-$C_{VI}$) is shown. The amino acid sequence and disulfide connectivity of kalata B1 is shown below the structure cartoon. The numbers (n) indicate the possible length (in amino acids) of the inter-cysteine loops comprising all currently known cyclotides (according to Ireland et al. (Ireland, 2010, J Nat Prod, 73, 1610-1622)). The inter-cysteine loops can tolerate a wide variety of amino acid substitutions and are an indicator of the combinatorial diversity of the cyclotide scaffold. The positions of synthetic mutations that have been introduced during this study are indicated by amino acid one-letter code, number and asterisk. The natural point of cyclysation is indicated by an arrow.

Figure 2:
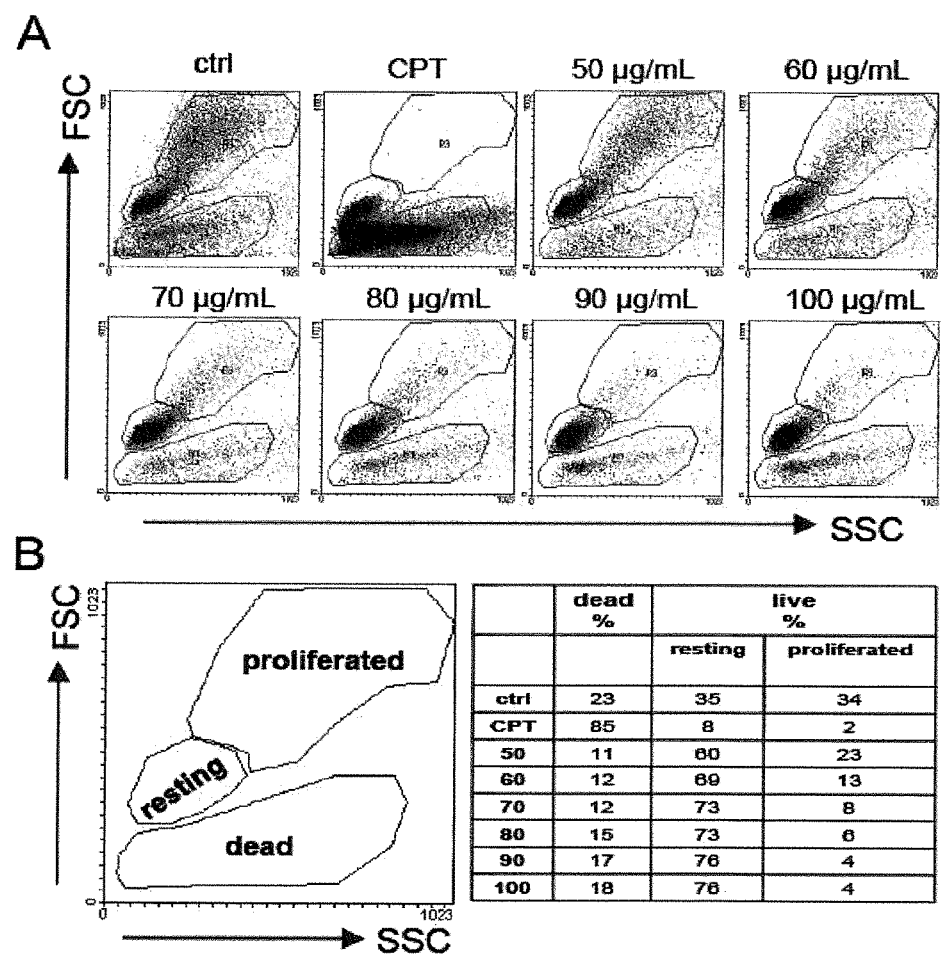
Figure 2:
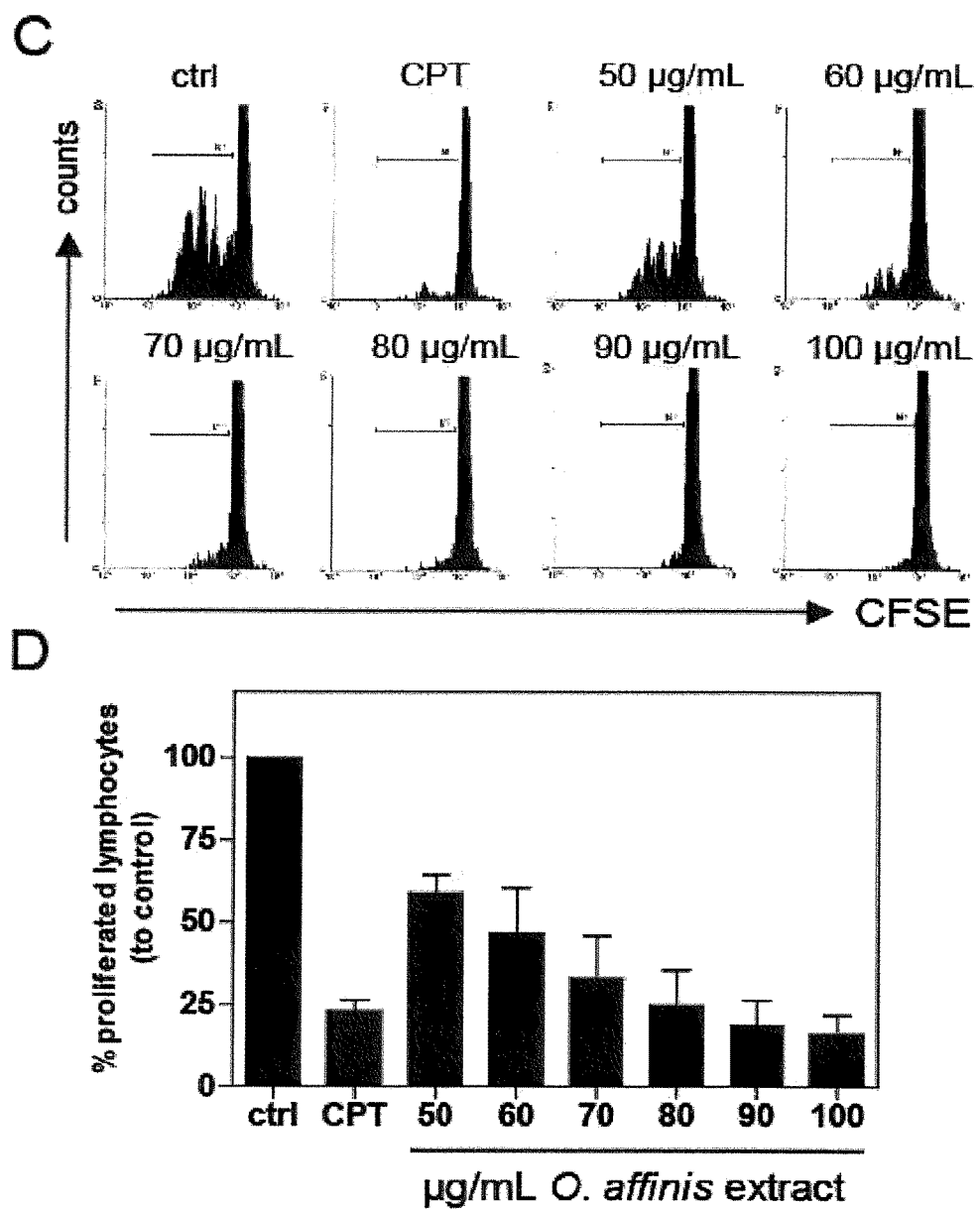

FIG. 2. Effects of the *O. affinis* cyclotide extract on cell proliferation of activated human peripheral blood mononuclear cells. CFSE-labelled primary human PBMC were antibody-activated (anti-CD3/CD28 mAbs) and cultured in the presence of medium (ctrl), camptothecin (CPT, 30 μg/mL) or different concentrations (50-100 μg/mL) of *O. affinis* cyclotide extract. The cells were further analyzed for cell viability and proliferation capacity using flow forward-side-scatter-based flow cytometric analysis (A and B). Cell division analysis were assessed by FACS and illustrated as representative dot plots (C). Results are summarized from three independent experiments in (D) and data are presented as mean±SEM.

Figure 3:
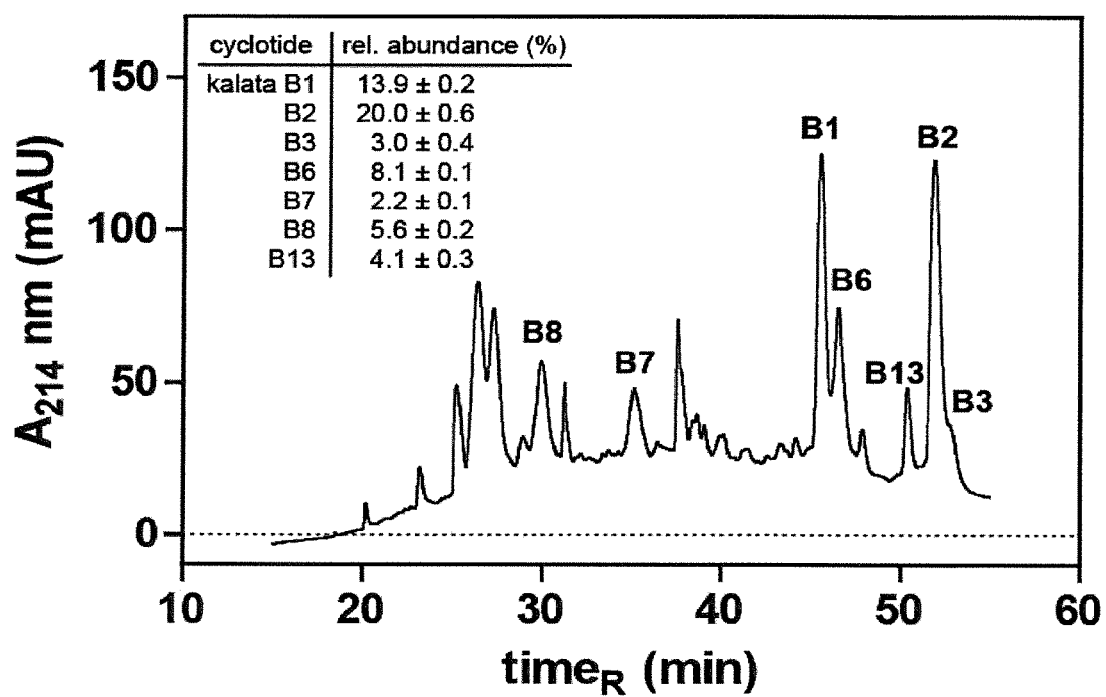

FIG. 3. Nano LC-MS chromatogram of *O. affinis* cyclotides. The nanoflow elution profile of cyclotides from *O. affinis* was monitored with UV absorbance at 214 nm and mass spectrometry. The HPLC graph of a representative crude cyclotide extract is shown and its major cyclotides are indicated by name and relative abundance. The relative cyclotide content (mean±SEM) was determined by peak integration of five independent experiments (see Table 6). HPLC and MS conditions for cyclotide analysis are shown in the Methods Section.

Figure 4:
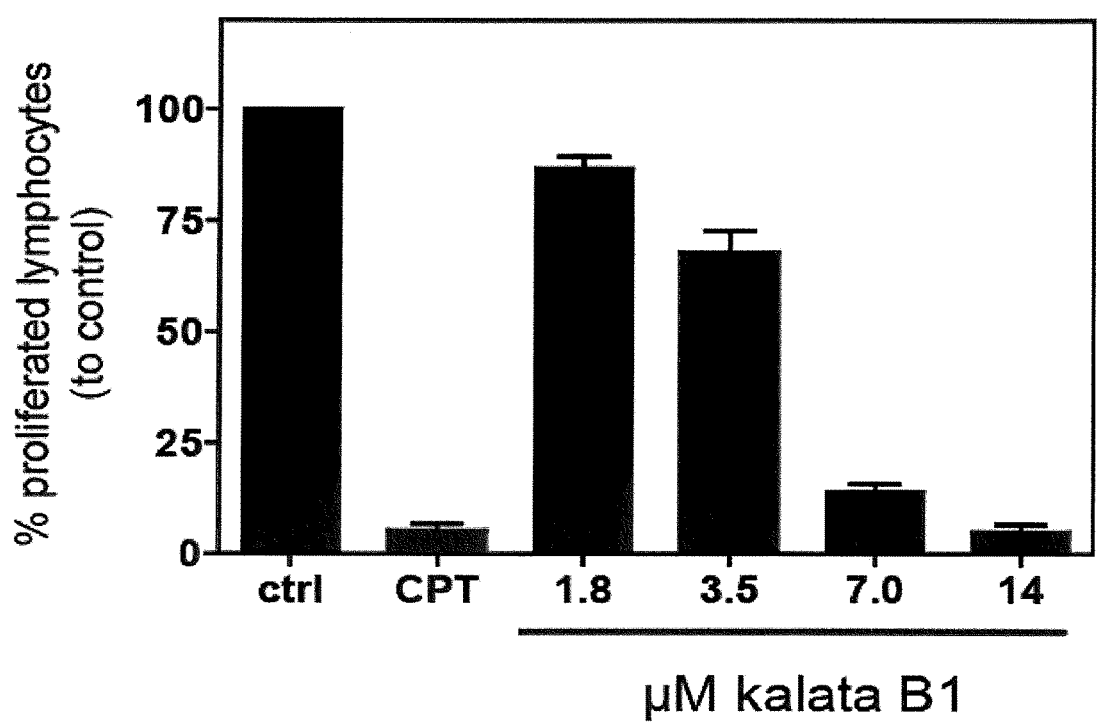

FIG. 4. Effects of kalata B1 on cell proliferation of activated human peripheral blood mononuclear cells. The influence of medium (ctrl), camptothecin (CPT, 30 μg/mL) or different concentrations of kalata B1 (1.8-14 μM) on proliferation of CFSE$^+$ anti-CD3/CD28 mAbs-activated human primary PBMC was measured by cell division analysis using flow cytometry. Data are presented as mean±SEM of four independent experiments.

Figure 5:
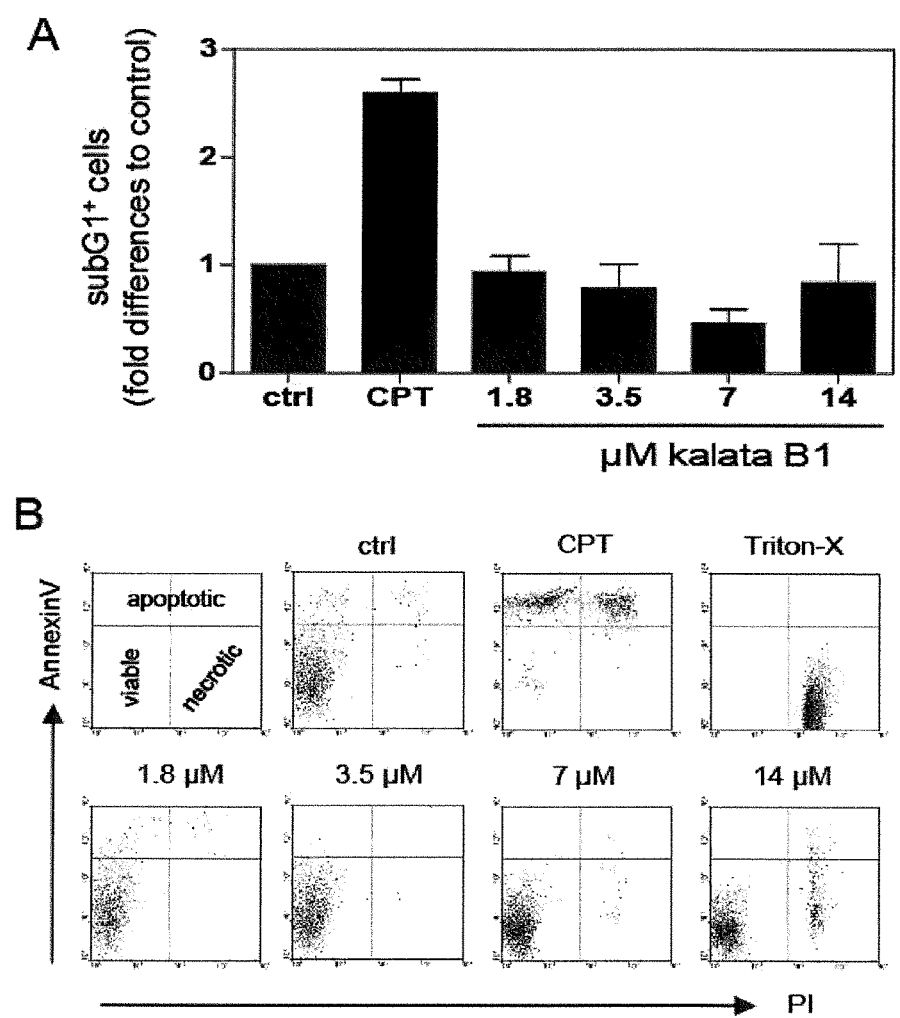
Figure 5:
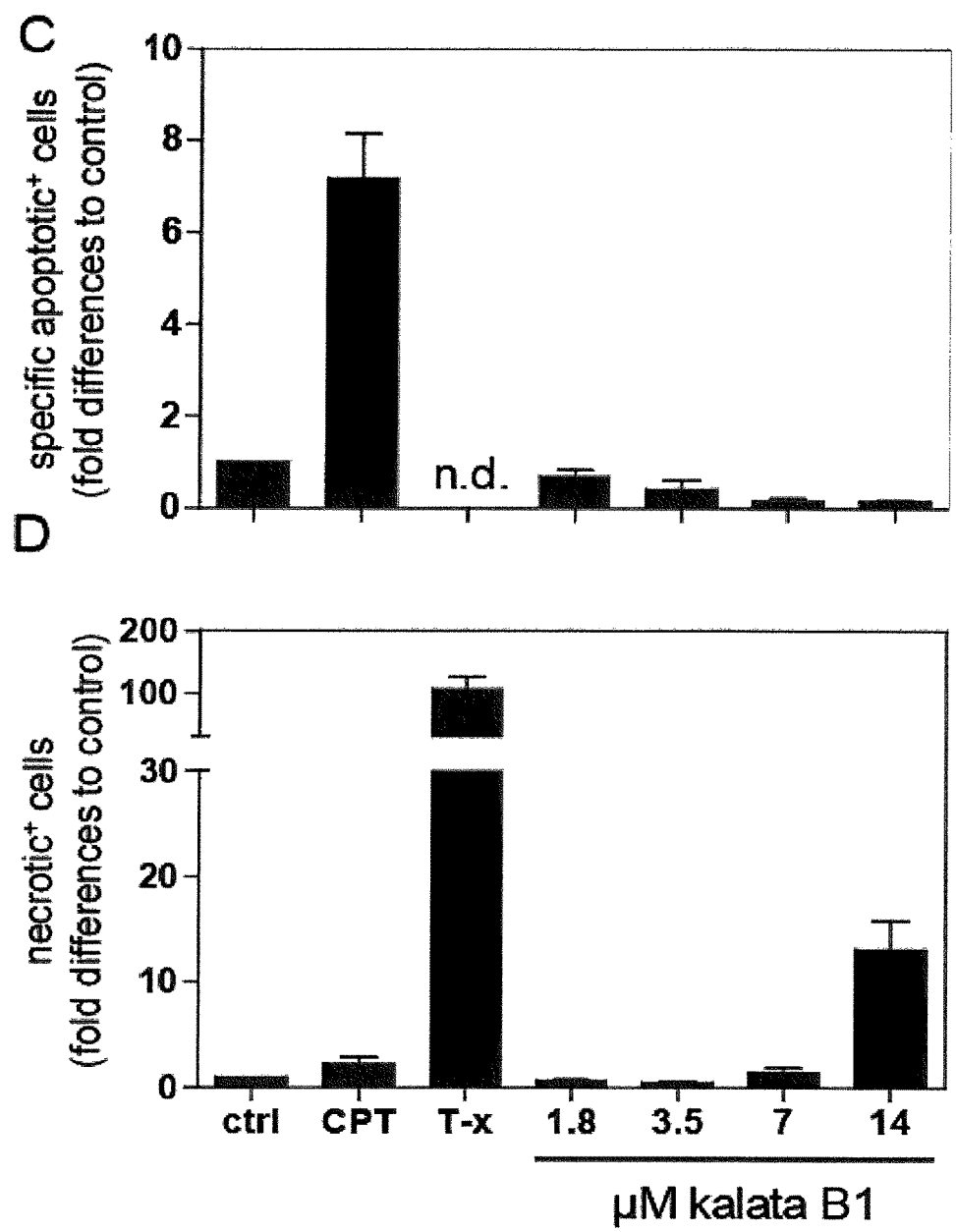

FIG. 5. Effects of kalata B1 on cytotoxicity of activated human peripheral blood mononuclear cells. Human primary PBMC were activated with anti-CD3/CD28 mAbs in the presence of medium (ctrl), camptothecin (CPT, 30 μg/mL), Triton-X 100 (T-x) or different concentrations of kalata B1 (1.8-14 μM) and analyzed for "subG1" DNA content (A) by flow cytometry. Cells were stained with annexin V and propidium iodide (PI) to assess the percentages of viable (annexin V$^-$/PI$^-$), apoptotic (annexin V$^+$/PI$^-$ or annexin V$^+$/PI$^+$) and necrotic (annexin V$^-$/PI$^+$) cells. Dot plots were analyzed and representative graphs are shown in (B). Results from three independent experiments are summarized and data are presented as mean±SEM (C and D). n.d.=not detectable.

Figure 6:
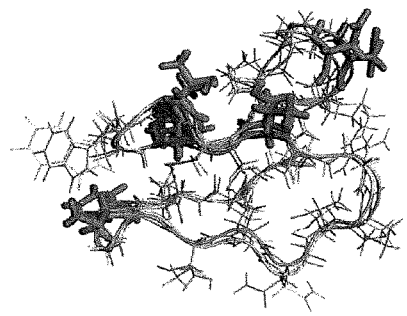
Figure 6:
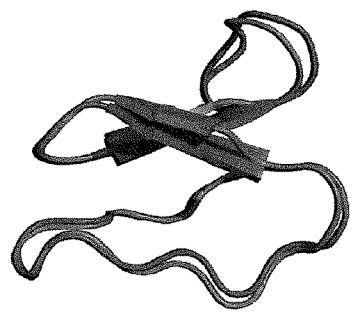

FIG. 6. Structural alignment of kalata B1 and B2. The NMR solution structures of kalata B1 (PDB code: 1NB1) and kalata B2 (1 PT4) were structurally aligned using PyMol. Alignment of all atoms (A) results in an RMSD of 0.725 Å (only the five differing residues are highlighted in bold stick mode, the remaining residues are shown with thin lines) and the backbone atoms (B) fit to a RMSD of 0.599 Å. The sequences of both cyclotides are shown below the aligned structures with differing residues indicated by black boxes.

Figure 7:
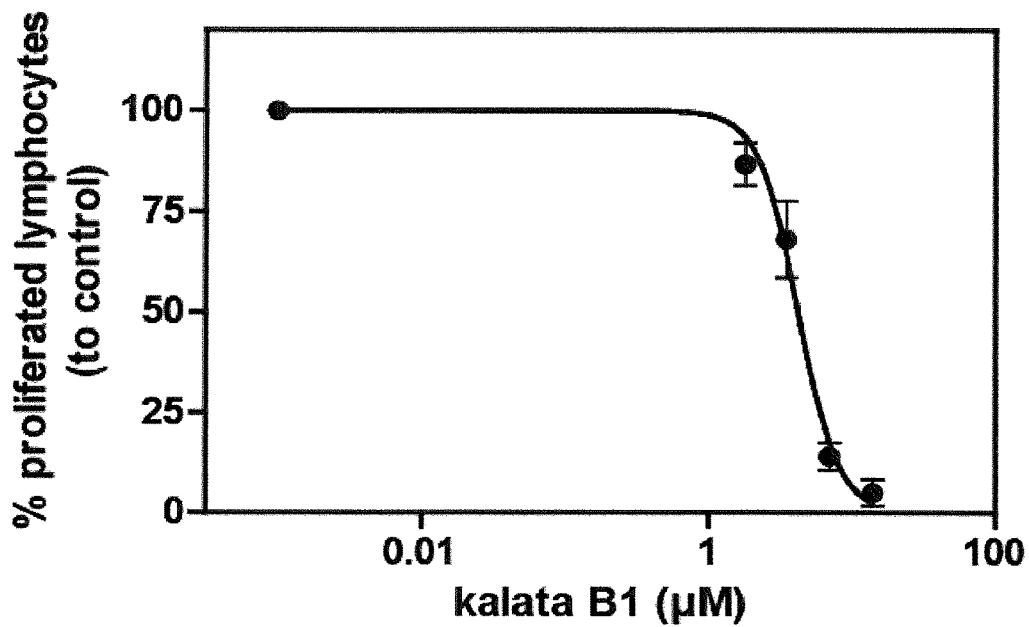

FIG. 7. Determination of $IC_{50}$ for anti-proliferative effect of kalata B1 on PBMC. The IC50 of the anti-proliferative effects of kalata B1 (see FIG. 4) has been determined by non-linear regression analysis (log inhibitor vs. normalized response) using GraphPad Prism.

Figure 8:
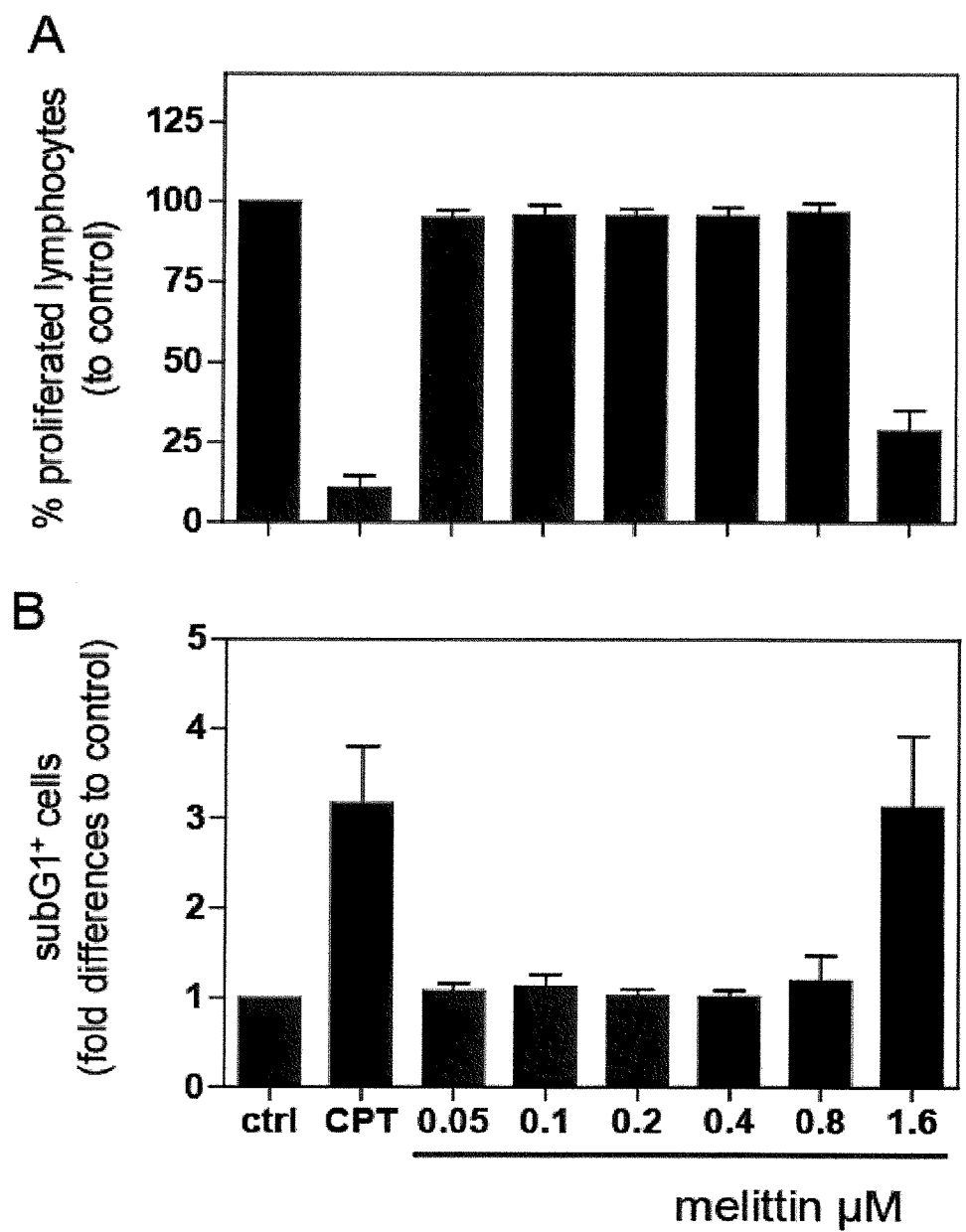
Figure 8:
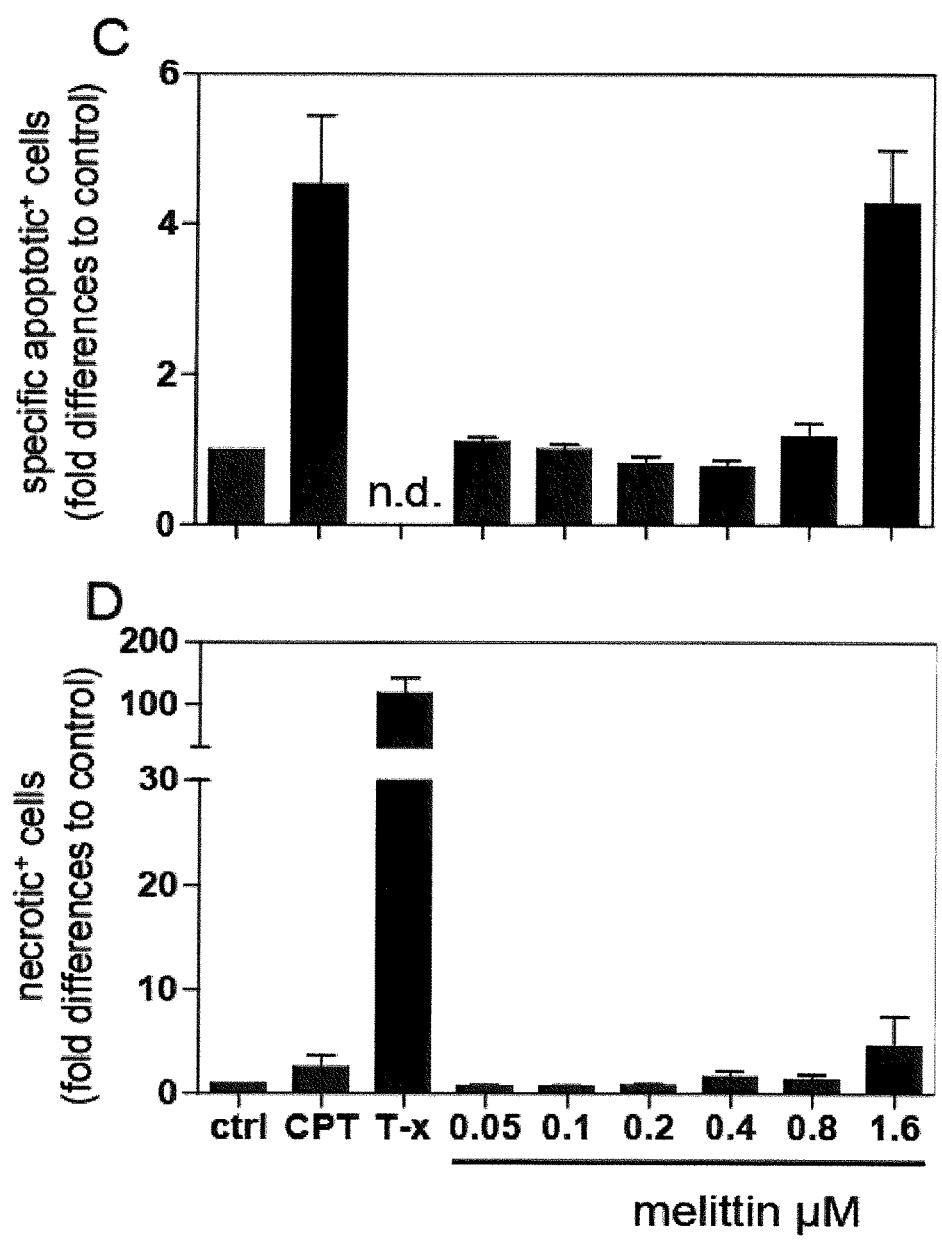

FIG. 8. Effects of melittin on cell proliferation and cytotoxicity of activated human peripheral blood mononuclear cells. Antibody (anti-CD3/CD28 mAbs)-activated human primary lymphocytes were cultured in the presence of medium (ctrl), camptothecin (CPT, 30 µg/mL), Triton-X 100 (T-x) or different concentrations of melittin (0.05-1.6 µM) for flow cytometric analysis of cell division (A), "subG1" DNA content (B) or apoptotic (C) and necrotic (D) cell content. For apoptotic and necrotic detection cells were stained with annexin V and propidium iodide to assess the percentages of viable (annexin V−/PI−), apoptotic (annexin V+/PI− or annexin V+/PI+) and necrotic (annexin V−/PI+) cells. Data are presented as mean±SEM of three to four independent experiments. n.d.=not detectable.

Figure 9:
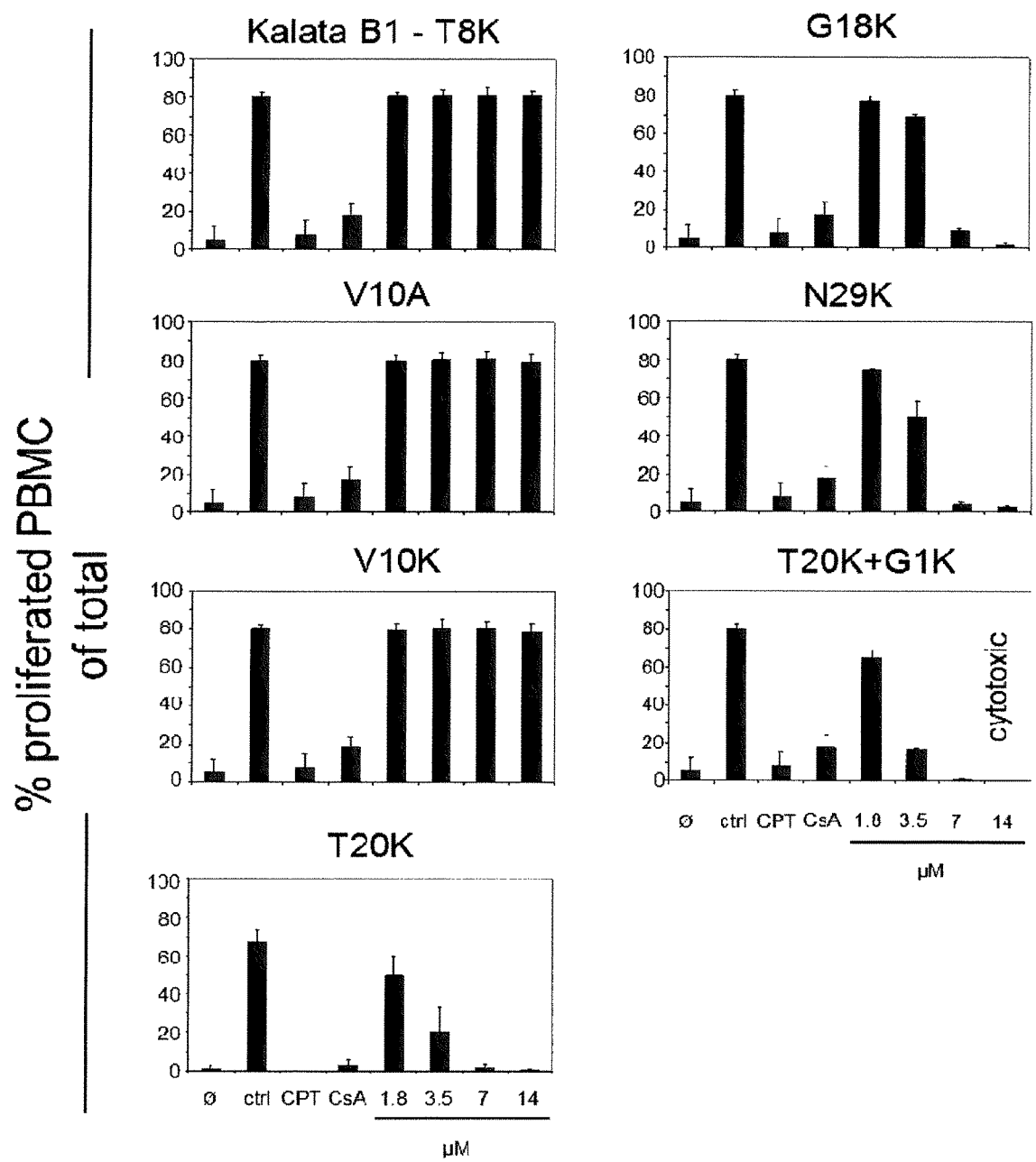

FIG. 9. Effects of cyclotide mutants on cell proliferation of activated human peripheral blood mononuclear cells (PBMC). The influence of non-activated (∅), medium (ctrl), camptothecin (CPT, 30 µM), cyclosporin A (CsA, 1 µg/mL) or different concentrations of cyclotides (1.8-14 µM) on proliferation of CFSE+ anti-CD3/CD28 (each 100 ng/mL) mAbs-activated human primary PBMC was measured by cell division analysis using flow cytometry. Data are presented as mean+SD of at least two independent donors and experiments. Cyclotide mutants G18K, N29K and T20K show anti-proliferative capacity. T20K+G1K is cytotoxic at 14 µM. Controls are similar in each bar diagram. Results with CD3-purified cells are in agreement with those data (see Table 2).

Figure 10:
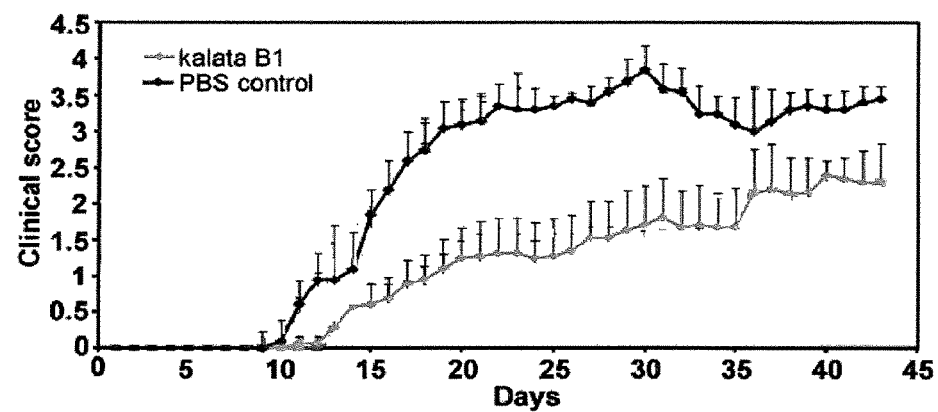
Figure 10:
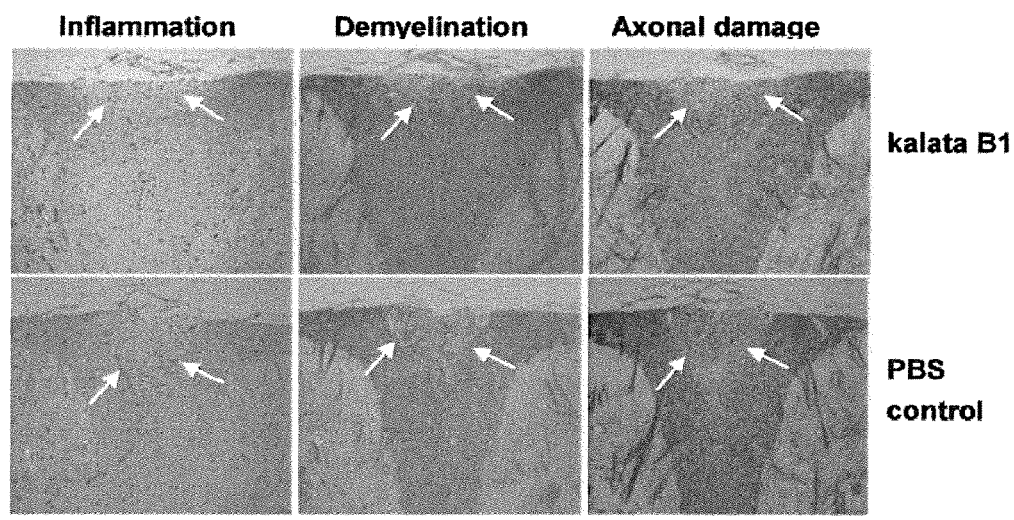
Figure 10:
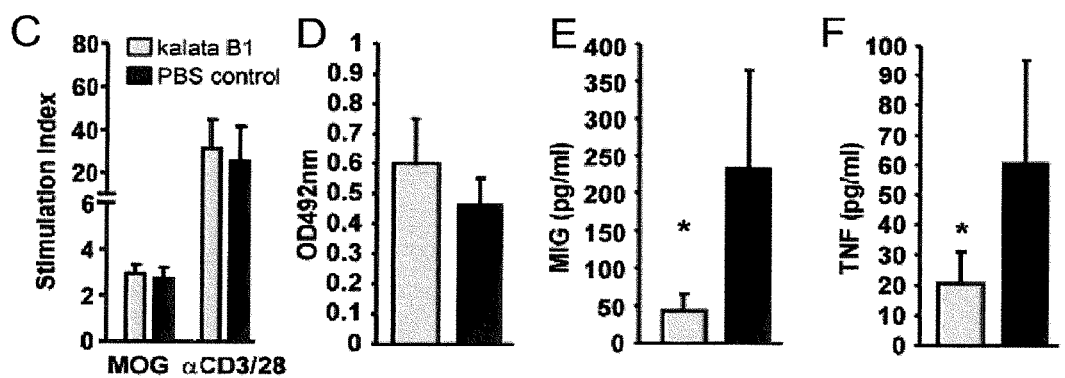

FIG. 10. Activity of kalata B1 in vivo in experimental auto-immune encephalomyelitis in mice. (A) Clinical score of EAE mice after vaccination with kalata B1 (light line) or PBS control (black line) was determined as outlined in Materials and Methods Section. Vaccination with the cyclotide resulted in a reduction in the incidence and severity of EAE. (B) The influence of kalata B1 vaccination on the formation of CNS inflammatory and demyelinating lesions was examined by histological studies of fixed tissue using haemotoxylin/eosin, Luxol fast blue and Bielshowsky silver staining. The CNS of all mice treated with PBS showed inflammatory lesions, demyelination and axonal damage were particularly florid in the cerebellum and spinal cord (indicated by arrows). Vaccination with kalata B1 leads to a reduction of both clinical signs and histological lesions of EAE. (C) Proliferation of spleen cells in response to the encephalitogen $MOG_{35-55}$ and stimulation by the polyclonal activators, anti-CD3 and anti-CD28 antibodies shows regardless of the treatment regimen, splenocytes from all vaccinated mice proliferated to MOG and these splenocytes displayed strong proliferative responses to the anti-CD3/CD28 antibodies. (D) Suppression of EAE by kalata B1 is not associated with a suppression of anti-MOG antibodies production. As shown, anti-MOG antibodies were detected in all sera regardless of the vaccination regimen. (E, F) MOG-reactive T cells in protected animals did not switch to an anti-inflammatory T cell phenotype. Significantly reduced levels of the chemokine MIG (E) and TNFα (F) were demonstrated in non-stimulated spleen cell supernatants generated from animals treated with kalata B1.

Figure 11:
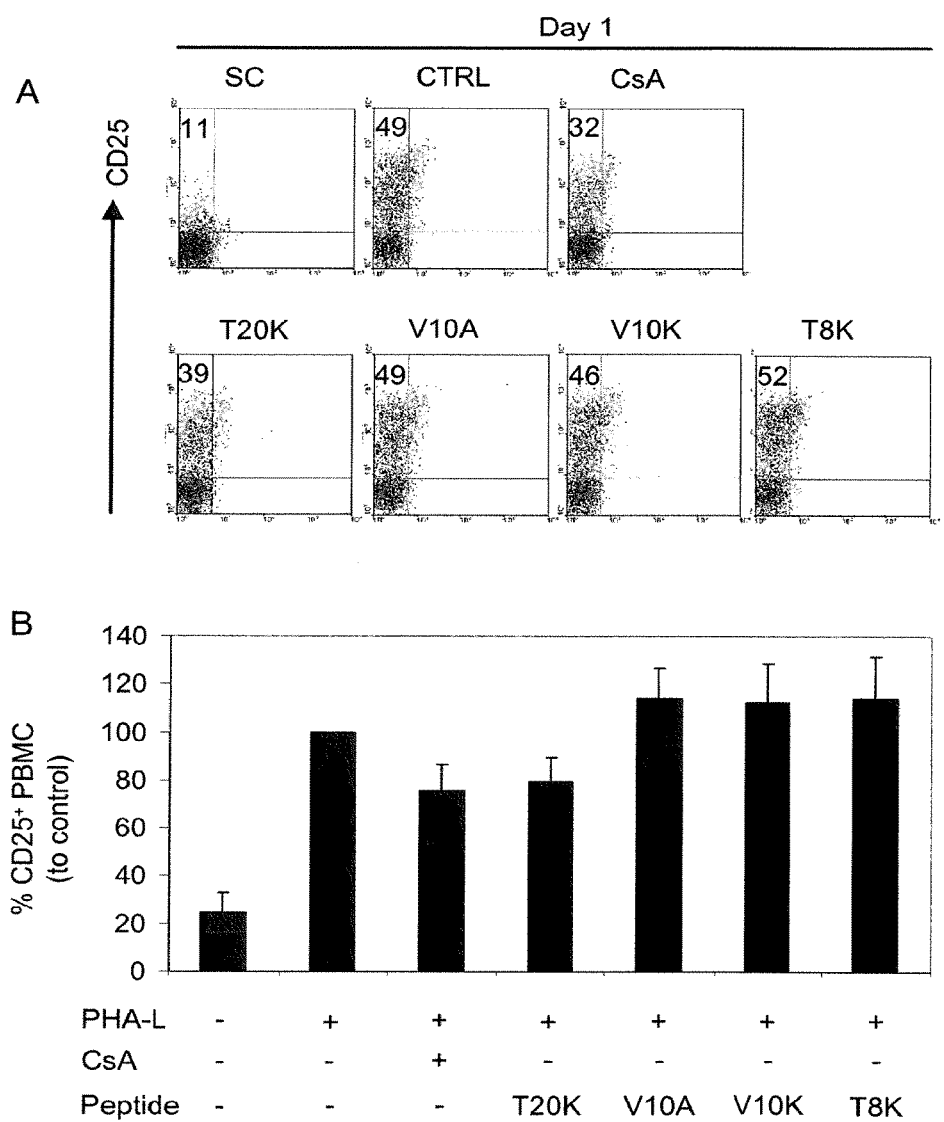
Figure 11:
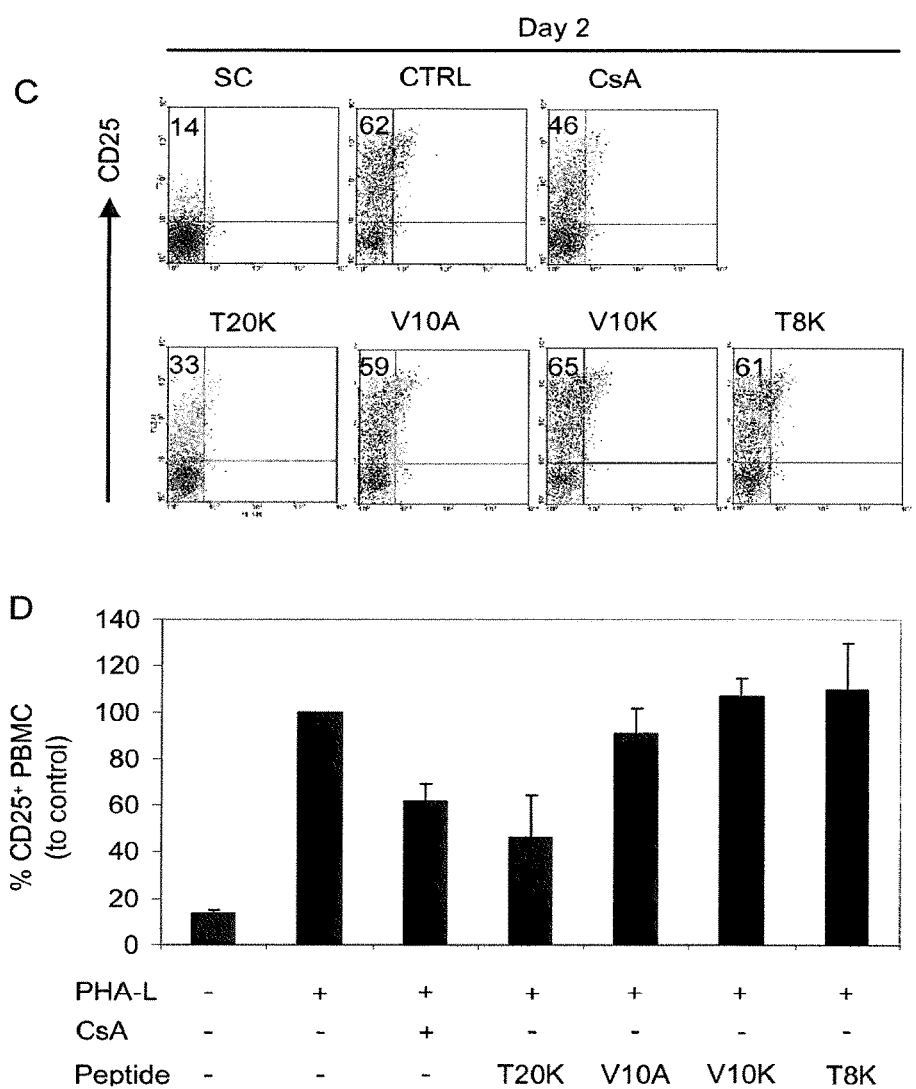

FIG. 11. Expression of IL-2 receptor alpha chain CD25 on PBMC following cyclotide treatment. PBMC were pretreated with cyclosporine A (CsA; 5 µg/mL) or different cyclotides (4 µM; T20K, V10A, V10K, T8K) and were cultivated in the presence of media (SC) or were stimulated with PHA-L (10 µg/mL; CTRL). At day 1 (A and B) or day 2 (C and D) after cultivation, the cells were surface-stained with anti-human CD25 mAbs and were analyzed by flow cytometry. Representative results were depicted as dot plots (A and C) and results of three independent experiments are presented as mean and standard deviation (SD) of three independent experiments. The asterisks represent significant differences from untreated stimulated cells alone. The percentages indicated in the dot plots represent the $CD25^+$ PBMC.

Figure 12:
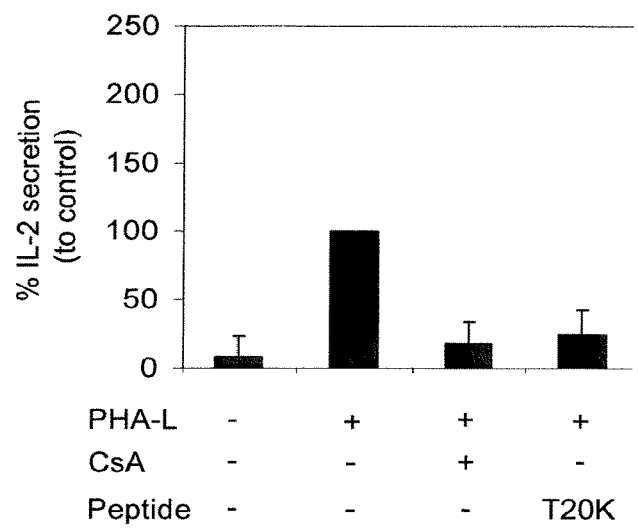
Figure 12:
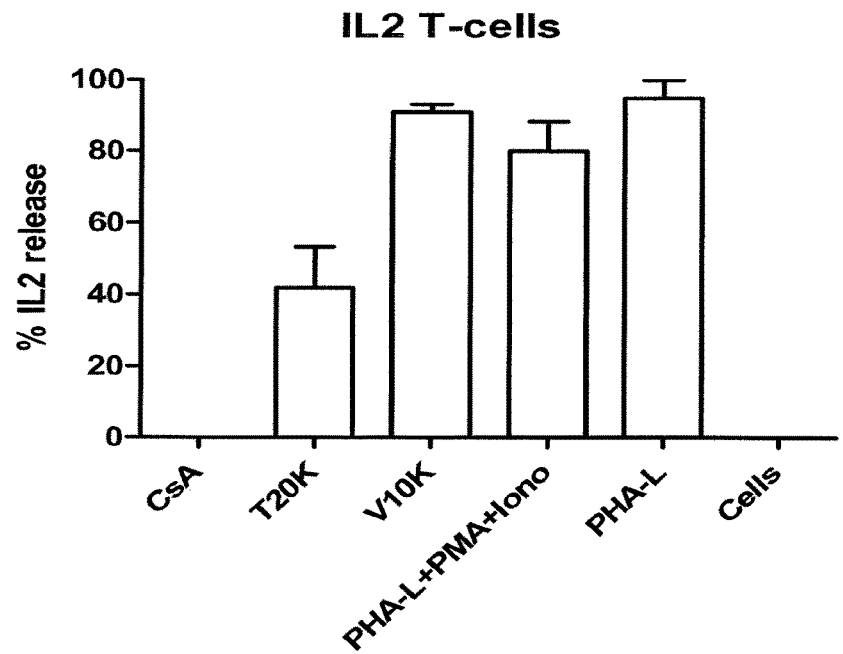
Figure 12:
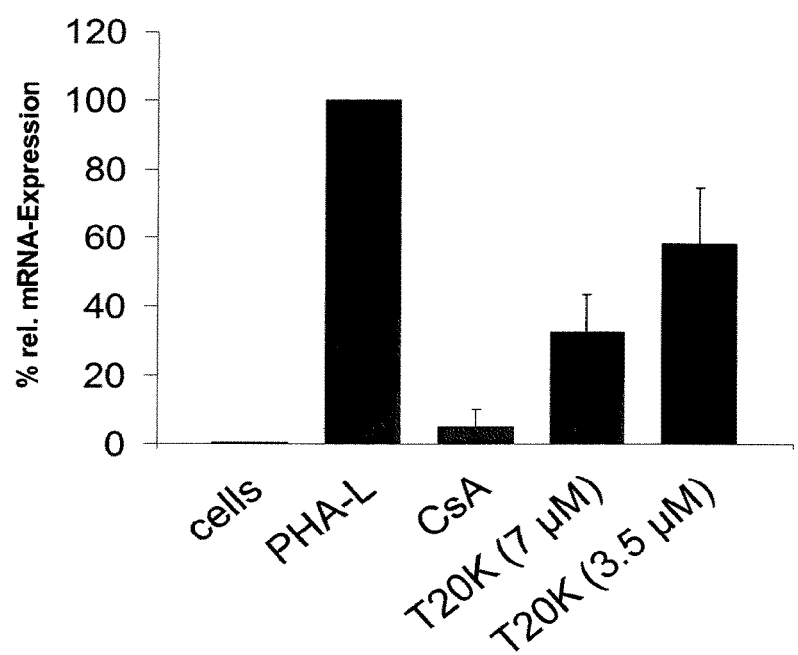

FIG. 12. A. IL-2 secretion from cyclotide-treated activated PBMC. PBMC were pretreated with cyclosporine A (CsA; 5 µg/mL) or a cyclotide (4 µM; T20K) and were cultivated in the presence of media (SC) or were stimulated with PHA-L (10 µg/mL; CTRL). 24 hours after cultivation, PBMC were restimulated with PMA/Ionomycin for further 6 hours. Afterwards, the amount of IL-2 was measured in the supernatant by using an ELISA-based flow cytometric technique. Data are presented as mean and standard deviation (SD) of three independent experiments.

B. IL2 release in human T-cells after treatment with cyclotide. Human T-cells (provided by A. Dohnal, PhD; from CCRI, Vienna) 4×106/mL were seeded in 96-well flat-bottom plates (100 µL/well) and incubated for two hours at 37° C. before they were stimulated with CsA (5 mg/mL), T20K (4 µM) and V10K (4 µM). After another two hours PHA-L (10 µg/mL) was added to the appropriate wells and incubated over night at 37° C. On the next day T-cells were re-stimulated with Ionomycin (500 ng/mL) and PMA (50 ng/mL) for 6 hours at 37° C. Cells were then centrifuged at 3000 rpm for 5 minutes to gain their supernatants. Supernatants of stimulated T-cells were analyzed for their IL2 release using a human IL-2 ELISA Kit from eBioscience according to the manufacturer's instructions. The color reaction was evaluated at an optical density of 450 nm by the microplate reader Synergy H4 (BioTek). PHA-L stimulation of human T-cells illustrated highest IL2 release, also V10K and PMA+Ionomycin stimulation achieved comparable results, whereas untreated and CsA treated cells showed no production of this cytokine. In addition, T-cells incubated with the cyclotide T20K demonstrated a significant inhibition of cell proliferation in accordance to the IL2 level.

C. IL-2 gene expression analysis using RT-PCR. Total cellular RNA was isolated from PHA-L-activated cells that were incubated with medium, CsA or T20K for 4 hours. RT-PCR was carried out using specific primers for indicated gene. The data were normalized to the Ct value of the internal housekeeping gene 18s rRNA and the relative mRNA level in the untreated stimulated group was used as calibrator. Data were expressed as mean+SD of three independent experiments.

Figure 13:
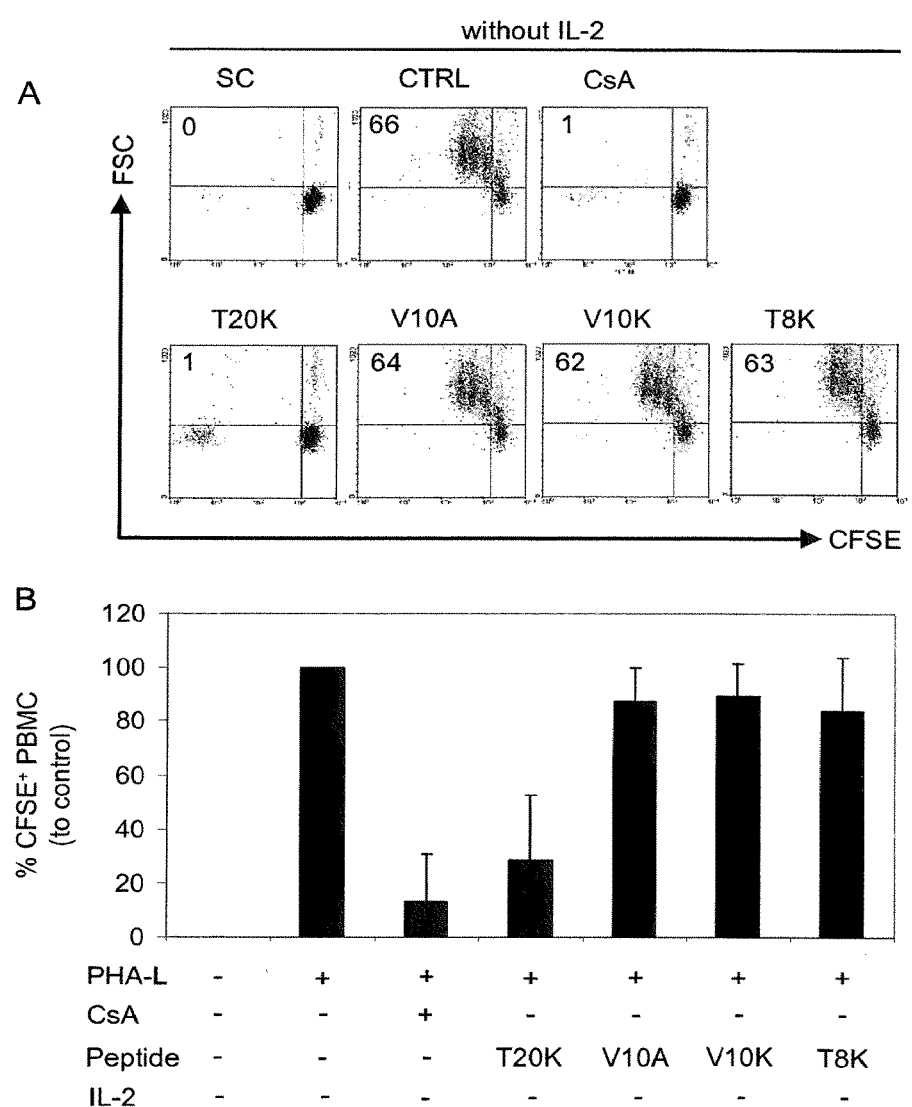
Figure 13:
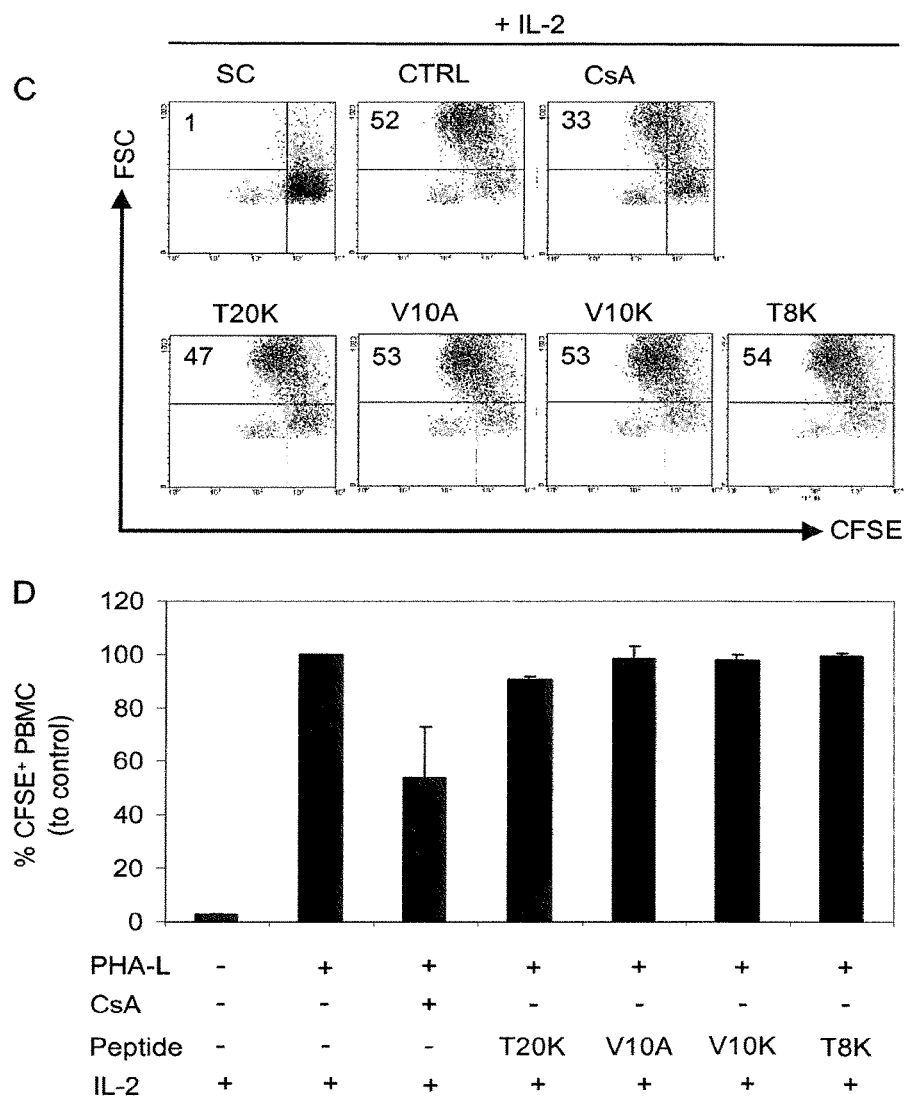

FIG. 13. Proliferation capacity of cyclotide-treated PBMC in the presence of exogenous IL-2. CFSE-labelled PBMC were pretreated with cyclosporine A (CsA; 5 µg/mL) or different cyclotides (4 µM; T20K, V10A, V10K, T8K) and were cultivated in the presence of media (SC) or were stimulated with PHA-L (10 µg/mL; CTRL). The cells were cultured without exogenous IL-2 (10 U/mL) (A and B) or in the presence of IL-2 (C and D). The CFSE-labelled cells were measured after a 3 day culture period by flow cytometry and representative data are presented in dot plots (A and C). Data are presented as mean and standard deviation (SD) of three independent experiments.

Figure 14:
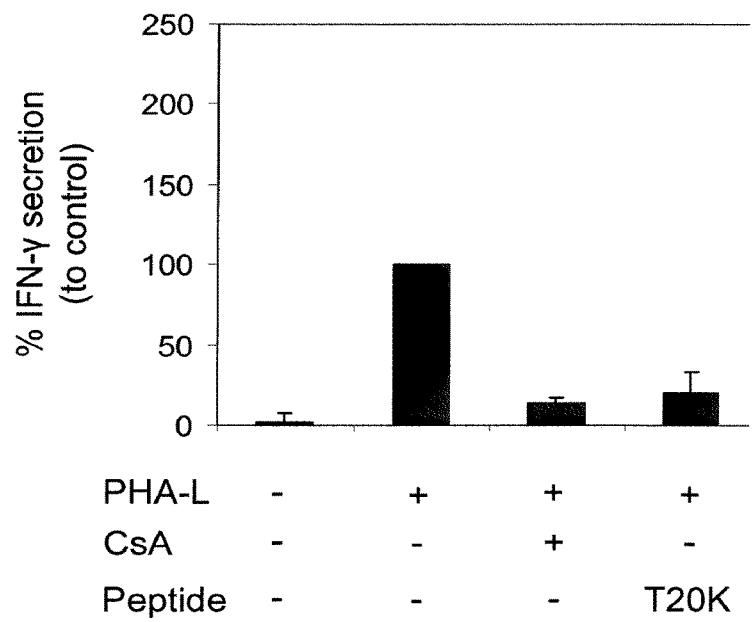
Figure 14:
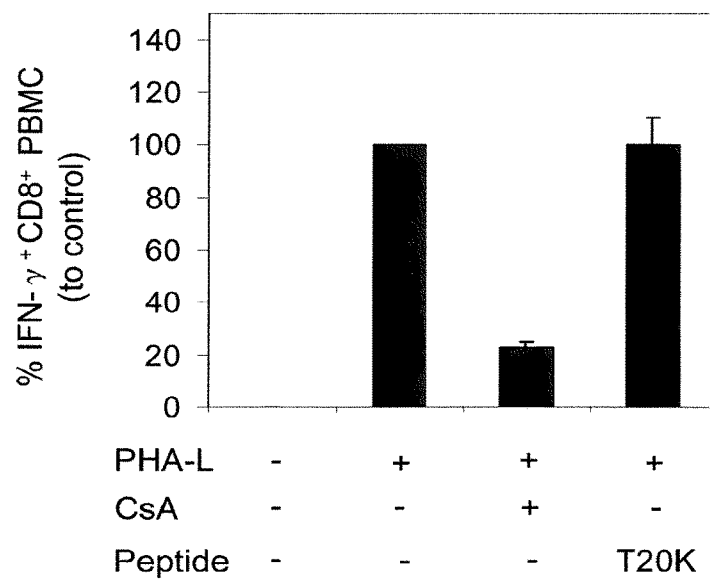

FIG. 14. IFN-γ secretion by cyclotide-treated PBMC. Purified PBMC were preincubated with a cyclotide (4 µM; T20K) or cyclosporine A (CsA; 5 µg/mL) and were stimulated with PHA-L (10 µg/mL). Untreated cells were used as control. Following 24 h or 36 h of cultivation, the cells were restimulated with PMA/Ionomycin for further 6 hour. The amount of IFN-γ was measured in the supernatant of cultured cells using an ELISA-based flow cytometric method. The data are presented as mean and standard deviation (SD) of three independent experiments.

Figure 15:
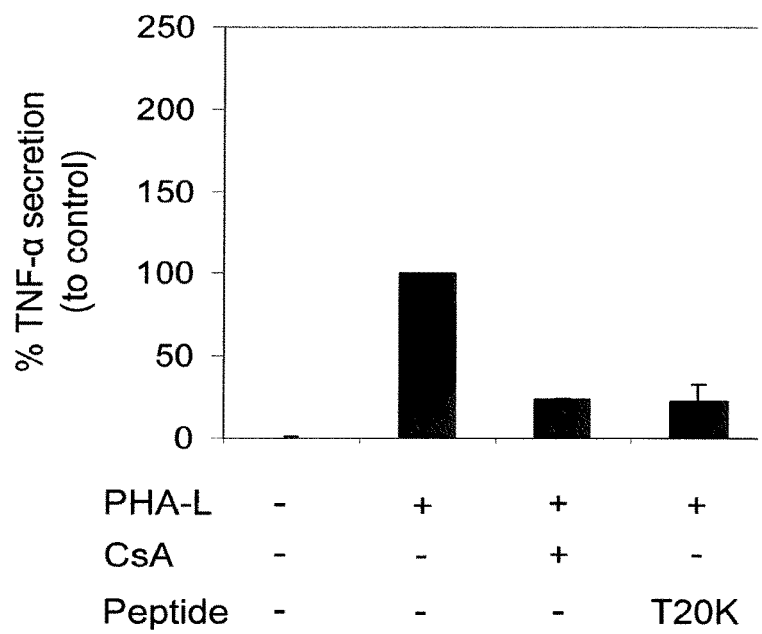
Figure 15:
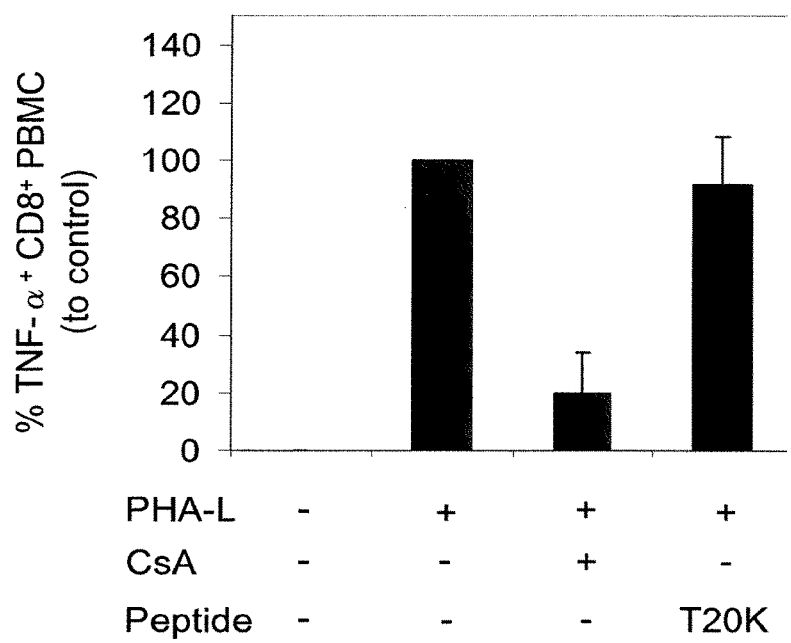

FIG. 15. TNF-alpha secretion from cyclotide-treated PBMC. Purified PBMC were preincubated with a cyclotide (4 µM; T20K) or cyclosporine A (CsA; 5 µg/mL) and were stimulated with PHA-L (10 µg/mL). Untreated cells were used as control. Following 24 h or 36 h of cultivation, the cells were restimulated with PMA/Ionomycin for further 6 hour. The amount of TNF-alpha was measured in the supernatant of cultured cells using an ELISA-based flow cytometric method. The data are presented as mean and standard deviation (SD) of three independent experiments.

Figure 16:
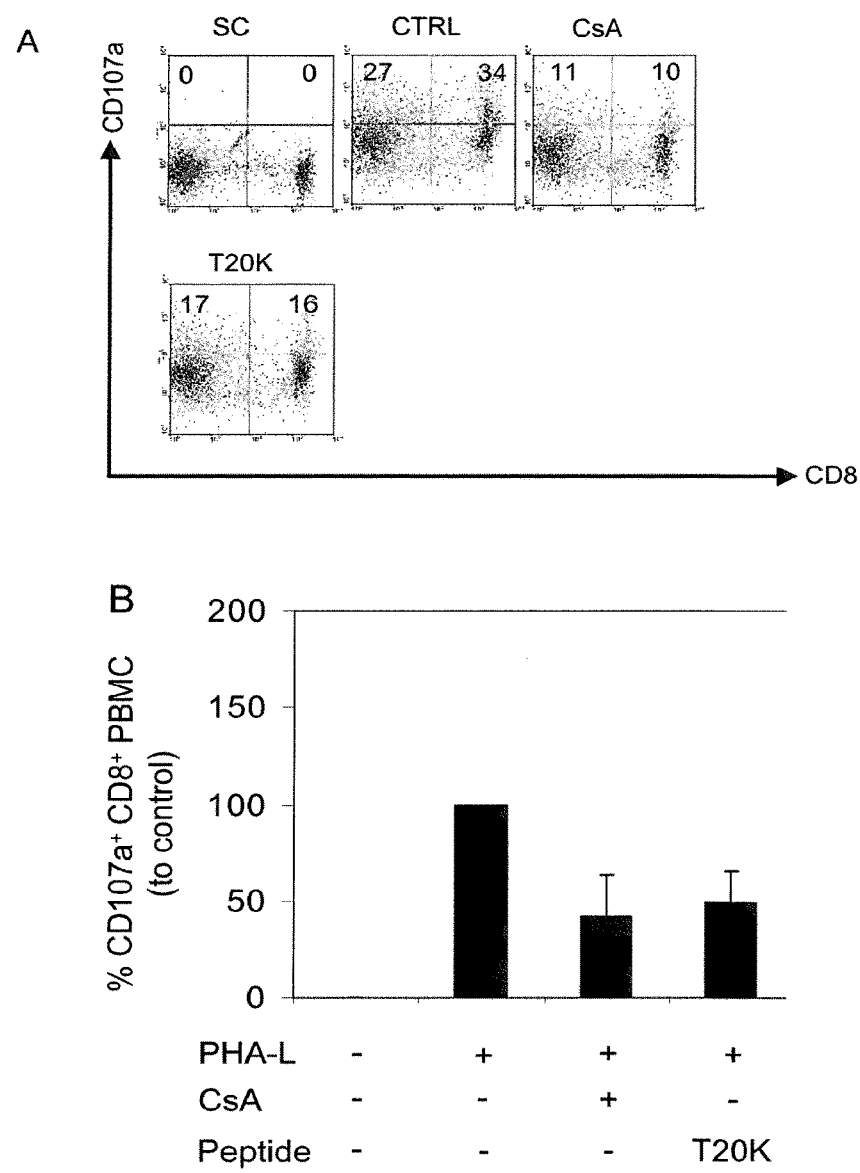

FIG. 16. Degranulation capacity of cyclotide-treated activated human PBMC. PBMC were pretreated with cyclosporine A (CsA; 5 µg/mL) or a cyclotide (4 µM; T20K) and were cultivated in the presence of media (SC) or were stimulated with PHA-L (10 µg/mL; CTRL). After 36 hour of cultivation the cells were restimulated with PMA/Ionomycin for 2.5 hours in the presence of a CD107a mAbs and GolgiStop reagent to determine the amount of degranulation by flow cytometry. Representative data are shown in dot plots (A) and in (B) data are presented as mean and standard deviation (SD) of three independent experiments.

Figure 17:
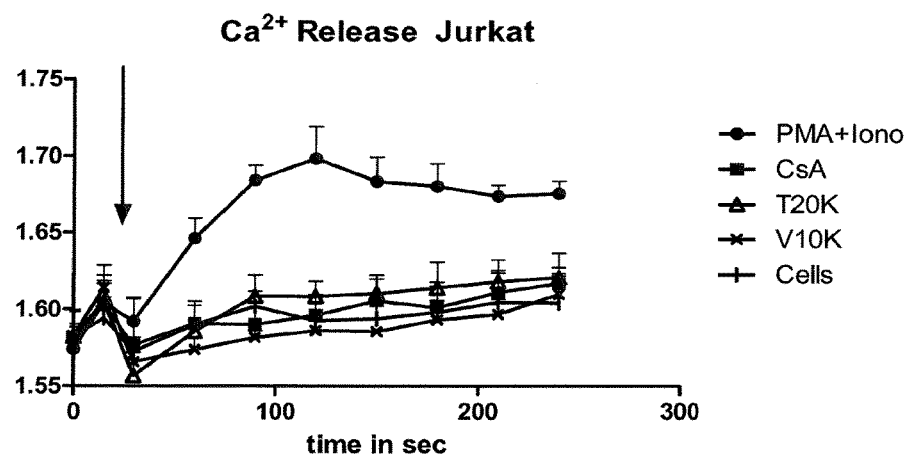
Figure 17:
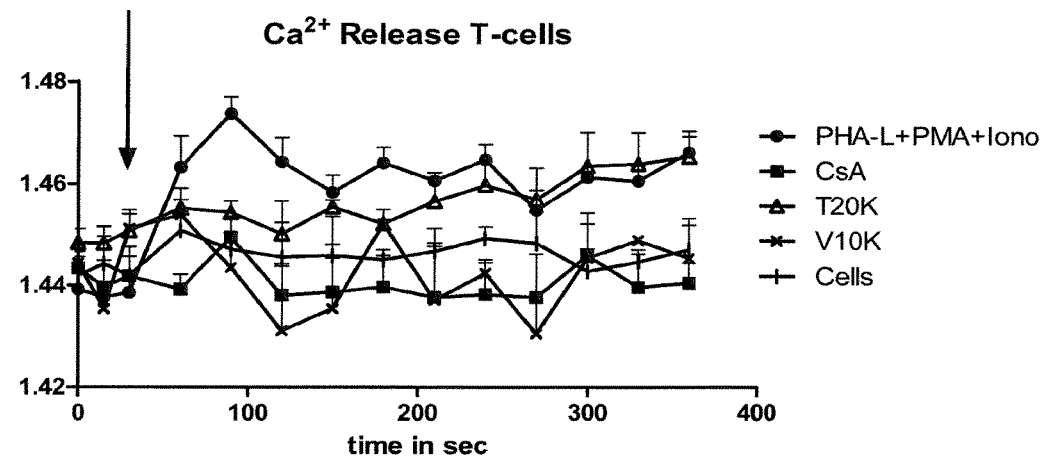

FIG. 17. $Ca^{2+}$ release in human Jurkat and T-cells. Jurkat cells (A) and T-cells (B) $1\times10^6$ were loaded with 1 µM Fura-2 and 0.02% Puronic F-127 for 30 minutes at 37° C. Cells were centrifuged for 5 minutes at 1200 rpm and resuspended in media [RPMI 1640 with 10% FCS, penicillin (100 U/mL) and streptomycin (100 U/mL)]. 100 µL of cell suspension were transferred to a black 96-well plate with a clear flat-bottom. Briefly before analysis the fluorometer Synergy H4 (BioTek) was tempered to 37° C. The fluorescence time course was then measured with: extinction 340/380 nm and emission 510 nm in 30 seconds intervals, continuously shaking. $Ca^{2+}$ influx was initiated by adding compounds to the cells (illustrated by the arrow). To receive maximum $Ca^{2+}$ release cells were stimulated with PMA (50 ng/mL) and Ionomycin (500 ng/mL) and T-cells additionally with PHA-L (10 µg/mL). For lowest $Ca^{2+}$ levels, cells remained untreated. CsA (5 mg/mL), T20K (4 µM) and V10K (4 µM) stimulation did not induce a change in $Ca^{2+}$ signaling in Jurkats. In contrast human primary T-cells demonstrate an increasing $Ca^{2+}$ release after incubation with the cyclotides T20K.

Figure 18:
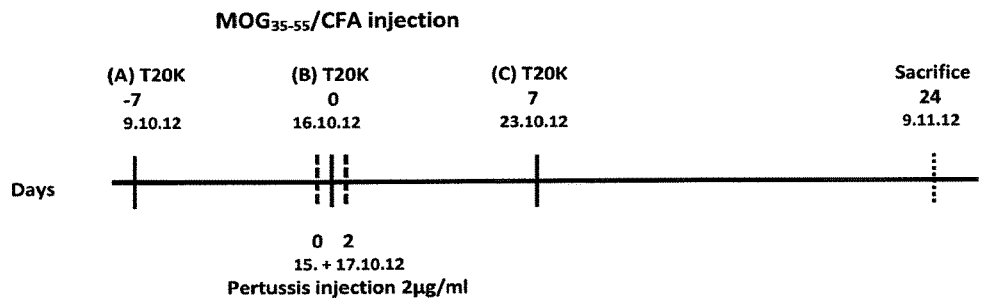

FIG. 18. Immunisation scheme (see also Example 14)

Figure 19:
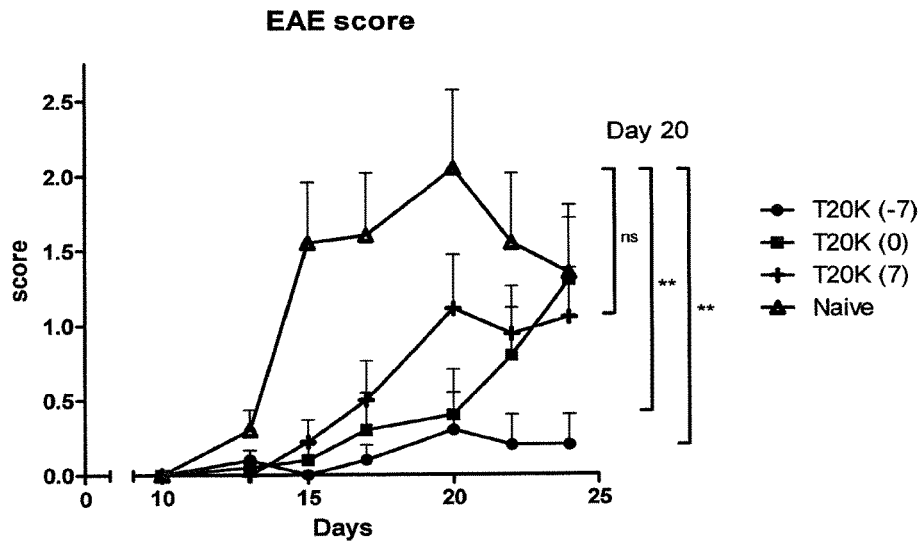

FIG. 19. Effect on clinical EAE score. After induction of EAE, mice treated with T20K and naïve mice were scored every second day, starting at day 10. The naïve group, which received no T20K developed worst disease course, whereas T20K treated mice showed delayed and minor symptoms of EAE referred to the time point of cyclotides injection. Especially mice treated seven days before EAE induction demonstrate significantly the prophylactic effect of the kalata B1 mutant (according to Dunnett's multiple comparison test).

Figure 20:
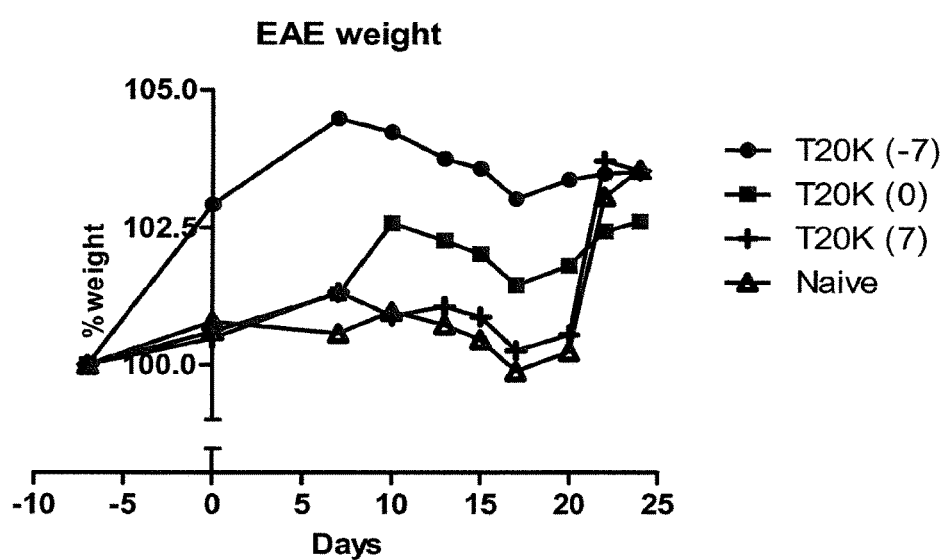

FIG. 20. Effect on weight of EAE-induced mice. Weight of immunized mice was measured at day (−7), 0, 7 and on each day besides scoring. Mice receiving cyclotide injections at day (−7) gained weight within the next days. Whereas untreated mice or mice which were treated at day 7 remained constant or even lost body weight according to the disease course. About day 20 EAE in these two groups ameliorated and therefore these mice regained body weight.

Figure 21:
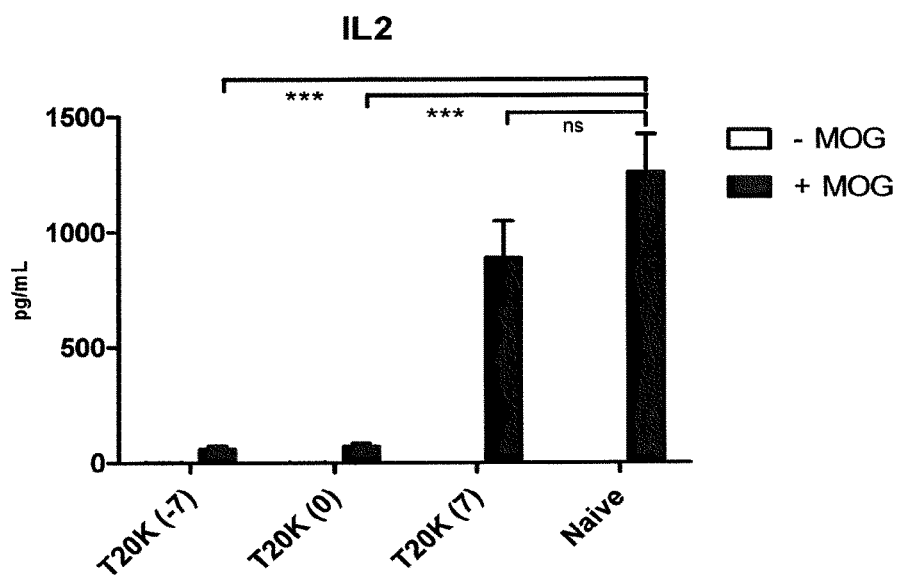
Figure 21:
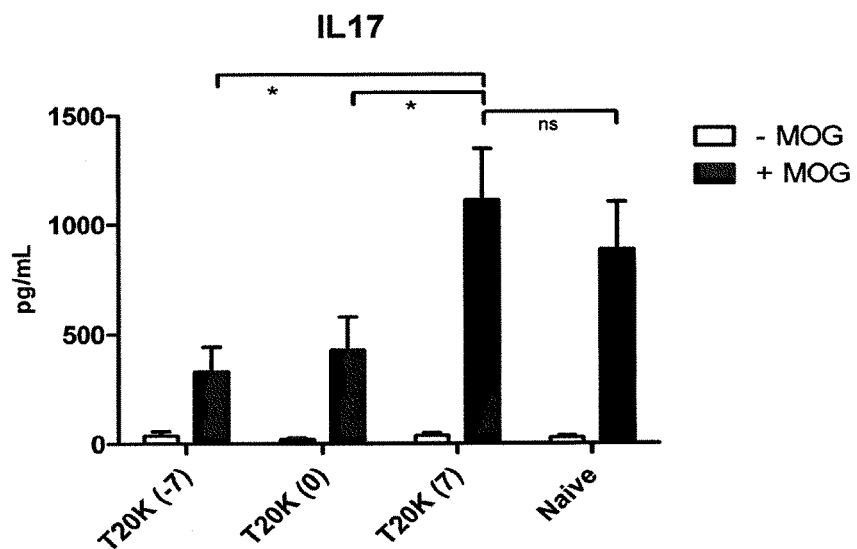
Figure 21:
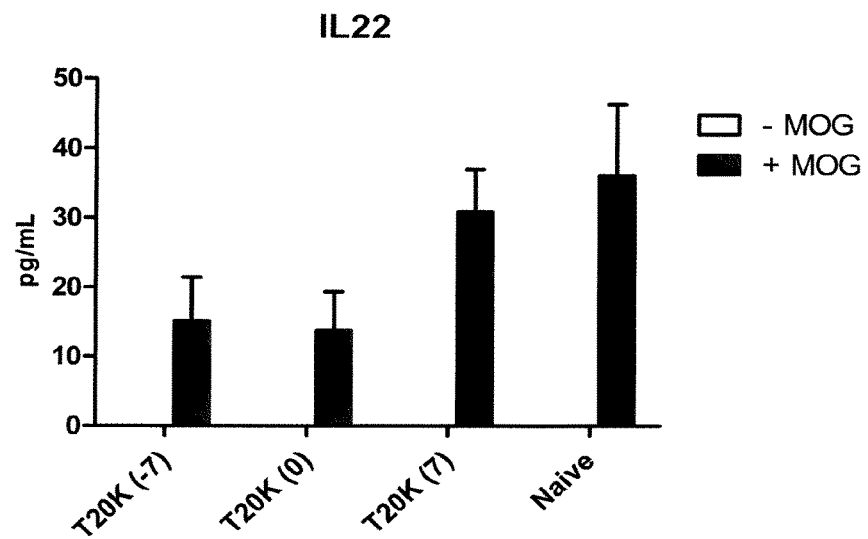
Figure 21:
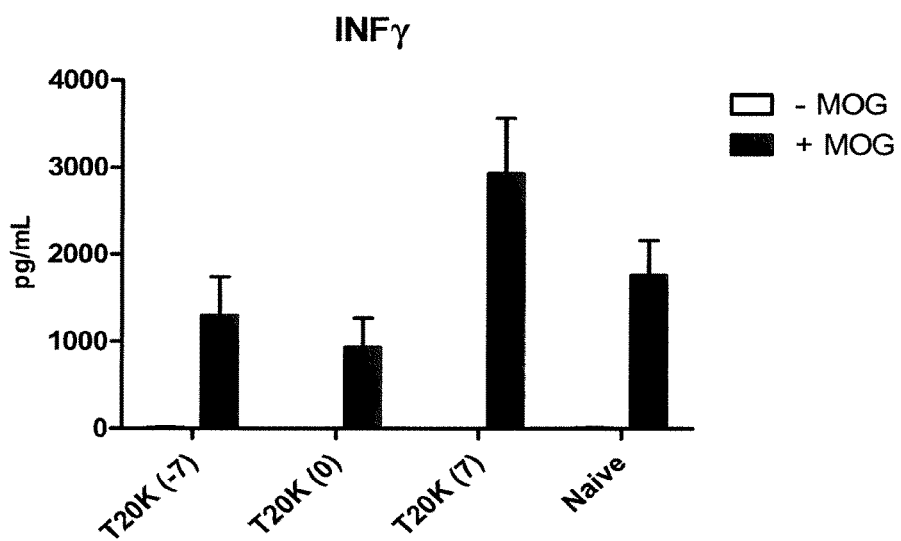
Figure 21:
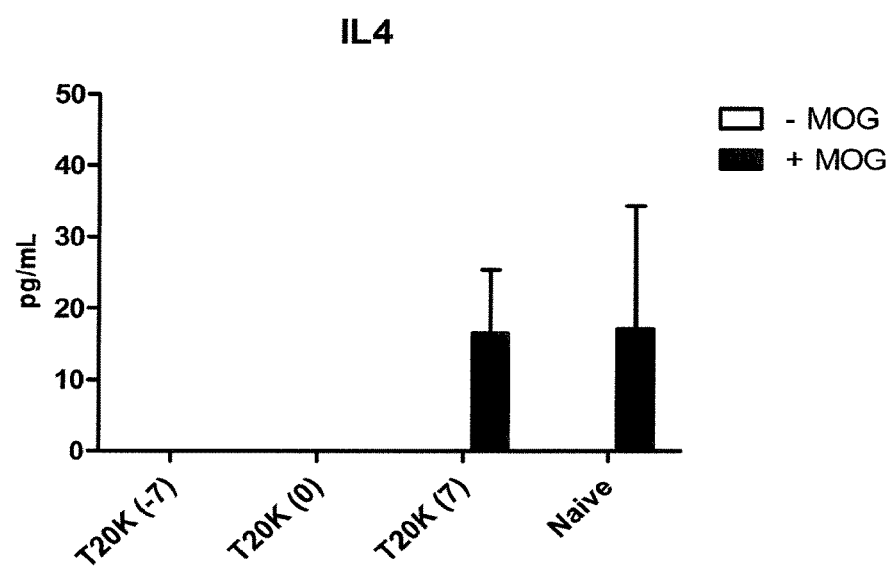

FIG. 21. Effect on cytokine release of ex vivo isolated PBMC at day 3. Spleenocytes of sacrificed mice were isolated and restimulated with $MOG_{35-55}$ (30 µg/mL) for three days or left untreated. Supernatants of these cells were used for analyzing cytokine release in ELISAs. In (A) interleukin 2 release was highest in splenic T-cells isolated from naïve mouse group that were restimulated with MOG, correlating with disease course. In T20K (7) treated mice IL2 release was lower than in naïve group after MOG stimulation. Spleenocytes from pre-treated mice (T20K −7, 0) show a significant inhibition of the IL2 production (according to Dunnett's multiple comparison test). This inhibitory effect could also be demonstrated towards the cytokines IL17, IL22 and INFγ in T-cells of T20K (−7, 0) treated mice, although not significantly (B-D). There was hardly any cytokine IL4 detectable (E), opposing a $T_H2$ immune response, which was expected.

Figure 22:
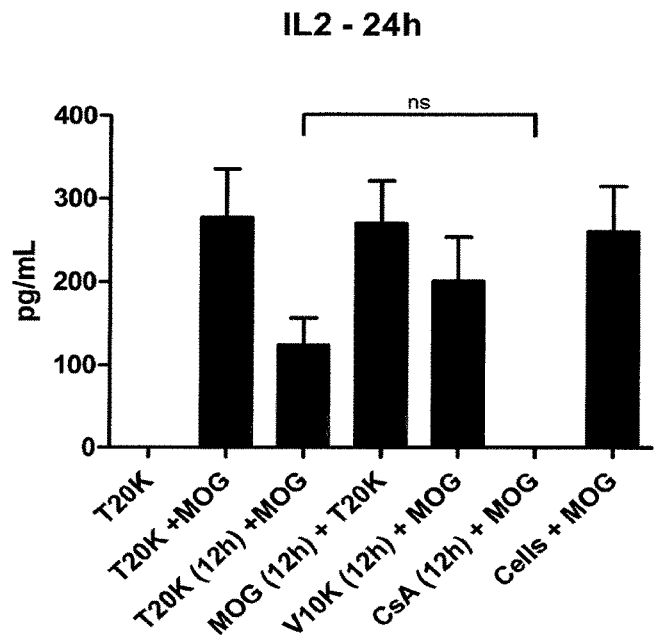
Figure 22:
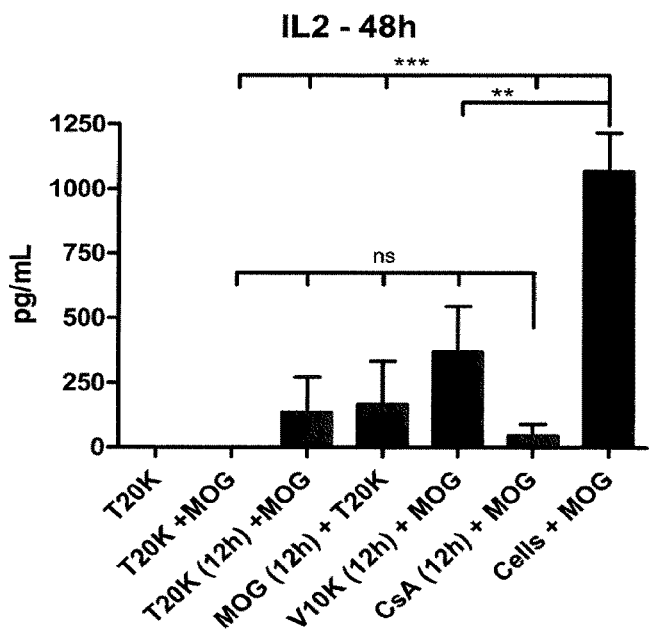
Figure 22:
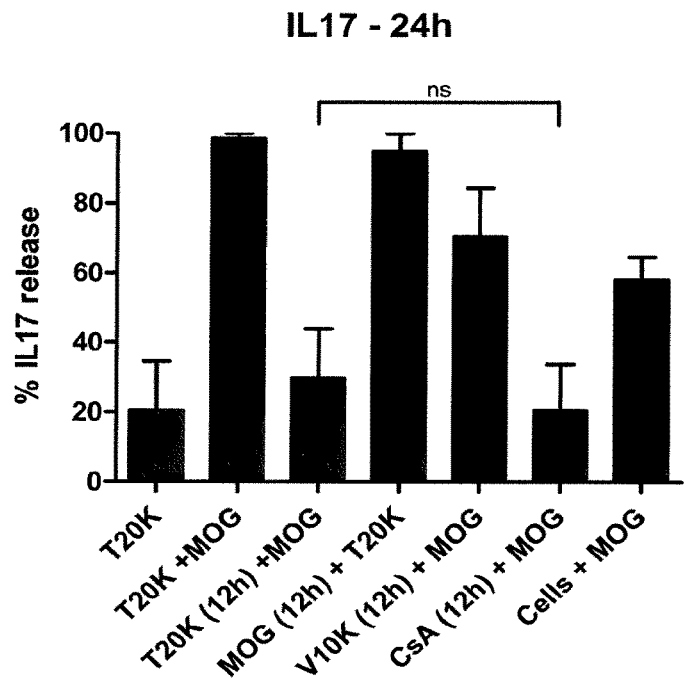
Figure 22:
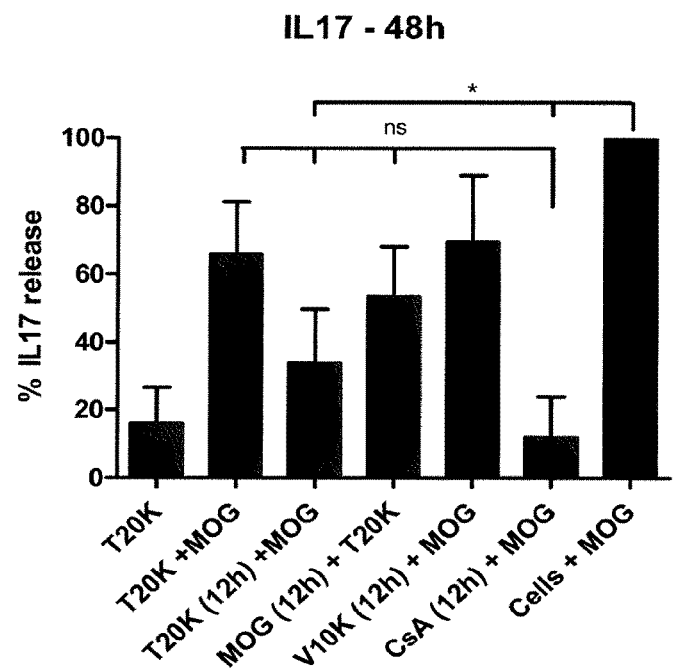
Figure 22:
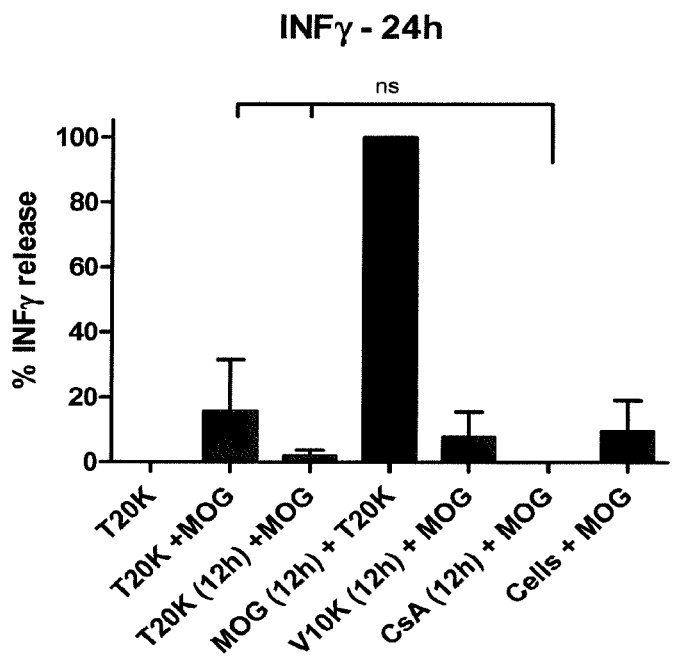
Figure 22:
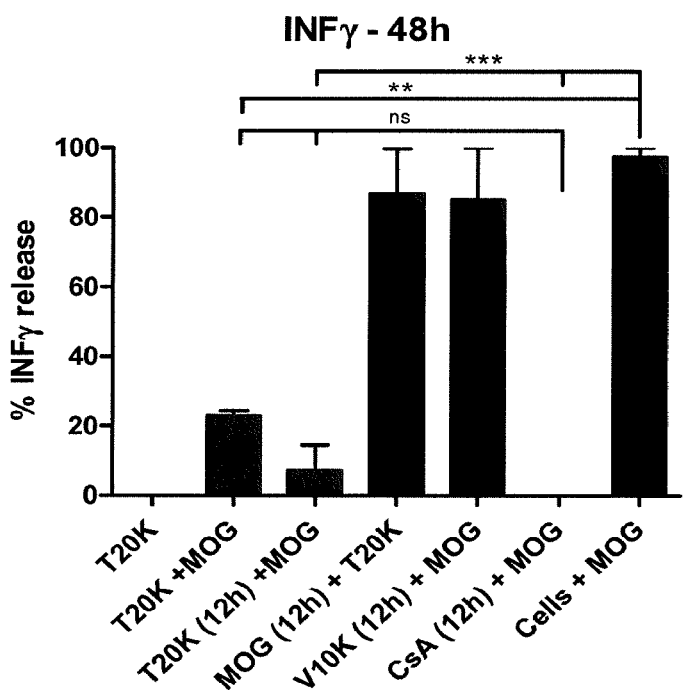
Figure 22:
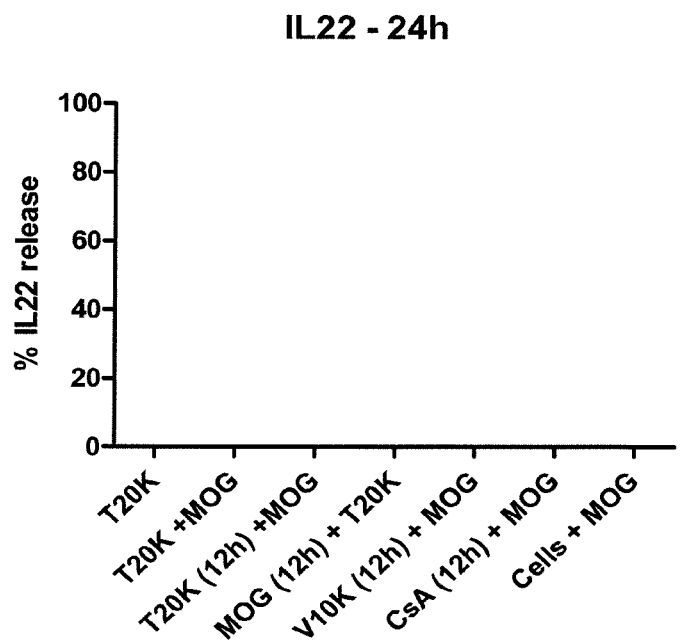
Figure 22:
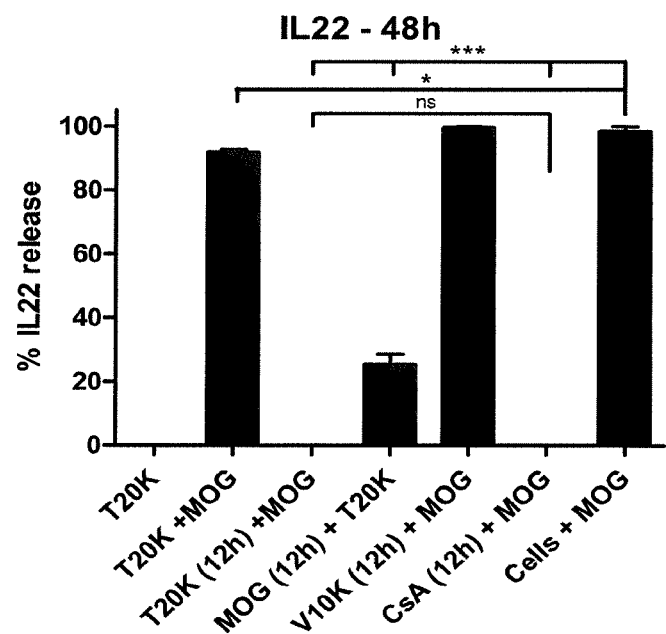
Figure 22:
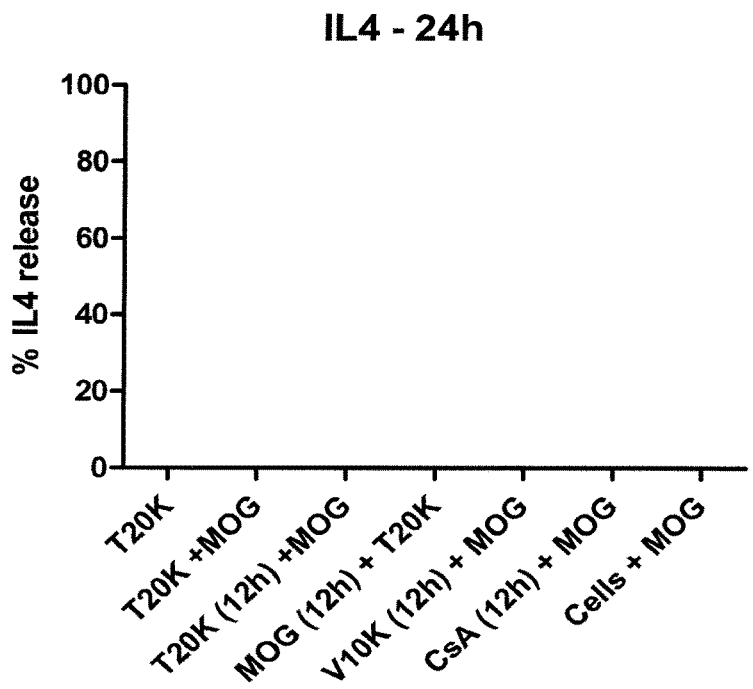
Figure 22:
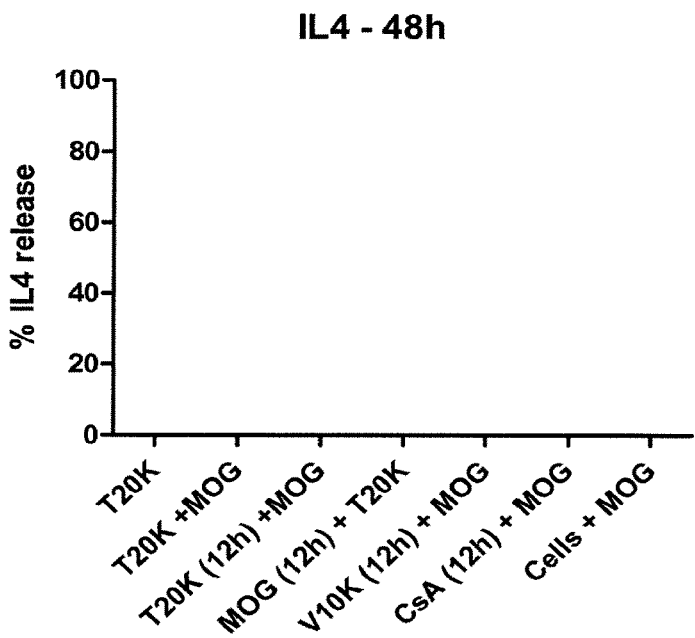

FIG. 22. Effect on cytokine release of ex vivo isolated PBMC at day 1 and 2. Splenic T-cells of sacrificed naïve mouse group were isolated and stimulated with T20K (4 µM) at different time points, with $MOG_{35-55}$ (30 µg/mL) and for control purposes with CsA (5 µg/mL) and V10K (4 µM), as indicated here. IL2 release is significantly inhibited after a 48 h incubation of the cells with T20K, independent to the different time points of cyclotide addition. Even after 24 h IL2 inhibition is non-significant to the immune suppressive agent CsA. Also V10K shows a inhibitory capacity towards IL2 release in mouse T-cells after 48 h incubation (A, B). The production of the cytokine IL17 is also inhibited by T20K after 48 h, related to the time point of compound addition (C, D). Furthermore INFγ and IL22 cytokine release is repressed significantly, dependent on the cyclotide addition (E-H). To approve this EAE $T_H$ bias towards $T_H17$ and $T_H1$ cells, IL4 release was again analyzed, but this $T_H2$ cytokine was not detectable (I, J), as already indicated in (D).

Figure 23:
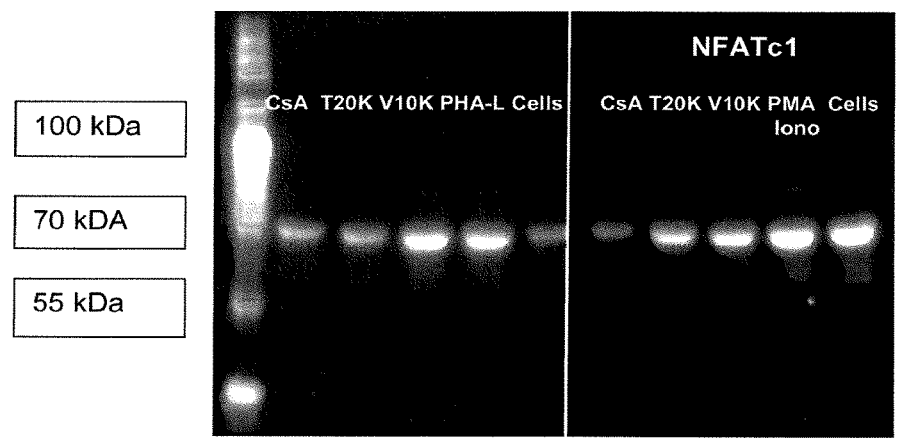
Figure 23:
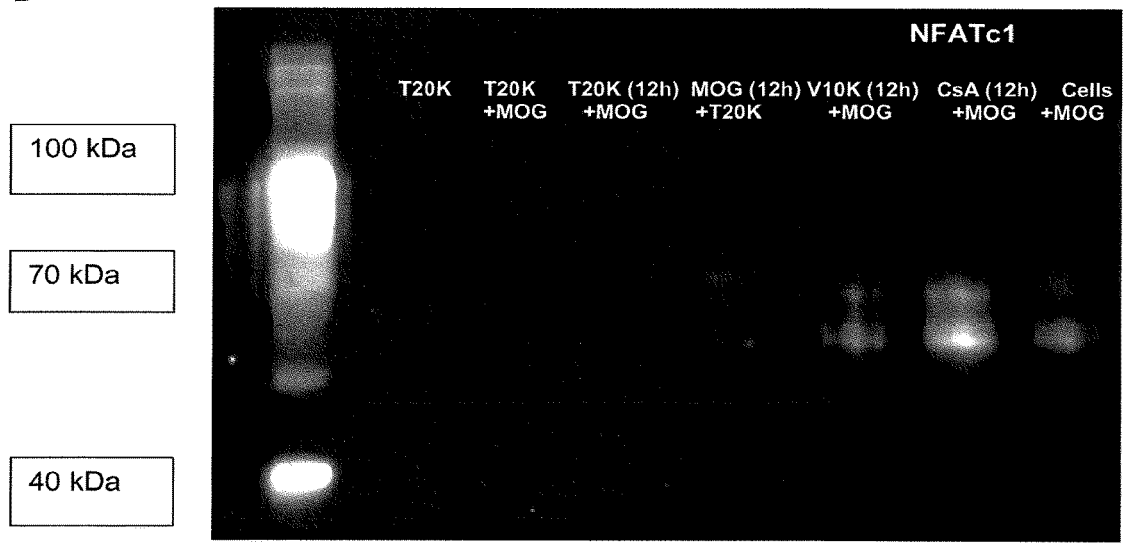

FIG. 23. Effect of cyclotides on protein expression of NFAT1c. Human T- cells were incubated with the CsA (5 µg/mL), T20K (4 µM) and V10K (4 µM) for two hours. But instead of stimulating with PHA-L and PMA/ionomycin, one part of the cells was stimulated with PHA-L (10 µg/mL) and the other with PMA (50 ng/mL)/ionomycin (500 ng/mL) over night. CsA and T20K incubation show a reduced signal of NFATc1 compared to the cells stimulated with V10K, PHA-L and PMA/Ionomycin (A). Splenic T-cells isolated from naïve mouse group were stimulated as described above. Cells incubated with the cyclotides T20K demonstrate a reduced NFATc1 signal compared to cells incubated with V10K and cells stimulated with the natural antigen MOG.

Although, cells treated with the immunosuppressant compound CsA which has NFAc1 as a major molecular target, show a strong signal (B).

Figure 24:
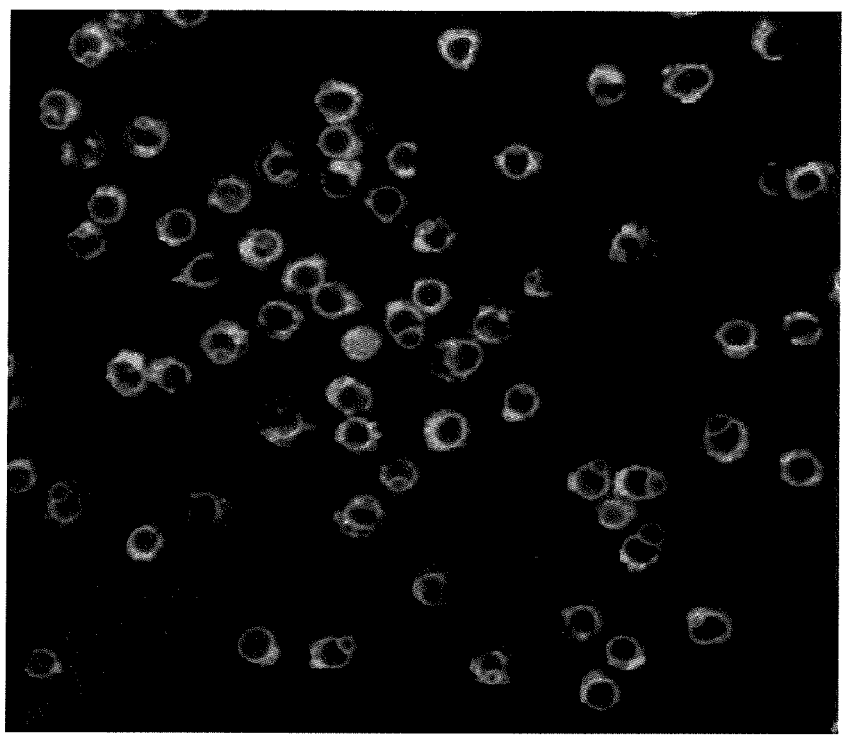
Figure 24:
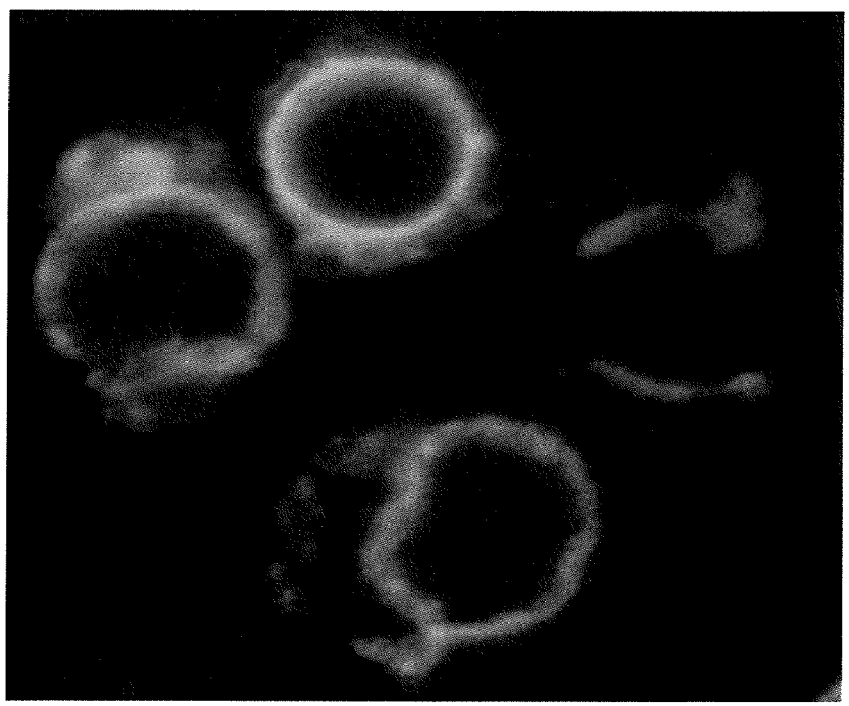
Figure 24:
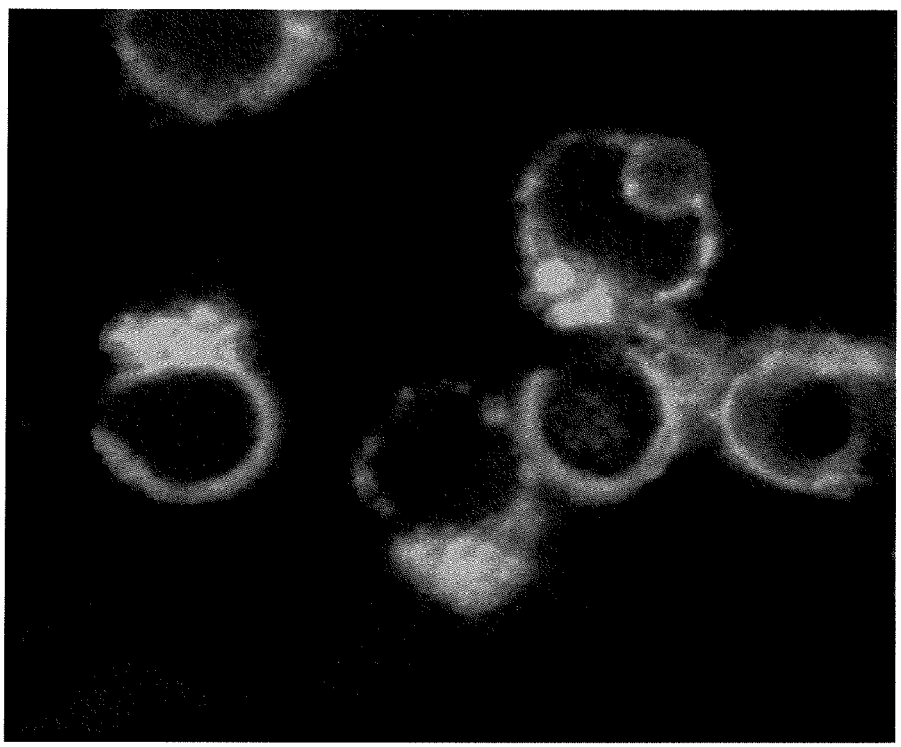
Figure 24:
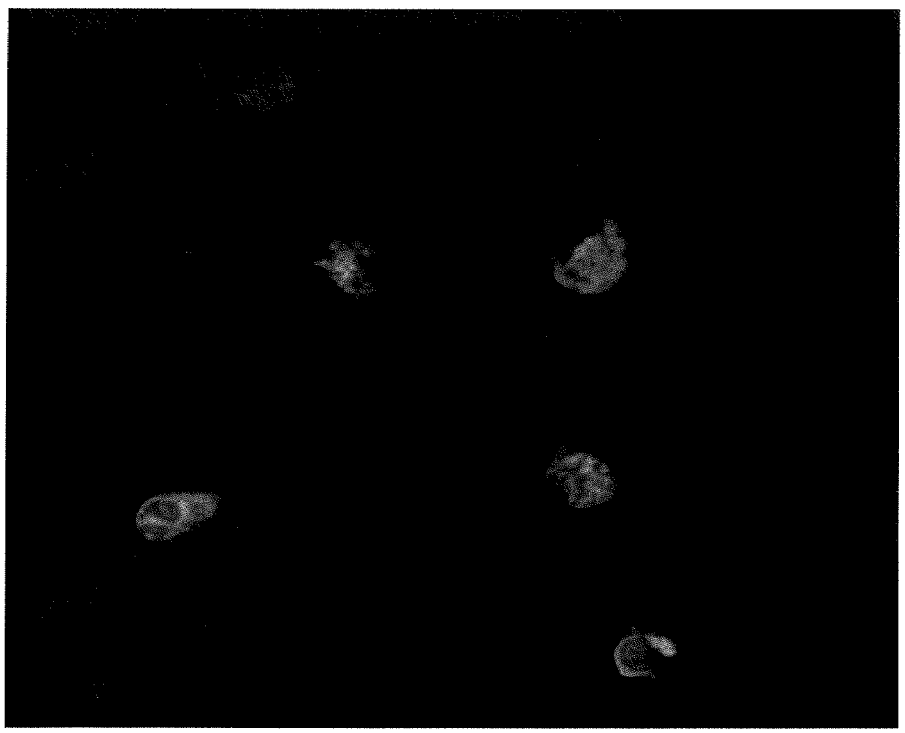

FIG. 24. Cellular uptake of T20K. Human T-cells, were incubated with 4 µM T20K labeled with FITC to perform fluorescence microscopy. (A) demonstrates an overview of the T-cells with the incorporated cyclotides T20K in their cytosol. It seems that the peptide is mostly found around the membrane of the nucleus, but also in the membrane of vesicular compartments, like the Golgi apparatus or the Endoplasmic reticulum (B, C). In contrast incubating Jurkats (D) with the labeled peptide did not show this intracellular fluorescence, instead the cyclotides stained only dead cells.

The Examples illustrate the invention.

EXAMPLE 1: MATERIAL AND METHODS

Extraction Preparation and Purification of Plant Cyclotides.

*Oldenlandia affinis* (R&S) DC. plants were grown in the glass house at the Department of Pharmacognosy (University of Vienna) from seeds that were obtained as a gift from David Craik (Institute for Molecular Biosciences, University of Queensland). Aerial parts of the plants have been harvested and dried. Plant material was pulverized using a rotor grinder and extracted twice overnight in dichloromethane:methanol (1:1 v/v). The extracts were concentrated on a roto-evaporator and were lyophilized. The dried extracts were dissolved in solvent A (ddH$_2$O with 0.1% TFA) and in-batch pre-purified with C$_{18}$ solid phase extraction (ZEO-prep 60 Å, C$_{18}$ irregular 40-63 µm; ZEOCHEM, Uetikon, Switzerland). To separate the hydrophilic non-cyclotide compounds from the hydrophobic cyclotide compounds, the C$_{18}$-beads were washed with 10% solvent B (90% acetonitrile in ddH$_2$O with 0.08% TFA) and eluted with 80% solvent B. The eluate containing cyclotides was analyzed by MALDI-TOF MS and reconstituted in ddH$_2$O at 10 mg/mL for biological assays or used for nano LC-MS/MS analysis and further purification. Kalata B1 was purified from crude O. affinis extract by HPLC using a Perkin Elmer Series 200 system with preparative (Phenomenex Jupiter, 10 µm, 300 Å, 250×21.2 mm; 8 mL/min) and semi-preparative (Kromasil C$_{18}$, 5 µm, 100 Å, 250×10 mm; 3 mL/min) RP-C$_{18}$ HPLC columns and linear gradients from 0-80% solvent B in 80 min. Eluting peptides were monitored with UV-absorbance (A$_{280}$), collected manually and lyophilized. Purity and quality of kalata B1 was assessed by analytical HPLC and MALDI-TOF MS.

Nano LC-MS and LC-MS/MS Analysis.

Crude, ZipTip™ prepared or digested plant extracts (C$_{18}$ pre-purified O. affinis extract, see above) were analyzed by nano LC-MS or LC-MS/MS on an Ultimate 3000 nano HPLC system controlled by Chromeleon 6.8 software (Dionex, Amsterdam, The Netherlands). For LC analysis, samples of O. affinis extract (1-5 µL) were injected, pre-concentrated using Dionex PepMap™ C$_{18}$ cartridges (300 µm×5 mm, 5 µm, 100 Å) and separated by nano-RP-HPLC prior to online MS analysis using a Dionex Acclaim PepMap™ C$_{18}$ column (150 mm×75 µm, 3 µm, 100 Å; 300 nL/min). The mobile phase consisted of solvent C (0.1% aqueous formic acid) and solvent D (90/10 acetonitrile/0.08% aqueous formic acid). Peptides were eluted using a linear gradient of 4-90% D in 35 min, 5-min hold at 90% D, followed by a return to 4% D for a 20-min equilibration. For LC-MS/MS analysis aliquots (1-10 µL) of tryptic or endoGluC digested plant extracts were pre-concentrated and separated by C$_{18}$ nano LC as described above, using several LC gradients of up to 120 min duration (e.g., 4-60% B in 100 min, 60-90% B in 1 min and finally a 5-min hold at 90% B, followed by a return to 4% B for a 10-min equilibration). Eluated peptides were directly introduced into the nanospray source. Mass spectrometry experiments were performed on a hybrid quadrupole/linear ion trap 4000 QTRAP MS/MS system (ABSciex, Foster City, Calif., USA) running with the Analyst 1.5.1 software package. The 4000 QTRAP equipped with a nano-spray source was operated in positive ionization mode. LC-MS analyses for cyclotide quantification and identification by molecular weight were performed using Enhanced Multiple Scan (EMS) acquisition with a scan speed of 1000 amu/sec in the mass range from 400-1400 Da. LC-MS data were analyzed by "LC-MS reconstruct" in the MW range from 2700-3500 Da and by using several signal-to-noise filter settings to obtain the molecular weight and validity score of all peptide peaks. LC-MS/MS analyses were performed using Information Dependent Acquisition (IDA). The acquisition protocol used to provide mass spectral data for database searching involved the following procedure: mass profiling of the HPLC eluant using EMS; ions over the background threshold were subjected to examination using the Enhanced Resolution (ER) scan to confirm charge states of the multiply charged molecular ions. The most and next most abundant ions in each of these scans with a charge state of +2 to +4 or with unknown charge were subjected to CID using rolling collision energy. Enhanced product ion scan was used to collate fragment ions and present the product ion spectrum for subsequent database searches.

Enzymatic Digest and Peptide Sequencing Using Database Analysis.

C$_{18}$ prepurified O. affinis extract cyclotides were prepared for MS/MS sequencing as described earlier (Chen, 2005, J Biol Chem, 280, 22395-22405; Ireland, 2006, Biochem J, 400, 1-12). The extract was reduced, alkylated with iodoacetamide and enzymatic digested using trypsin or endoGluC (Sigma-Aldrich, Austria). Digested peptide extracts were analyzed with nano LC-MS/MS as described above and IDA data were used for further analysis. Database searching of LC-MS/MS data was carried out using the ProteinPilot™ software and the Paragon algorithm with the custom-made ERA database tool for the identification of cyclotides (Colgrave, 2010, Biopolymers, 94, 592-601).

Relative Quantification of Cyclotides Using Nano LC-MS Analysis.

C$_{18}$ prepurified O. affinis extract was separated by one dimensional nano LC-MS as described above. Cyclotide peaks were quantified by relative area under curve (all peaks at 214 nm absorbance from 15-55 min were processed) using the quantification wizard of Chromeleon 6.8 software. Peaks in the LC chromatogram were identified by molecular weight and retention time from corresponding LC-MS peaks. Quantification was performed on five independent LC-MS experiments and relative cyclotide abundance is presented as mean±SEM.

Preparation of Human Peripheral Blood Mononuclear Cells and Cell Culture.

Human peripheral blood mononuclear cells (PBMC) were isolated from the blood of healthy adult donors obtained from the Blood Transfusion Centre (University Medical Center, Freiburg, Germany). Venous blood was centrifuged on a LymphoPrep™ gradient (density: 1.077 g/cm$^3$, 20 min, 500×g, 20° C.; Progen, Heidelberg, Germany). Afterwards cells were washed twice with medium and cell viability and concentration was determined using the trypan blue exclusion test. PBMC were cultured in RPMI 1640 medium supplemented with 10% heat-inactivated fetal calf serum (PAA, Coelbe, Germany), 2 mM L-glutamine, 100 U/mL penicillin and 100 U/mL streptomycin (all from Invitrogen, Karlsruhe, Germany). The cells were cultured at 37° C. in a humidified incubator with a 5% CO$_2$/95% air atmosphere. All experiments conducted on human material were approved by the Ethics committee of the University of Freiburg.

Alternative Purification of Human Peripheral Mononuclear Cells (PBMCs).

PBMCs were isolated from blood samples of healthy adults that were provided by the transfusion center of the university hospital in Freiburg (Germany). Venous blood was diluted 1:2 (v/v) with PBS and centrifuged with a LymphoPrep-gradient (using 15 ml diluted blood and 20 ml LymphoPrep solution); density: 1.077 g/cm$^3$, 20 min, 500×g, 20° C.). The lymphocyte-enriched layer was transferred into a new vessel and washed three times with PBS and centrifuged again (10 min, twice with 300×g and last time with 800 rpm, 20° C.). For the following experiments, the cells were either stained with CFSE or diluted with medium to 4*10$^6$ cells/ml. Cells were counted in alight microscope using trypan blue staining and a hemocytometer.

Activation and Treatment of PBMCs.

PBMCs (10$^5$) were stimulated with anti-human CD3 (clone OKT3) and anti-human CD28 (clone 28.2) mAbs (both from eBioscience, Frankfurt, Germany) for 72 hrs in the presence of medium, the control agents camptothecin (CPT; 30 µg/mL: Tocris, Eching, Germany) and Triton-X 100 (0.5%; Carl Roth, Karlsruhe, Germany) or different concentrations of O. affinis extract, melittin (PolyPeptide, Strasbourg, France) or kalata B1, respectively. After cultivation, the cells were assessed in bioassays as described in the text.

Alternative Activation and Treatment of PBMCs.

Following purification, PBMCs were equilibrated for 2 h at 37° C. Afterwards 100 µl PBMCs (4*10$^6$ cells/ml) were pre-incubated in a 96-well plate for 2 h with CsA (cyclosporine A) or cyclotides, transferred to a new plate and stimulated with 10 µg/ml PHA-L for 1 h. This was followed by washing of each well with 100 µl PBS (centrifugation for 5 min, 1000 rpm, 20° C.) and re-suspending the cells in 100 µl medium for further assays.

Determination of Cell Proliferation and Cell Division.

For cell proliferation and cell division tracking analysis PBMC were harvested and washed twice in cold PBS and resuspended in PBS at a concentration of 5×10$^6$ cells/mL. Cells were incubated for 10 min at 37° C. with carboxyfluorescein diacetate succinimidyl ester (CFSE; 5 µM: Sigma-Aldrich, Taufkirchen, Germany). The staining reaction was stopped by washing twice with complete medium. Afterwards, the cell division progress was analysed using flow cytometric analysis.

Alternative Analysis of Cell Proliferation and Cell Division Using CFSE Staining.

Purified PBMCs (5*10$^6$ cells/ml) were incubated with 0.5 mM of the fluorescent dye CFSE (5-carbofluoreszeneinciacetat-succinylester) for 10 min at 37° C. The reaction was stopped using medium, cells were washed one time with medium by centrifugation (10 min, 300×g, 20° C.) and diluted with medium to 4*10$^6$ cells/ml.

Determination of PBMC Apoptosis and Necrosis Using Annexin V and Propidium Iodide Staining.

The levels of apoptosis were determined using the annexin V-FITC apoptosis detection kit (eBioscience, Frankfurt, Germany) according to the manufacturer's instructions. After annexin V staining, propidium iodide solution (PI; eBioscience) was added and the cells were incubated in the dark, followed by a flow cytometric analysis to determine the amount of apoptosis and necrosis. CPT (30 µg/mL) and Triton-X 100 (0.5%) was used as positive controls for apoptosis and necrosis, respectively.

Mice.

C57BL/6 mice (10-16 weeks old) were bred and maintained in the Monash University Animal Services facilities. All experiments were conducted in accordance with the Australian code of practice for the care and use of animals for scientific purposes (NHMRC, 1997), after approval by the Monash University Animal Ethics committee (Clayton/Melbourne, Australia).

Induction and Clinical Assessment of EAE.

A total of 200 µg of the encephalitogenic peptide MOG$_{35-55}$ (MEVGWYRSPFSRVVHLYRNGK; GL Biochem, Shanghai, China) emulsified in CFA (Sigma) supplemented with 4 mg/ml Mycobacterium tuberculosis (BD) was injected subcutaneously into the flanks. Mice were then immediately injected intravenously with 350 ng of pertussis vaccine (List Biological Laboratories, Campbell, U.S.A.) and again 48 hr later (Bernard J Mol Med 75, 1997, 77-88; Albouz-Abo Eur J Biochem 246, 1997, 59-70; Hvas Scand J Immunol 46, 1997, 195-203; Johns Mol Immunol 34, 1997, 33-38; Menon J Neurochem 69, 1997, 214-222). Animals were monitored daily and neurological impairment was quantified on an arbitrary clinical scale: 0, no detectable impairment; 1, flaccid tail; 2, hind limb weakness; 3, hind limb paralysis; 4, hind limb paralysis and ascending paralysis; 5, moribund or deceased (Liu Nat Med 4, 78-83 1998; Slavin Autoimmunity 28, 109-120 1998). Under recommendation of the animal ethics committee, mice were euthanised after reaching a clinical score of 4.

Antibodies and Recombinant Proteins.

The mouse anti-MOG mAb (clone 8-18C5) was purified from hybridoma culture supernatants on Protein G-Sepharose 4 Fast Flow column (GE Healthcare) according to the manufacturer's instructions. Antiserum to MOG$_{35-55}$ peptide (Ichikawa Int Immunol 8, 1996, 1667-1674; Ichikawa J Immunol 157, 1996, 919-926) was raised in rabbits by procedures similar to those described previously (Bernard Clin Exp Immunol 52, 1983, 98-106; Pedersen J Neuroimmunol 5, 1983, 251-259). The extracellular domain of mouse MOG (amino acid residues 1-117 of the mature protein) (rMOG) was produced in the E. coli strain M15pREP4 using the pQE9 expression vector (Qiagen, Australia) to incorporate an amino-terminal histidine tag as per manufacturer's instructions. A clarified bacterial lysate containing rMOG was loaded onto a Ni-NTA Superflow (Qiagen, Australia) column under denaturing conditions (6 M Guanidine-HCl, 100 mM NaH$_2$PO$_4$, 10 mM Tris pH 8.0,) as per the manufacturer's instructions using a BioLogic LP Chromatography System (Bio-Rad Laboratories, Australia). Bound protein was washed sequentially with Buffer A (8M Urea 100 mM NaH$_2$PO$_4$, 10 mM Tris pH 8.0), Buffer A (at pH6.3), 10 mM Tris pH 8/60% iso-propanol (to remove endotoxin) and again with Buffer A. Refolding of the bound protein was carried out by applying a linear gradient of Buffer A containing 14 mM 2-mercaptoethanol (100%-0%) vs. Buffer B (100 mM NaH$_2$PO$_4$, 10 mM Tris pH 8.0, 2 mM reduced glutathione, 0.2 mM oxidised glutathione) (0%-100%). This was followed by a second linear gradient of Buffer B (100%-0%) vs. Buffer C (100 mM NaH$_2$PO$_4$, 10 mM Tris pH 8.0) (0%-100%). The bound protein was eluted using Buffer C containing 300 mM Imidazole, then extensively dialysed against 50 mM NaCl/10 mM Tris pH 8. Protein concentration and purity were estimated using a Micro BCA assay (Bio-Rad Laboratories, Australia) and SDS-PAGE, respectively. The protein produced was varified as rMOG by western blot analysis using antibodies specific for native MOG. Endotoxin levels were determined using a Limulus Amebocyte Lysate assay (Associates of Cape Cod, Falmouth, Mass.).

Vaccination with MOG Peptide.

200 µg of the MOG peptide were emulsified with an equal volume of IFA (Difco) and injected subcutaneously in the upper flanks (100 µl divided equally) three weeks prior to the encephalitogenic challenge. This was followed by two more injections at weekly intervals (200 µg/IFA/100 µl).

Histopathology and Assessment of Inflammation, Demyelination and Axonal Damage.

At the completion of the experiments, mice were anesthetized, their blood collected (for subsequent antibody determination) and brain and spinal cord carefully removed, prior to immersion in a 4% paraformaldehyde, 0.1 M phosphate buffer solution. Segments of brain, cerebellum and spinal cord were embedded in paraffin. Sections were stained with haemotoxylin-eosin, Luxol fast blue and Bielshowsky for evidence of inflammation, demyelination and axonal damage, respectively (McQualter 2001 J Exp Med. October 1; 194(7), 873-82). Semiquantitative histological evaluation for inflammation and demyelination was performed and scored in a blind fashion as follows: 0, no inflammation; 1, cellular infiltrate only in the perivascular areas and meninges; 2, mild cellular infiltrate in parenchyma; 3, moderate cellular infiltrate in parenchyma; and 4, severe cellular infiltrate in parenchyma (Bettadapura *J Neurochem* 70, 199, 1593-1599 8; Okuda *J Neuroimmunol* 131, 2002, 115-125).

MOG-Specific Antibody Determination.

Antibody activity to rMOG and $MOG_{35-55}$ in mouse sera was measured by ELISA, as previously described Ichikawa *Cell Immunol* 191, 1999, 97-104). Briefly, serum was collected at the end of the experiments and tested by ELISA with rMOG and $MOG_{35-55}$ peptide-coated plates (Maxisorp, Nunc).

T Cell Proliferation and Cytokine Production.

Spleens were taken from mice sacrificed 32-46 days after $MOG_{35-55}$ immunization. Cells were gently dispersed through a 70 μm nylon mesh (BD) into a single cell suspension, washed and cultured at $2.5 \times 10^6$ cells/ml in complete RPMI (RPMI 1640 containing 10% heat-inactivated fetal calf serum (Sigma), 2 mM L-glutamine, 100 U/ml of penicillin, 100 μg/ml of streptomycin, 50 μm 2-mercaptoethanol and 1 mm sodium pyruvate. Two hundred microliters of cell suspensions were then added to 96 well microtitre plates either alone, with $MOG_{35-55}$ (20 μg/ml) or anti-CD3ε and anti-CD 28 (20 μg/ml each) and incubated for 66 h at 37° C. with 5% $CO_2$. Ten microliters of [$^3$H]thymidine (1 μCi/well; Amersham, Australia; diluted 1/10 in media) were added to each well for the last 18 h. Plates were harvested onto glass fibre filters and a drop of Microscint Scintillant (Perkin Elmer) was added to each well. Counts were read using a Top Count NXT Scintillation Counter (Perkin Elmer). Presented values are the mean of three wells. For cytokine assays, 2 ml of cells ($5 \times 10^6$ cells/ml) from spleens isolated 32-46 days after immunization were added to 24 well plates either alone or with $MOG_{35-55}$ (10 μg/ml) or with anti-CD3ε and anti-CD 28 (20 μg/ml each). Supernatants were collected at 48 and 72 h. Quantitation of mouse cytokine content incorporating Th1, Th2 cytokines and chemokines (IFNγ, IL-2, IL-3, IL-4, IL-5, IL-6, IL-9, IL-10, IL-12p70, IL-13, GM-CSF, KC, MCP-1, MIG, and TNF) were simultaneously determined using a multiplexed bead assay (Cytometric Bead Array Flex sets [CBA]) according to the manufacturer's recommended protocol (Becton Dickinson). Acquisition of 4500 events was performed using a FACScanto II flow cytometer (Becton Dickinson, San Jose, USA) and Diva software and data analysed and fitted to a 4-parameter logistic equation using the FCAP array software (Soft Flow, Pécs, Hungary). Minimum detection levels of each cytokine were: IFNγ, 5.2 μg/ml; IL-2, 1.5 μg/ml; IL-3, 4.2 μg/ml; IL-4, 0.8 μg/ml; IL-5, 4.8 μg/ml; IL-6, 6.5 μg/ml; IL-9, 10.5 μg/ml; IL-10, 16.4 μg/ml; IL-12p70, 9.2 μg/ml; IL-13, 7.3 μg/ml; GM-CSF, 9.9 μg/ml; KC, 16.2 μg/ml; MCP-1, 29 μg/ml; MIG, 11.4 μg/ml and TNF, 17.1 μg/ml.

IL-2 Surface Receptor Analysis.

Activated cells were transferred into a 96-well plate, centrifuged (5 min, 1000 rpm, 20° C.), washed one time with 100 μl FACS-buffer and stained with CD25 PE for 15 min at 4° C. Then cells were washed twice with FCS-buffer and resuspended in 100 μl FACS-buffer, transferred into FACS vials with a total volume of 250 μl and the expression of IL2 surface receptor CD25 was measured by FACS analysis using a FACSCalibur instrument (BD Biosciences).

Determination of Cytokine Release Using ELISA.

Activated cells were resuspended in 50 μl of medium, transferred into a 96-well plate and treated with 10 μg/ml PHA-L. After incubation for 24 h cells were re-stimulated with PMA (50 ng/ml) und ionomycin (500 ng/ml) for 6 h.

Next, the cells were transferred into Eppendorf tubes, centrifuged (5 min, 3000 RPM, 20° C.) und 50 μl of the supernatant was again transferred into new tubes and stored at −20° C. Production of cytokines was measured and quantified using the FlowCytomix™ kit according to manufacturer's instructions.

CD107a—Degranulation Analysis.

Activated cells were grown for 36 h and then treated for re-stimulation with PMA (50 ng/ml) und ionomycin (500 ng/ml) and stained with CD107a PE. After 1 h the reaction was stopped with 2 μl Golgi-Stop (1:10) and incubated for 2.5 h at 37° C. The cells were transferred into a 96-well plate, centrifuged (5 min, 1000 RPM, 20° C.) and washed with 100 μl FACS-buffer. Afterwards, PBMCs were stained with CD8 PE-Cy5 for 15 min at 4° C. and following to wash cycles with FACS-buffer the cells were resuspended in 100 μl, transferred into FACS vials with a total volume of 250 μl and the degranulation was measured by FACS analysis.

Intracellular Production of IFN-Gamma and TNF-Alpha.

Activated cells were grown for 36 h and then treated for re-stimulation with PMA (50 ng/ml), ionomycin (500 ng/ml) and brefeldin A for 6 h at 37° C. After transferring the cells into a 96-well plate, they were centrifuged (5 min, 1000 RPM, 20° C.) and washed with 100 μl FACS-buffer. Afterwards, PBMCs were stained with CD8 PE-Cy5 for 15 min at 4° C. and washed again twice with FACS-buffer. The cells were treated with 50 μl of 4% paraformaldehyde for 10 min at 4° C., washed twice with 100 μl FACS-buffer and then permeabilized by incubation with 100 μl Perm/Wash solution (1:10) for 15 min at 4° C. After centrifugation (5 min, 1000 rpm, 20° C.), PBMCs were incubated with IFN-gamma PE or TNF-alpha PE, respectively, for 30 min at 4° C. Free antibodies were washed away with Perm/Wash and PBMCs were re-suspended in 100 μl FACS-buffer. Production of IFN-gamma and TNF-alpha was individually determined by FACS analysis.

Total RNA Extraction and Reverse Transcription.

Total RNA was extracted from controls or treated cells ($2 \times 10^6$) frozen at −80° C. RNA-purification was performed according to the manufacturer's instructions for the RNeasy mini and Rnase-Free Dnase Set digestion kits (Qiagen, Hilden, Germany). The quantity and purity of extracted RNA was measured by spectrophotometry (Nanodrop, Peqlab, Erlangen, Germany) and purified RNA was reverse transcribed using the $RT^2$ First Stand Kit (Qiagen, Hilden, Germany).

Real-Time PCR.

RT-PCR reactions were carried out on a BioRad MyiQ (BioRad, Munich, Germany) in a final volume of 25 μL using $RT^2$ qPCR Primer Assay (for IL-2) and SYBR® Green qPCR Mastermix (both from Qiagen, Hilden, Germany). Each determination was done in duplicate and the housekeeping gene 18s rRNA was used as an internal control. The real-time thermal cycler program consisted of an initial denaturation step at 95° C. for 10 min followed by a two-step cycling program with 40 cycles (95° C., 15 s; and 60° C., 60 s). Results were expressed as relative gene expression of IL-2 and were determined by comparative Ct method. The data were normalized to the Ct value of the internal housekeeping gene 18s rRNA and the relative mRNA level in the untreated group (untreated PHA-L-activated) was used as calibrator.

Data Analysis and Statistical Analysis.

For FIG. 10, statistical analysis were performed using the Student's t test, with P values <0.05 considered significant. All other graphs were prepared using GraphPad Prism™ software and data are presented as mean±standard error (SEM). Where applicable, data were statistically analyzed using one-way ANOVA Kruskal Wallis test and Dunn's multiple comparison post analysis.

FACS graphs and results were prepared using CellQuest Pro Software (BD Biosciences) and are presented as mean+STDEV or SEM. All data pertaining examples 8-12 were statistically evaluated by ANOVA and Dunnet's post hoc-test using SPSS v19.0 (IBM, NY, USA).

EXAMPLE 2: CHEMICAL ANALYSIS OF OLDENLANDIA AFFINIS PLANT EXTRACT

The crude extract of the coffee-family plant *Oldenlandia affinis* was chemically analysed using a rapid peptidomics workflow utilising nano-LC-MS, peptide reconstruct with database identification and MS/MS automated sequence analysis to determine its cyclotide content.

*O. affinis* plants were grown and the aerial parts were isolated according to well-known laboratory protocols using overnight extraction with dichloromethane and methanol followed by $C_{18}$ solid phase extraction of the aqueous part. This standard procedure commonly yields many grams of crude cyclotide-extract per kilogram of fresh plant leaf weight (Gruber, 2007, Toxicon, 49, 561-575; Gran, 1970, Medd Nor Farm Selsk, 12, 173-180), while the content of various cyclotides depends on the growth conditions (e.g., habitat) of the plants and other environmental factors (Trabi, 2004, J Nat Prod, 67, 806-810; Seydel, 2007, Appl. Microb. Biotechnol., 77, 275-284).

Generally, amino acid sequencing is only feasible from pure or semi-purified cyclotide fractions. Therefore, an alternative peptidomics approach was used to dissect the cyclotide content from a crude plant extract by combining nanoflow LC-MS and peptide reconstruction (identification by molecular weight) as well as proteolytic digestion, LC-MS/MS and automated database analysis (identification by amino acid sequence) using the recently reported ERA cyclotide database tool (Colgrave, 2010, Biopolymers, 94, 592-601). The crude cyclotide extract was analyzed with various linear gradients on reversed-phase $C_{18}$ nano LC coupled online to an electrospray ionization hybrid triple-quadrupole/linear ion-trap (ESI-QqLIT) mass spectrometer, which was operated in enhanced MS mode with scan speeds of 1000 and 4000 amu/sec, respectively. Application of an automated LC-MS reconstruct tool yielded initially a few hundred of peptide masses in the range from 2700-3500 Da (typical MW for cyclotides). The high number likely accounts for some false-positive hits due to the inclusion of low abundant data in the calculation. Hence, the signal-to-noise factor in the algorithm was adjusted and usually between 50-100 reconstructed peptide masses with significant scores above 0.99 were obtained. Representative LC-MS reconstructed data (of at least three independent experiments) are listed in Table 4. A total of 72 peptide masses in the range from 2700-3500 Da were identified. By comparing those peptide masses to the database of cyclotides (CyBase (Wang, 2008, Nucleic Acids Res, 36, D206-210)), 23 known *O. affinis* cyclotides, 24 peptide masses that correspond to peptides from other cyclotide plant species and 25 new (not previously described) cyclotide masses were identified. LC-MS experiments were further analyzed with manual peptide reconstruction by extracting the doubly- and triply-charged ions of respective cyclotide peaks and by calculation of the average molecular weight (unpublished data). The manual analysis was useful as an internal control to ensure the integrity of the generated automated data.

In addition to the analysis of *O. affinis* cyclotides by molecular weight and database comparison, a number of chemical modifications of the crude extract, i.e. reduction and alkylation followed by trypsin and endo-GluC proteolysis, were performed. Due to the structural nature and high stability of cyclotides these chemical modifications are necessary to yield amenable precursor ions for MS/MS sequencing. The modified and digested mixtures were analyzed with a peptidomics workflow utilizing nano LC and peptide sequencing by Information Dependent Acquisition (for further details see the Methods Section). The resulting MS and MS/MS data were used for automated cyclotide identification using the ParagonTM algorithm with a custom-made ERA cyclotide database (a tool that is freely available on the web). Using this cyclotide peptidomics analysis, 14 known cyclotides could be identified by amino acid sequence (see Table 5). In summary, using the above described peptidomics workflow nearly all currently known cyclotides and an even greater number of novel peptide masses corresponding to other known or novel cyclotides (by molecular weight) could be identified in crude cyclotide extract from the plant *O. affinis* (see Table 1).

The combination of nano LC-MS/MS and LC-MS reconstruction, as well as automated database searching is a rapid and useful technique for the identification of cyclotides in crude extracts. Compared to an earlier study from Plan et al. (Plan, 2007, ChemBioChem, 8, 1001-1011), which described the first cyclotide fingerprint of *O. affinis* using classical peptide purification via analytical HPLC and offline MS/MS sequencing, 8 additional known cyclotides have been identified and a list of ~50 peptide masses has been provided corresponding to cyclotides of which some can be identified by peptide fingerprint analysis in CyBase (the cyclotide database (Wang, 2008, Nucleic Acids Res, 36, D206-210)). This suggests that the number of cyclotides to be found in a single species may be >70 and is, therefore, at least twice the number than earlier anticipated (on average 34 cyclotides per species (Gruber, 2008, Plant Cell, 20, 2471-2483). This, of course, has a huge impact on the determination of the overall number of cyclotides in the plant kingdom and consequently would lead to a necessary revision of the number of novel cyclotides to be discovered in plants.

EXAMPLE 3: ANTI-PROLIFERATIVE EFFECTS OF *O. AFFINIS* CYCLOTIDE EXTRACT

After completion of the chemical analysis, different concentrations of the crude *O. affinis* cyclotide extract were tested for its anti-proliferative capacity on activated human primary PBMC (FIG. 2). By using flow cytometric-based forward-side-scatter analysis, it was demonstrated that the extract exhibits a dose-dependent (50-100 μg/mL) decrease of activated proliferating PBMC compared to untreated stimulated control (FIGS. 2A and B). Simultaneously, a constant content of viable, resting PBMC, without accumulation of dead cells were observed, showing that the applied concentrations of the cyclotide extract are not harmful to the cells. Above this concentration range, the extract showed an increasing cytotoxic effect. Along this line, camptothecin (CPT, 30 μg/mL), which was used as positive inhibitory proliferation control, induced a high proportion of dead cells, indicating that the observed anti-proliferative effect, in contrast to the *O. affinis* cyclotide extract, was mainly due to cytotoxicity.

The impact of the crude *O. affinis* cyclotide preparation on the cell division level of activated PBMC was further evaluated. For this purpose, the cells were labeled with the dye carboxyfluorescein diacetate succinimidyl ester (CFSE), which does not influence the viability of the stained cells and is inherited by daughter cells after cell division and each dividing cell consequently loses fluorescent intensity. These data, shown in FIGS. 2C and D, indicate that the extract caused a dose-dependent inhibition of cell division of activated PBMC, which confirms that the crude *O. affinis* cyclotide preparation has the ability to inhibit PBMC proliferation without cell damage.

EXAMPLE 4: RELATIVE QUANTIFICATION OF CYCLOTIDES AND ISOLATION OF KALATA B1

Since promising anti-proliferative activity of the total cyclotide extract from *O. affinis* was obtained, the relative amount of the major cyclotides was determined and the main components for biological characterization were further purified. For this purpose the crude cyclotide extract was used for quantitative nano LC-MS analysis, similar as described above. Diluted aliquots of the extract were separated by nano $C_{18}$ RP-HPLC coupled online to the mass spectrometer. Eluted peptides were monitored both with absorbance at 214 nm and by molecular weight. The area-under-curve of the major cyclotide peaks in *O. affinis* was determined by automated integration (and if necessary manual post-processing). The relative quantification analysis of the cyclotide content has been carried out from five independent LC-MS experiments (see Table 6) and a representative *O. affinis* elution profile, indicating the major cyclotide peaks and their relative abundance (mean±SEM), is shown in FIG. 3.

As presented above, and in agreement with earlier studies (Plan, 2007, ChemBioChem, 8, 1001-1011), the cyclotides kalata B1 and kalata B2 are the main peptide components, accounting for approx. 34% of the overall cyclotide content in *O. affinis*. Kalata B1 and B2 differ by only five amino acid positions (see FIG. 6), namely Val to Phe (loop 2) and conservative replacements of Thr to Ser (loop 4), Ser to Thr (loop 5), Val to Ile (in loop 5) and Asn to Asp (in loop 6) in kalata B2. Since these substitutions have no significant structural consequences ($RMSD_{backbone\ kB1/kB2}$=0.599 Å, see FIG. 6) and since the two peptides have a similar bioactivity profile (Gruber, 2007, Toxicon, 49, 561-575), kalata B1 (comprising ~14% of total extract) was used for further biological analysis and its anti-proliferative potential on activated human primary PBMC.

EXAMPLE 5: ANTI-PROLIFERATIVE AND CYTOTOXIC EFFECTS OF KALATA B1

To analyze whether kalata B1 has the capacity to inhibit the proliferation of activated human primary PBMC, the cells were labeled with the fluorescent dye CFSE and analyzed the cell division properties in the presence of the kalata B1 concentrations in the range from 1.8 to 14 µM using flow cytometry. After exposure of PBMC to kalata B1, a dose-dependent decrease of the cell division capacity was observed, as compared to untreated stimulated PBMC controls, as shown in FIG. 4. The inhibitory concentration $IC_{50}$ for the anti-proliferative effect of kalata B1 was 3.9±0.5 µM (FIG. 7), which compares to other effects of kalata B1, such as nematocidal (Huang, 2010, J Biol Chem, 285, 10797-10805) and cytotoxic activities (Svangard, 2004, J Nat Prod, 67, 144-147; Lindholm, 2002, Mol Cancer Ther, 1, 365-369; Daly, 2004, FEBS Lett, 574, 69-72) as has been summarized in Table 3.

To analyze whether the anti-proliferative effect was due to cell damaging, the influence of kalata B1 on the induction of PBMC apoptotic or necrosis was examined (FIG. 5). Cellular apoptotic and necrotic hallmarks were measured by using inter-nucleosomal DNA fragmentation ($subG1^+$ cells) assay and phosphatidylserine surface analysis through a single and combinatory annexin V and propidium iodide staining. This double staining process allowed the discrimination between viable ($annexin^-/PI^-$), apoptotic ($annexin^+/PI^-$ and $annexin^+/PI^+$) or necrotic ($annexin^-/PI^+$) cells. The data shown in FIG. 5A to C demonstrate that kalata B1 had no significant influence on the induction of apoptosis. Necrosis was slightly increased at higher concentration (14 µM) of kalata B1, compared to untreated control (FIG. 5D). The positive controls for apoptosis and necrosis, CPT (30 µg/mL) and detergent (Triton-X 100), respectively, significantly increased the fractions of these cells.

The anti-proliferative activity of kalata B1 triggered validation and control experiments to determine the nature of the observed effect. Cytometric-based forward-side-scatter analysis (data not shown) provided solid evidence that the anti-proliferative effect induced by the cyclotide does not cause cell death by either apoptosis or necrosis, but inhibits the growth of the lymphocytes in a cytostatic fashion. Concentrations higher than 14 µM of the peptide are cytotoxic to the cells (data not shown). This was expected since kalata B1 has earlier been reported to cause hemolysis and membrane disruption at concentrations above ~50 µM (Barry, 2003, Biochemistry, 42, 6688-6695; Henriques, 2011, J Biol Chem, 286, 24231-24241). Therefore, control experiments were performed with the honeybee venom component melittin, a commonly used strong membrane disrupting peptide agent.

Concentrations were tested, at which cytotoxic effects on human lymphocytes were described in the literature, to ensure that our experimental setup was sensitive enough to detect possible cytotoxic effects of kalata B1 (Pratt, 2005, In Vitro Cell Dev Biol Anim, 41, 349-355) (see FIG. 8). The data revealed that in contrast to kalata B1, melittin induced a decrease of proliferating PBMC at 1.6 µM (FIG. 8A), but this effect was mainly due to the induction of apoptosis, as indicated by the results of the inter-nucleosomal DNA fragmentation analysis (FIG. 8B) and by induction of specific apoptotic cells at these concentrations (FIG. 8C). In addition, there was a slight effect on necrosis induction at high concentrations of melittin (FIG. 8D).

From these control data, it was concluded that kalata B1, in contrast to melittin, has an anti-proliferative capacity, which is not due to cytotoxic effects and the membrane lysing capacity of kalata B1, as otherwise one would have expected similar observations from the much more potent cytotoxic peptide melittin. The proof of anti-proliferative effects by holding the cells in an "inactive" state at which they are still viable, but aren't able to grow and proliferate without causing cell death in a certain dose range is a crucial precondition to classify a substance as immunosuppressant, because cytotoxicity would cause side effects.

EXAMPLE 6: TEST OF CYCLOTIDE MUTANTS/VARIANTS IN ANTI-PROLIFERATIVE ASSAYS ON PBMCS AND ISOLATED T-LYMPHOCYTES

The anti-proliferative effect of cyclotide mutants/variants was tested according to Example 5. In brief, CFSE-labelled PBMCs, or magnetic-purified CD3+ lymphocytes were stimulated with anti-CD3/28 mAbs, in the presence of medium (ctrl), camptothecin (CPT, 30 µg/mL), cyclosporin A (CsA, 1 µg/mL) or different concentrations of cyclotides (1.8-14 µM) for 72 h. Afterwards the cell proliferation was assessed by analysing cell division using flow cytometric-based histogram analysis. The following peptides (1.8-14 µM) on both PBMCs and CD3-purified T-lymphocytes (n≥2) have been tested:

```
Kalata B1:       GLPVCGETCVGGTCNTPGCTCSWPVCTRN

Kalata B2:       GLPVCGETCFGGTCNTPGCSCTWPICTRD

D-kalataB2: all-D  GLPVCGETCFGGTCNTPGCSCTWPICTRD

Kalata T8K:      GLPVCGEKCVGGTCNTPGCTCSWPVCTRN

Kalata V10A:     GLPVCGETCAGGTCNTPGCTCSWPVCTRN

Kalata V10K:     GLPVCGETCKGGTCNTPGCTCSWPVCTRN

Kalata G18K:     GLPVCGETCVGGTCNTPKCTCSWPVCTRN

Kalata N29K:     GLPVCGETCVGGTCNTPGCTCSWPVCTRK

Kalata T20K, G1K:  KLPVCGETCVGGTCNTPGCKCSWPVCTRN

Kalata T20K:     GLPVCGETCVGGTCNTPGCKCSWPVCTRN
```

The corresponding $IC_{50}$ values can be found in Table 2:

TABLE 2

Comparison of kalata B1 (and other cyclotides) inhibitory effects on PBMC and CD3 purified T-lymphocyte proliferation.

| Peptide | $IC_{50}$ (µM) ± STDEV | Relative activity in other assays (fold difference to kB1) | | |
|---|---|---|---|---|
| | | nematocidal | hemolytic | insecticidal |
| PBMCs | | | | |
| Kalata B1 | 2.9 ± 1.3$^a$ | 1.0 | 0.7 | 1.0 |
| Kalata B2 | 0.2 ± 0.1$^c$ | — | — | — |
| all-D kalata B2 | 2.3 ± 0.8$^c$ | — | — | — |
| Kalata B1 T8K | not active (n.a.)$^b$ | <0.2 | T8A: 0.1 | 0.2 |
| V10A | n.a.$^b$ | — | 0.5 | 1.1 |
| V10K | n.a.$^b$ | <0.2 | — | — |
| G18K | 4.4 ± 0.5$^b$ | 2.4 | G18A: 0.6 | 1.2 |
| N29K | 3.2 ± 0.6$^b$ | 7.0/3.8 | N29A: 0.5 | 1.0 |
| T20K, G1K | 1.9 ± 0.1*$^b$ (cytotoxic) | 6.5/6.8 | — | — |
| T20K | 1.9 ± 0.6$^c$ | 3.0/2.6 | — | — |
| MCo59 | n.a.$^b$ | — | — | — |
| MCo-CC1 | n.a.$^b$ | — | — | — |
| MCo-CC2 | n.a.$^b$ | — | — | — |
| CD3 purified lymphocytes | | | | |
| Kalata B1 | 2.4 ± 0.5$^d$ | — | — | — |
| Kalata B2 | 0.6 ± 0.02$^d$ | — | — | — |
| all-D kalata B2 | 2.9 ± 0.4$^d$ | — | — | — |
| G18K | 3.2 ± 1.8$^c$ | — | — | — |
| N29K | 2.1 ± 0.9$^c$ | — | — | — |
| T20K, G1K | 1.1 ± 0.7$^c$ (cytotoxic) | — | — | — |
| T20K | 2.7 ± 0.6$^d$ | — | — | — |

*this compound is cytotoxic at 14 µM; all data have been normalized and analyzed with non-linear regression (fixed slope) using Graph Pad,
$^a$n = 7,
$^b$n = 4,
$^c$n = 3,
$^d$n = 2;
peptides other than kalata B1, have been supplied by David Craik (Institute for Molecular Bioscience, Australia).

EXAMPLE 7: IN VIVO ACTIVITY IN EAE MOUSE MODEL OF MS

The in vivo activity of cyclotides in the EAE mouse model of MS were tested, as described previously (Okuda J Interferon Cytokine Res 18, 1998, 415-421). The ability of mice to recover from motor deficit after developing a chronic progressive form of EAE was examined by vaccinating the mice with kalata B1. MOG MS-like disease model in C57BL/6 mice (Bernard J Mol Med 75, 1997, 77-88) was used, where adult female C57BL/6 (10-12 weeks old) mice were vaccinated with three successive subcutaneous (sc) injections of cyclotides (200 mg each time) in incomplete Freund's adjuvant (IFA) at weekly intervals before EAE was induced with $MOG_{35-55}$. Control mice were similarly treated but received PBS in IFA. Animals were assessed daily for clinical signs of EAE for a period of 43 days.

Vaccination with kalata B1 resulted in a reduction in the incidence and severity of EAE (FIG. 10A). Mice treated with kalata B1, displayed significantly milder clinical signs (mean cumulative score 42.2±13.0; p<0.01) as compared to the PBS control group (cumulative score: 96.6±7.1; disease duration: 29.1±0.9).

The influence of kalata B1 vaccination on the formation of CNS inflammatory and demyelinating lesions was examined by histological studies of fixed tissue using haemotoxylin/eosin, Luxol fast blue (LFB) and Bielshowsky silver staining. The CNS of all mice treated with PBS showed extensive inflammatory lesions, characterized by mononuclear inflammatory cells, which were particularly florid in the cerebellum and spinal cord (FIG. 10B). LFB and Bielshowsky silver staining revealed marked myelin loss and severe axonal injury, respectively, particularly around the lesioned tissue in all three CNS regions examined. Kalata B1 treated mice displayed some improvement in disease severity as judged by decrease in histological lesions of EAE (FIG. 10B).

The capacity of spleen cells to proliferate in response to the encephalitogen $MOG_{35-55}$ to determine whether the suppressive effect on EAE following vaccination with kalata B1 was associated with a decrease in MOG-specific T cell responses. Furthermore, to address whether this suppression of EAE was antigen specific and/or the result of a defect in the activation or function of T-cells, the same population of splenocytes was stimulated by the polyclonal activators, anti-CD3 and anti-CD28 antibodies. FIG. 10C shows that regardless of the treatment regimen, splenocytes from all vaccinated mice proliferated to MOG with stimulation indices (SI) of 2.9±0.4 and 2.7±0.5 for groups treated with kalata B1 and PBS, respectively. These splenocytes displayed strong proliferative responses to the anti-CD3/CD28 antibodies with SI ranging from 17 to 47.

Whether the suppression of EAE in mice vaccinated with kalata B1 was associated with a decrease in the production of specific antibodies to MOG was examined. Accordingly, sera from kalata B1 and PBS treated mice were collected at the completion of the experiment (Day 43) and tested for their reactivity to $MOG_{35-55}$. As indicated in FIG. 10D, anti-MOG antibodies were detected in all sera regardless of the vaccination regimen.

It is well established that the development of EAE is associated with the secretion of proinflammatory cytokines by CNS-antigen specific T cells (Owens Curr Opin Neurol 16, 2003, 259-265). Since the suppression of EAE following kalata B1 vaccination was not associated with a decrease in T cell reactivity to MOG, it was investigated whether MOG-reactive T cells in protected animals may have switched to an anti-inflammatory T cell phenotype. Accordingly, conditioned media generated from in vitro stimulated and non-stimulated spleen cell cultures were assessed in cytokine bead array assays. A total of 15 cytokines were analysed simultaneously, including, IL2, IL3, IL4, IL5, IL6, IL9, IL10, IL12p70, IL13, IFNγ, GM-CSF, KC, MCP1, MIG and TNFα. There were no marked changes in cytokine content in $MOG_{35-55}$ or CD3/38-stimulated supernatants between cyclotide and control animal groups (data not shown). In contrast, significantly reduced levels of the chemokine MIG known to play a role in T cell trafficking and TNFα, a pro-inflammatory cytokine known to be involved in the pathogenesis of EAE Nicholson Curr Opin Immunol 8, 1996, 837-842) were demonstrated in non-stimulated spleen cell supernatants generated from animals treated with kalata B1 (FIGS. 10E and 10F). On the basis of this cytokine profile, it can be deduced that vaccination with cyclotide, leads to the production of an anti-inflammatory T response.

EXAMPLE 8: INFLUENCE/EFFECT OF VARIOUS CYCLOTIDES ON THE EXPRESSION OF IL-2-ALPHA-CHAIN CD25

Amongst other pathways, T-cell proliferation is determined by binding of the cytokine IL-2 to its cell surface receptor. Therefore the influence of cyclotides on the expression of the IL-2 receptor was tested. The test compounds were T20K, V10A, V10K and T8K and hence PBMCs were treated with these cyclotides, following stimulation with PHA-L in order to determine the expression of the IL-2 surface receptors CD25 after 24 and 48 hours of cultivation, respectively, using FACS analysis (FIG. 11). As control substance CsA was used. Treatment of PBMCs with CsA leads to a reduction in CD25 surface expression and yields 76%±10.7 after 24 hours and treatment with T20K yields 79%±10.1 as compared to untreated cells, i.e. stimulated PBMCs (CTRL, 100%) (FIG. 11B). Treatment with V10A yields 114%±12.5, V10K yields 112%±16.3 and T8K yields 114%±17.3 CD25 surface expression after 24 h as compared to the control (FIG. 11B). This trend continues after 48 h, i.e. the CD25 expression is further reduced by treatment with CsA (62%±7.3) and T20K (46%±18.2) whereas treatment with V10A, V10K und T8K leads to no significant change in receptorexpression (FIG. 11C und D). In summary, treatment with CsA ($p \leq 0.01$) and the cyclotide T20K ($p \leq 0.001$) leads to a significant reduction of CD25 expression, whereas the cyclotides V10A, V10K und T8K do not influence the expression level of the CD25 receptor.

EXAMPLE 9: INFLUENCE OF CYCLOTIDES ON IL-2 RELEASE AND GENE EXPRESSION

To analyze the mechanism of cyclotide-mediated anti-proliferation of T-lymphocytes, their effect on the direct release of IL-2 in PBMCs was determined. The cells were treated with a cyclotide and activated with PHA-L. After 24 h the cells were re-stimulated with PMA and ionomycin and the IL-2 concentration in the supernatant (released IL-2) was measured with an ELISA-based FACS methodology (FIG. 12A). The IL-2 release was significantly ($p \leq 0.01$) reduced by treatment with CsA (18%±15.7) and T20K (24%±18.6) as compared to the control cells. The cyclotide V10K had no effect on the release of IL-2 (data not shown).

Moreover, supernatants of stimulated T-cells were analyzed for their IL2 release using a human IL-2 ELISA Kit from eBioscience according to the manufacturer's instructions. The color reaction was evaluated at an optical density of 450 nm by the microplate reader Synergy H4 (BioTek) (FIG. 12B).

To determine whether cyclotides have an impact at the gene expression level of the, il-2 gene expression (as control we used 18s rRNA) in PBMC cells was investigated by quantitative real-time PCR (FIG. 12C). Cyclotide T20K clearly decreases the level of IL-2 mRNA in contrast to the control, whereby as positive inhibition control we used cyclosporine A.

EXAMPLE 10: INFLUENCE OF EXOGENOUS IL-2 ADDITION TO CYCLOTIDE-TREATED PBMCS

To determine the validity of the significant reduction of IL-2 release after cyclotide treatment, the influence of exogenous addition of IL-2 post treatment was tested. If IL-2 synthesis is reduced by treatment with CsA and cyclotides, one would expect that this effect can be reversed by exogenous addition of IL-2 to the treated cells. Therefore, PBMCs were treated with cyclotides and CsA and the cells were activated with PHA-L. In parallel, the cells were grown with addition of exogenous IL-2 (FIG. 13). Pretreatment of PBMCs with CsA and cyclotide T20K leads to an anti-proliferative effect (13%±17.6 and 29%±24, respectively) as compared to the control cells (FIG. 13A und B), whereas treatment with the cyclotides V10A, V10K and T8K has no effect on the proliferation. By adding exogenous IL-2 it was possible to reverse the anti-proliferative effect of CsA in part (54%±19.3) and of T20K almost completely (91%±1.4) (FIG. 13C und D). Addition of IL-2 to the V10A-, V10K- or T8K-treated PBMC, did not change the effect on proliferation (FIG. 13).

EXAMPLE 11: INFLUENCE OF CYCLOTIDES ON THE IFN-GAMMA OR TNF-ALPHA PRODUCTION

From the results so far it is evident that treatment of activated PBMCs with CsA or cyclotide T20K influences the expression of the IL-2 surface receptor CD25 (FIG. 11) as well as the IL-2 secretion (FIG. 12). Furthermore, the anti-proliferative effect of T20K on PBMCs can be antagonized by addition of exogenous IL-2 (FIG. 13). Therefore it is of interest to determine whether cyclotides only have anti-proliferative effects or also affect the effector function of T-lymphocytes, which would directly relate to changes in the IFN-gamma and TNF-alpha production. Therefore, the production of both cytokines of cyclotide-treated, activated PBMCs at an early time point after PBMC activation was tested. PBMCs were pre-treated with either CsA or cyclotides followed by activation with PHA-L. After 24 h, the cells were re-stimulated for 6 h with PMA and ionomycin and afterwards the concentrations of IFN-gamma (FIG. 14) and TNF-alpha (FIG. 15) in the cell supernatant was measured using an ELISA-based FACS method. The IFN-gamma concentration of the CsA-treated cells was reduced to 14%±3.4 as compared to the control and also the treatment with cyclotide T20K yielded in an IFN-gamma reduction (21%±13.2). In summary, the IFN-gamma production after 24 h was significantly reduced by CsA ($p \leq 0.01$) and T20K ($p \leq 0.001$) (FIG. 14) but not by V10K (data not shown).

CsA (23%±1.8) and T20K (23%±10.6) also led to a significant (p.5_0.001) reduced TNF-alpha expression as compared to the control (FIG. 15). To test whether the effector function of T-cells remains compromised after treatment with T20K we measured IFN-gamma and TNF-alpha release at a later time-point, i.e. 36 h past stimulation. The CsA-treated cells experienced a significant (p≤0.01) reduction in IFN-gamma production of 23%±2 as compared to the control (FIG. 14) whereas all cyclotides (T20K, V10A, V10K, T8K) did not induce significant changes in the level of IFN-gamma (FIG. 14). TNF-alpha production was significantly (p≤0.001) reduced after treatment with CsA (20%±14.4) whereas all cyclotide-treated cells did not result in any changes in the TNF-alpha level (FIG. 15). Therefore it is obvious that treatment with cyclotide T20K leads to an initial reduction of the effector function, as indicated by the reduced IFN-gamma and TNF-alpha production, but the level of both cytokines stabilizes over time. This further indicates that T20K and CsA have different mechanism of action.

EXAMPLE 12: INFLUENCE OF CYCLOTIDES ON THE DEGRANULATION ACTIVITY OF ACTIVATED PBMCS

After determining the influence of cyclotide treatment on the effector function of PBMCs on the basis of measuring IFN-gamma and TNF-alpha cytokine levels, it is of interest to determine an effect of cyclotides on the degranulation activity. Activation of cytotoxic $CD8^+$-lymphocytes lead to a release of cytolytic granules, which contain/express lysosomal-associated membrane protein 1 (CD107; LAMP-1). During degranulation, the granule vesicle membranes fuse with the membranes of activated $CD8^+$-lymphocytes and therefore LAMP-1 can be used as a marker protein for the cytotoxic activity of T-lymphocytes, which can be measured with FACS. After 36 h, 42%±21.4 of the CsA- and 49%±16.8 of the T20K-treated cells contain the degranulation marker LAMP-1 as compared to the control (FIG. 16). This can be interpreted in the way that CsA- and T20K-treated cells have reduced cytotoxicity. Cyclotides V10K and T8K had no influence on the degranulation activity of activated PBMCs (data not shown).

EXAMPLE 13: $CA^{2+}$ RELEASE OF JURKAT CELLS

Jurkat cells T-cells were treated as described for FIG. 17, supra. For Jurkat cells CsA (5 mg/mL), T20K (4 µM) and V10K (4 µM) stimulation did not induce a change in $Ca^{2+}$ signaling in Jurkat cells. Since neither CsA nor cyclotides lead to any changes in $Ca^{2+}$ signalling it is evident that either compound will act downstream of $Ca^{2+}$ release and hence this indicates a similar immunosuppressive mechanism of cyclotides in comparison to CsA in these cells. In contrast human primary T-cells demonstrate an increasing $Ca^{2+}$ release after incubation with the cyclotide T20K and hence the mechanism of action may be cell type dependent.

EXAMPLE 14: EFFECT OF CYCLOTIDES ON C57BL/6J MICE

Materials

Seven weeks old female C57BL/6J mice were purchased from the Department for Lab-zoology and -genetics (Himberg, Austria). All experiments were approved according to the European Community rules of animal care with the permission of the Austrian Ministry of Science. T20K and V10K were provided by D. J. Craik, from the University of Queensland, Institute for Molecular Bioscience (Brisbane, Australia). 5-carboxyfluoresceine-N-hydroxysuccinimid was purchased from Sigma-Aldrich (Vienna, Austria).

Immunization

Mice (n=10/group) were treated on day (−7), 0, 7 with 200 µg/100 µL/mouse T20K solubilized in sterile PBS intraperitoneally (i.p.), as indicated in the figure. On day 0 they were immunized subcutaneously with myelin oligodendrocyte glycoprotein ($MOG_{35-55}$, 1 mg/mL) and complete Freud's adjuvant (CFA, 10 mg/mL) mixed at equal parts. Therefore 70 µL were injected into the left and right flank. Additionally mice received 100 µL pertussis toxin (2 µg/mL) i.p. on day 0 and again on day 2. Beginning at day 10 mice were scored every second day. Weight was also measured at day (−7), 0, 7 and on the same day during scoring. Mice were sacrificed on day 24 after reaching high scores.

Spleenocyte Isolation and Stimulation

Spleens of sacrificed mice were taken and transferred into a 6 cm Petri Dish with 5 mL sterile PBS. To receive a spleenocyte suspension, spleens were meshed and filtered through 70 µm nylon sieve. Cells were centrifuged at 1200 rpm for 5 minutes and resuspended in RPMI 1640 media supplemented with 10% fetal calf serum (FCS), 2 mM L-glutamine, penicillin (100 U/mL), and streptomycin (100 µg/mL). Spleenocytes were cultivated at a concentration of $3 \times 10^6$/mL in a 48-well flat-bottom plate (500 µL/well). Cells were stimulated with 30 µg/mL $MOG_{35-55}$ or left untreated and incubated at 37° C. for three days. Supernatants and cells were taken stored at −20° C. until further experiments. Cells isolated from the naïve mouse group were additionally cultivated in a 96-well flat-bottom plate (100 µL/well) and stimulated with T20K (4 µM), T20K+MOG, T20K (12 h), V10K (4 µM, 12 h), CsA (5 µg/mL; 12 h), MOG (12 h) or left untreated. After 12 hours MOG or T20K was added to appropriate wells. Supernatants were stored after 24 hours and after 48 hours at −20° C.

Enzyme Linked Immunosorbent Assay

Supernatants of stimulated spleenocytes were analyzed for their IL2, IL17, INFγ, IL4 and IL22 cytokine release using anti-mouse antibodies for ELISA from eBioscience according to the manufacturer's instructions. The color reaction was evaluated at an optical density of 450 nm by the microplate reader Synergy H4 (BioTek).

SDS-PAGE and Western Blotting for NFAT1c

Human T-cells provided by CCRI from A. Dohnal, PhD were stimulated according to the protocol for IL2 release described above. Stimulated cells were resuspended in TBS and mixed at equal parts with sample buffer and heated for five minutes at 95° C. A sodium dodecyl sulfate polyacrylamide gel was prepared to separate the proteins achieved from the lysed T-cells. After electrophoresis proteins were transferred from the gel to a membrane. After blocking the membrane with BSA 3% in TBST over night at 4° C., the first antibody mouse anti-NFATc1 was incubated for 2 hours at room temperature. After five times washing with TBST 0.1% Tween, the membrane was incubated with the second antibody anit-mouse IgG HRP for one hour at room temperature. The membrane was dried and treated with West Pico or West Femto Super Signal Solution according to the manufactures protocol to evaluate the chemo-luminescence signal.

EXAMPLE 15: CELL PERMEABILITY OF T20K CYCLOTIDES (CHEMICAL LABELLING AND MICROSCOPY)

1.5 mg of T20K was dissolved in 1.5 ml of 100 mM sodium carbonate buffer of pH 8.8. 5-carboxyfluoresceine-N-hydroxysuccinimid ester (5-CFSE) was added in 10 fold excess as solid compound (2.5 mg) The reaction was allowed to proceed for 120 min at room temperature. Afterwards the reaction mixture was heated to 50° C. for 30 min to complete the hydrolysis of the N-hydroxysuccinimid ester (NHS). Purification was performed using semi-preparative chromatography, applying a Kromasil RP column 250×10 ID, 5 µm 100 Å. Eluent A was ddH$_2$O/TFA 99.9/0.1% (v/v), eluent B was AcN/H$_2$O/TFA 90/10/0.08% (v/v/v). The linear gradient from 5% eluent B to 80% eluent B in 50 min was used. Maldi-TOF-MS analysis of the collected fractions yielded a mass of 3276.3 Da in one of the fractions. The mass peak of 3276.3 Da were identified as the mono-derivatized species of T20K with 5-carboxyfluoresceine with a mass shift of 357 Da. Human T-cells and Jurkat cells were incubated with a 4 µM solution of the T20K derivative in RPMI 1640 media supplemented with the additives described above for 20 min. The fluorescence microscope was from Zeiss LSM 510 confocal microscope. The excitation wavelength was 488 nm and emission wavelength 520 nm.

EXAMPLE 16

The present invention refers to the following supplemental tables:

TABLE 1

Cyclotides from *O. affinis* extract identified by nano LC-MS and MS/MS

| Cyclotide[1] | MW (avg.) Da[2] | MW (mono.) Da[2] | Score[3] | Evidence[4] | Theoretical MW Da[5] | Δ MW Da[6] |
|---|---|---|---|---|---|---|
| kalata B1 | 2892.85 | 2890.39 | 1 | ICP | 2892.33 | 0.52 |
| kalata B2 | 2956.14 | 2953.74 | 1 | ICS | 2955.38 | 0.76 |
| kalata B3 | 3083.31 | 3080.64 | 1 | ICS | 3082.48 | 0.83 |
| kalata B4 | 2893.24 | 2890.56 | 1 | IS | 2893.31 | 0.07 |
| kalata B5 | — | — | — | P | 3061.59 | — |
| kalata B6 | 3029.96 | 3027.66 | 0.9999 | IS | 3029.42 | 0.54 |
| kalata B7 | 3072.26 | 3069.74 | 0.9998 | IS | 3071.59 | 0.67 |
| kalata B8 | 3284.34 | 3281.75 | 1 | ICS | 3283.79 | 0.55 |
| kalata B9 | — | — | — | P | 3272.72 | — |
| kalata B9 lin | — | — | — | P | 3290.74 | — |
| kalata B10 | 3030.21 | 3027.53 | 1 | ICS | 3030.41 | 0.20 |
| kalata B10 lin | 3048.54 | 3046.50 | 1 | ICS | 3048.43 | 0.11 |
| kalata B11 | 2884.48 | 2881.44 | 0.9999 | I | 2884.26 | 0.22 |
| kalata B12 | — | — | — | P | 2880.27 | — |
| kalata B13 | 3036.06 | 3033.58 | 1 | IC | 3036.46 | 0.40 |
| kalata B14 | 3023.74 | 3021.17 | 0.9987 | I | 3022.43 | 1.31 |
| kalata B15 | 2977.00 | 2974.56 | 1 | ICS | 2976.40 | 0.60 |
| kalata B18 | 3147.33 | 3145.02 | 0.9977 | I | 3145.67 | 1.66 |
| kalata S | 2878.81 | 2875.93 | 0.9993 | I | 2878.30 | 0.51 |
| Oak6 cyclotide 1 | 3035.87 | 3033.49 | 1 | IC | 3035.47 | 0.40 |
| [G-A] kalata B1[7] | 2906.47 | 2904.75 | 0.9995 | I | 2906.35 | 0.12 |
| kalata b1-1 | 2724.12 | 2722.28 | 1 | IC | 2724.18 | 0.06 |
| [L2A] kalata B1 | 2851.88 | 2849.54 | 1 | IC | 2850.25 | 1.63 |
| Ac-[desGly]-KB1-Am | 2854.31 | 2851.68 | 0.9996 | I | 2853.30 | 1.01 |
| acyclic kalata B1 | 2911.32 | 2908.36 | 1 | IC | 2910.35 | 0.97 |
| Oak6 cyclotide 2 | 3093.29 | 3090.61 | 1 | IC | 3092.56 | 0.73 |

[1]Identification by LC-MS reconstruct of at least 3 representative LC-MS experiments (±1 Da, 20-70 min, EMS 1000 2 scans) or identification by digest (trypsin or endo-GluC), nano LC-MS/MS and database search (ERA);
[2]Observed molecular weight;
[3]Score indicating the quality of LC-MS reconstructed peptide MW (≤1.0);
[4]Evidence for identified cyclotides, I = isotope pattern, C = charge pattern, S = full sequence, P = partial sequence or sequence tag;
[5]Data taken from CyBase (Wang, 2008, Nucleic Acids Res, 36, D206-210);
[6]Δ MW determined to average molecular weight;
[7]amino acid position (G-A replacement) not specified

TABLE 3

Comparison of kalata B1 (and other cyclotides) inhibitory effects IC50 values in various cellular test systems.

| Assay system | Cells | IC$_{50}$ (µM) | Reference |
|---|---|---|---|
| kalata B1 | | | |
| Anti-proliferative activity | human peripheral blood mononuclear cells | 3.9 ± 0.5 | Gründemann et al., 2012 |
| Nematocidal activity | *H. contortus* nematodes | 2.7 | Huang et al., 2010 |
| | *T. colibriformus* nematodes | 4.5 | Huang et al., 2010 |
| Cytotoxicity | human T-lymphoblast cells | 3.5 | Daly et al., 2004 |
| other cyclotides* | | | |
| Cytotoxicity | human lymphoma cell line (U-937) | 0.6-6 | Svangard et al., 2004 |
| | | 0.3-7 | Lindholm et al., 2002 |
| Cytotoxicity | human myeloma cell line (RPMI-8226/s) | 1-4 | Svangard et al., 2004 |
| | | 0.1-6 | Lindholm et al., 2002 |

*Activity was reported of various cyclotides (varv A, varv E, varv F, vitri A, cycloviolacin O2) from *Viola arvensis, V. odorata* and *V. tricolor*

TABLE 4

LC-MS reconstruct of *O. affinis* cyclotides. Raw (labelled) data of LC-MS reconstruct of *O. affinis* extracts as analysed by nano LC-MS.

| No. | cyclotide | Mass Da (avg.) | Da (mono.) | Score | Evidence | Theoretical Mass Da (avg.) | Δ Mass Da |
|---|---|---|---|---|---|---|---|
| 1 | new | 2706.63 | 2704.37 | 0.9997 | I | | |
| 2 | new | 2723.22 | 2721.27 | 1 | I | | |
| 3 | kalata b1-1 | 2724.12 | 2722.28 | 1 | IC | 2724.18 | 0.0559 |
| 4 | new | 2821.78 | 2819.36 | 1 | IC | | |
| 5 | new | 2822.30 | 2820.55 | 0.9995 | I | | |
| 6 | new | 2833.30 | 2831.41 | 1 | I | | |
| 7 | [L2A] kalata B1 | 2851.88 | 2849.54 | 1 | IC | 2850.25 | 1.6322 |
| 8 | Ac-[desGly]-KB1-Am | 2854.31 | 2851.68 | 0.9996 | I | 2853.3 | 1.0072 |
| 9 | new | 2873.73 | 2871.13 | 0.9996 | I | | |
| 10 | kalata S | 2878.81 | 2875.93 | 0.9993 | I | 2878.30 | 0.5141 |
| 11 | new | 2879.82 | 2877.46 | 1 | IC | | |
| 12 | kalata B12** | 2882.30 | 2880.83 | 0.9969 | I | 2880.27 | 2.0256 |
| 13 | kalata B11 | 2884.48 | 2881.44 | 0.9999 | I | 2884.26 | 0.2236 |
| 14 | new | 2891.45 | 2888.50 | 1 | IC | | |
| 15 | kalata B1 | 2892.85 | 2890.39 | 1 | IC | 2892.33 | 0.5228 |
| 16 | kalata B4 | 2893.24 | 2890.56 | 1 | I | 2893.31 | 0.0718 |
| 17 | new* | 2896.70 | 2894.45 | 0.9999 | I | | |
| 18 | new | 2897.11 | 2894.57 | 1 | IC | | |
| 19 | [G-A] kalata B1 | 2906.47 | 2904.75 | 0.9995 | I | 2906.35 | 0.1191 |
| 20 | new | 2909.53 | 2906.90 | 1 | IC | | |
| 21 | acyclic kalata B1 | 2911.32 | 2908.36 | 1 | IC | 2910.35 | 0.9675 |
| 22 | new* | 2912.90 | 2911.43 | 0.9999 | I | | |
| 23 | new* | 2922.95 | 2920.48 | 1 | IC | | |
| 24 | new* | 2925.32 | 2922.40 | 1 | IC | | |
| 25 | new* | 2926.80 | 2923.70 | 1 | IC | | |
| 26 | new | 2927.30 | 2924.66 | 1 | IC | | |
| 27 | new | 2937.91 | 2935.50 | 0.9998 | I | | |
| 28 | new | 2942.99 | 2940.48 | 1 | IC | | |
| 29 | kalata B2 | 2956.14 | 2953.74 | 1 | IC | 2955.38 | 0.7637 |
| 30 | new* | 2959.95 | 2957.56 | 1 | IC | | |
| 31 | new | 2960.36 | 2958.24 | 0.9996 | I | | |
| 32 | new | 2969.25 | 2968.13 | 0.9997 | I | | |
| 33 | new* | 2971.44 | 2969.50 | 1 | IC | | |
| 34 | new | 2973.80 | 2970.55 | 1 | IC | | |
| 35 | new | 2974.14 | 2971.51 | 1 | IC | | |
| 36 | new* | 2975.38 | 2973.49 | 1 | IC | | |
| 37 | kalata B15 | 2977.00 | 2974.56 | 1 | IC | 2976.40 | 0.602 |
| 38 | new* | 2986.57 | 2983.80 | 1 | I | | |
| 39 | new | 2988.28 | 2985.60 | 1 | IC | | |
| 40 | new | 2990.37 | 2987.51 | 1 | IC | | |
| 41 | new | 2994.11 | 2991.86 | 1 | IC | | |
| 42 | new* | 3006.25 | 3003.50 | 1 | IC | | |
| 43 | new* | 3010.97 | 3008.88 | 1 | IC | | |
| 44 | kalata B14 | 3023.74 | 3021.17 | 0.9987 | I | 3022.43 | 1.3147 |
| 45 | new* | 3028.61 | 3025.92 | 0.9998 | I | | |
| 46 | kalata B6 | 3029.96 | 3027.66 | 0.9999 | I | 3029.42 | 0.5381 |
| 47 | kalata B10 | 3030.21 | 3027.53 | 1 | IC | 3030.41 | 0.2028 |
| 48 | Oak6 cyclotide 1 | 3035.87 | 3033.49 | 1 | IC | 3035.47 | 0.398 |
| 49 | kalata B13 | 3036.06 | 3033.58 | 1 | IC | 3036.46 | 0.4018 |
| 50 | new | 3039.91 | 3037.45 | 1 | IC | | |
| 51 | new | 3040.05 | 3036.62 | 1 | IC | | |
| 52 | new* | 3045.78 | 3043.50 | 1 | IC | | |
| 53 | new* | 3046.32 | 3044.95 | 1 | IC | | |
| 54 | new | 3047.97 | 3046.60 | 0.9999 | I | | |
| 55 | kalata B10 lin | 3048.54 | 3046.50 | 1 | IC | 3048.43 | 0.1091 |
| 56 | new* | 3051.82 | 3048.48 | 1 | IC | | |
| 57 | new* | 3052.72 | 3049.57 | 1 | IC | | |
| 58 | new* | 3065.79 | 3063.36 | 0.9997 | I | | |
| 59 | kalata B7 | 3072.26 | 3069.74 | 0.9998 | I | 3071.59 | 0.67 |
| 60 | new* | 3073.89 | 3072.70 | 0.9999 | I | | |
| 61 | kalata B3 | 3083.31 | 3080.64 | 1 | IC | 3082.48 | 0.8309 |
| 62 | new* | 3087.22 | 3084.61 | 1 | IC | | |
| 63 | new | 3089.27 | 3086.96 | 0.9997 | I | | |
| 64 | new | 3091.00 | 3089.03 | 0.9997 | I | | |
| 65 | Oak6 cyclotide 2 | 3093.29 | 3090.61 | 1 | IC | 3092.56 | 0.7328 |
| 66 | new* | 3097.63 | 3094.57 | 1 | IC | | |
| 67 | new* | 3099.85 | 3096.60 | 1 | IC | | |
| 68 | kalata B18** | 3147.33 | 3145.02 | 0.9977 | I | 3145.67 | 1.6615 |
| 69 | new* | 3266.81 | 3264.99 | 0.9997 | I | | |
| 70 | kalata B8 | 3284.34 | 3281.75 | 1 | IC | 3283.79 | 0.5453 |

TABLE 4-continued

LC-MS reconstruct of *O. affinis* cyclotides. Raw (labelled) data of LC-MS reconstruct of *O. affinis* extracts as analysed by nano LC-MS.

| No. | cyclotide | Mass Da (avg.) | Da (mono.) | Score | Evidence | Theoretical Mass Da (avg.) | Δ Mass Da |
|---|---|---|---|---|---|---|---|
| 71 | new* | 3300.96 | | 1 | C | | |
| 72 | new | 3446.88 | 3444.98 | 0.9998 | I | | |
| Total: | 72 | | | | | | |
| New: | 25 | | | | | | |
| New*: | 24 | | | | | | |

LC-MS reconstruct, EMS 1000 Da/sec
Reconstruct 2700-3500 Da, signal-to-noise: 4, 25, 50; combined datasets from at least 3 independent LC-MS runs
CyBase comparison: MW +/− 1 Da
* = other cylotide detected (not Oaffinis)
** = +/− Da

TABLE 5

*O. affinis* database search results following digests and LC-MS/MS analysis. Protein Pilot™ database search results of the cyclotide LC-MS/MS analysis.

| N | Unused | Total | % Cov | % Cov(50) | % Cov(95) | Accession | Name | Peptides(95%) |
|---|---|---|---|---|---|---|---|---|
| | | | | trypsin digest | | | | |
| 1 | 6.43 | 6.43 | 100.00 | 85.48 | 82.26 | cb\|P85175 | kalata B8/1-31\|cybaseid = 168 organism = Oldenlandia affinis | 4 |
| 2 | 6.00 | 6.00 | 100.00 | 51.72 | 51.72 | cb\|P58457 | kalata B7/1-29\|cybaseid = 26 organism = Oldenlandia affinis | 6 |
| 3 | 5.91 | 5.91 | 100.00 | 98.28 | 96.55 | cb\|P58454 | kalata 62/1-29\|cybaseid = 4 organism = Oldenlandia affinis | 4 |
| 4 | 2.75 | 2.75 | 100.00 | 98.28 | 72.41 | cb\|P83938 | kalata B4\|1-29\|cybaseid = 30 organism = Oldenlandia affinis | 2 |
| 5 | 2.63 | 2.63 | 93.33 | 88.33 | 88.33 | cb\|P58456 | kalata B5/1-30\|cybaseid = 59 organism = Oldenlandia affinis | 5 |
| 6 | 2.00 | 3.75 | 100.00 | 98.28 | 72.41 | cb\|P85133 | kalata B15/1-29\|cybaseid = 253 organism = Oldenlandia affinis | 3 |
| 7 | 2.00 | 2.00 | 100.00 | 50.00 | 50.00 | cb\|P85128 | kalata B10/1-30\|cybaseid = 246 organism = Oldenlandia affinis | 1 |
| 7 | 0.00 | 2.00 | 100.00 | 50.00 | 50.00 | cb\|P247 | kalata B10 linear/1-30cybaseid = 247 organism = Oldenlandia affinis | 1 |
| 8 | 2.00 | 2.00 | 85.48 | 85.48 | 43.55 | cb\|P85127 | kalata B9/1-31\|cybaseid = 244 organism = Oldenlandia affinis | 1 |
| 8 | 0.00 | 2.00 | 85.48 | 85.48 | 43.55 | cb\|P245 | kalata 69 linear/1-31\|cybaseid = 245 organism = Oldenlandia affinis | 1 |
| 9 | 2.00 | 2.00 | 98.21 | 50.00 | 50.00 | cb\|P85130 | kalata B12/1-28\|cybaseid = 250 organism = Oldenlandia affinis | 2 |
| 10 | 1.06 | 2.00 | 100.00 | 50.00 | 50.00 | cb\|P58455-b3 | kalata B6/1-30\|cybaseid = 24 organism = Oldenlandia affinis | 1 |
| 10 | 0.00 | 2.00 | 100.00 | 50.00 | 50.00 | cb\|P247 | kalata B10 linear/1-30cybaseid = 247 organism = Oldenlandia affinis | 1 |
| 11 | 0.63 | 2.01 | 98.28 | 98.28 | 72.41 | cb\|P56254 | kalata B1/1-29\|cybaseid = 1 organism = Viola odorata; Oldenlandia affinis; Viola baoshanensis; Viola yedoensis | 4 |
| 12 | 0.20 | 0.20 | 100.00 | 61.67 | 0.00 | cb\|P58455-b6 | kalata B3/1-30\|cybaseid = 25 organism = Oldenlandia affinis | 0 |
| | | | | Endo GluC digest | | | | |
| 1 | 0.88 | 0.88 | 100 | 87.92999983 | 0 | cb\|P58454 | kalata B2/1-29\|cybaseid = 4 organism = Oldenlandia affinis | 0 |
| 2 | 0.52 | 0.52 | 100 | 50 | 50 | cb\|P58457 | kalata B7/1-29\|cybaseid = 26 organism = Oldenlandia affinis | 1 |
| 3 | 0.21 | 0.21 | 100 | 25 | 0 | cb\|P58455-b6 | kalata B3/1-30\|cybaseid = 25 organism = Oldenlandia affinis | 0 |

TABLE 6

Cyclotide quantification data. Data of five independent experiments of cyclotide quantification.

| Identified cyclotide | MW calculated (Da) | SEM | Δ MW (Da) | MW LC-MS reconstruct (Da) | SEM | Δ MW (Da) | MW theoretical (Da) | RT (min) | SEM | Area (mAU*min) | SEM | Height (mAU) | SEM | Rel.Area % | SEM |
|---|---|---|---|---|---|---|---|---|---|---|---|---|---|---|---|
| kalata B8 | 3283.91 | 0.15 | 0.12 | 328424 | 0.19 | 0.45 | 3283.79 | 29.95 | 0.01 | 20.55 | 0.57 | 28.01 | 0.72 | 5.6 | 0.2 |
| kalata B7 | 3071.83 | 0.19 | 0.24 | 3072.27 | 0.17 | 0.66 | 3071.59 | 37.54 | 0.04 | 7.89 | 0.22 | 41.43 | 0.21 | 2.2 | 0.1 |
| kalata B1 | 2892.27 | 0.27 | 0.06 | 2892.98 | 0.21 | 0.65 | 2892.33 | 45.48 | 0.02 | 50.81 | 0.84 | 96.96 | 0.61 | 13.9 | 0.2 |
| kalata B6 | 3029.60 | 0.28 | 0.18 | 3029.84 | 0.12 | 0.42 | 3029.42 | 46.50 | 0.03 | 29.63 | 0.46 | 46.88 | 0.38 | 0.1 | 0.1 |
| kalata B13 | 3035.56 | 0.20 | 0.90 | 303589 | 0.12 | 0.57 | 3036.46 | 50.32 | 0.03 | 14.88 | 1.16 | 28.75 | 0.38 | 4.1 | 0.3 |
| kalata B2 | 2955.76 | 0.12 | 0.38 | 2955.90 | 0.09 | 0.52 | 2955.38 | 51.82 | 0 03 | 72.86 | 3.17 | 103.65 | 0.86 | 20.0 | 0.6 |
| kalata B3 | 3082.72 | 0.21 | 0.24 | 3083.04 | 0.08 | 0.55 | 3082.48 | 52.59 | 0.07 | 11.00 | 1.40 | 23.02 | 1.27 | 3.0 | 0.4 |

*n = 5, HPLC quantification (area under curve) of five independent experiments
**MW average mass
***MW calculated from +2 or +3 ion The present invention refers to the following nucleotide and amino acid sequences:

SEQ ID No. 1:
Amino acid sequence of Kalata B1:
GLPVCGETCVGGTCNTPGCTCSWPVCTRN

SEQ ID No. 2:
Amino acid sequence of Kalata B2:
GLPVCGETCFGGTCNTPGCSCTWPICTRD

SEQ ID No. 3:
Amino acid sequence of D-Kalata B2: all-D
GLPVCGETCFGGTCNTPGCSCTWPICTRD SEQ ID No. 4:
Amino acid sequence of Kalata G18K:
GLPVCGETCVGGTCNTPKCTCSWPVCTRN SEQ ID No. 5:
Amino acid sequence of Kalata N29K:
GLPVCGETCVGGTCNTPGCTCSWPVCTRK SEQ ID No. 6:
Amino acid sequence of Kalata T20K, G1K:
KLPVCGETCVGGTCNTPGCKCSWPVCTRN SEQ ID No. 7:
Amino acid sequence of Kalata T20K:
GLPVCGETCVGGTCNTPGCKCSWPVCTRN SEQ ID No. 8:
Amino acid sequence of Kalata T8K:
GLPVCGEKCVGGTCNTPGCTCSWPVCTRN SEQ ID No. 9:
Amino acid sequence of Kalata V10A:
GLPVCGETCAGGTCNTPGCTCSWPVCTRN SEQ ID No. 10:
Amino acid sequence of Kalata V10K:
GLPVCGETCKGGTCNTPGCTCSWPVCTRN SEQ ID No. 11:
Nucleotide sequence encoding Kalata B1:
GGACTTCCAGTATGCGGTGAGACTTGTGTTGGGGGAACTTGCAACACTCC

AGGCTGCACTTGCTCCTGGCCTGTTTGCACACGCAAT

SEQ ID No. 12:
Nucleotide sequence encoding Kalata B2:
GGTCTTCCAGTATGCGGCGAGACTTGCTTTGGGGGAACTTGCAACACTCC

AGGCTGCTCTTGCACCTGGCCTATCTGCACACGCGAT

SEQ ID No. 13:
Amino acid sequence of the Kalata B1 precursor protein. The mature Kalata B1 domain is underlined. P56254, Kalata-B1, *Oldenlandia affinis*
MAKFTVCLLLCLLLAAFVGAFGSELSDSHKTTLVNEIAEKMLQRKILDGV

EATLVTDVAEKMFLRKMKAEAKT SETADQVFLKQLQLKGLPVCGETCVG

GTCNTPGCTCSWPVCTRNGLPSLAA

SEQ ID No. 14:
Amino acid sequence of the Kalata B2 precursor protein. The three mature Kalata B2 domains are underlined. P58454, Kalata-B2, *Oldenlandia affinis*
MAKFTNCLVLSLLLAAFVGAFGAEFSEADKATLVNDIAENIQKEILGEVK

TSETVTLTMELKEMQLKGLPVCGETCFGGTCNTPGCSCTWPICTRDSLPMR

AGGKTSETTLHMFLKEMQLKGLPVCGETCFGGTCNTPGCSCTWPICTRDS

LPMSAGGKTSETTLHMELKEMQLKGLPVCGETCFGGTCNTPGCSCTWPIC

TRDSLPLVAA

SEQ ID No. 15:
Nucleotide sequence encoding the Kalata B1 precursor protein. The nucleotide sequence corresponding to the mature Kalata B1 domain is underlined.
>gi|15667740|gb|AF393825.1|*Oldenlandia affinis* kalata B1 precursor, mRNA, complete cds
GGCACCAGCACTTTCTTAAAATTTACTGCTTTTTCTTATTTCTTGTTCTG

TGCTTGCTTCTTCCATGGCTAAGTTCACCGTCTGTCTCCTCCTGTGCTTG

CTTCTTGCAGCATTTGTTGGGCCGTTTGGATCTGAGCTTTCTGACTCCCA

CAAGACGACCTTGGTCAATGAAATCGCTGAGAAGATGCTACAAAGAAAGA

TATTGGATGGAGTGGAAGCTACTTTGGTCACTGATGTCCCCGAGAAGATG

TTCCTAAGAAAGATGAAGGCTGAAGCGAAAACTTCTGAAACCGCCGATCA

GGTGTTCCTGAAACAGTTGCAGCTCAAA<u>GGACTTCCACTATGCGGTGAGA</u>

<u>CTTGTGTTGGCGCAACTTGCAACACTCCAGGCTCCACTTGCTCCTGGCCT</u>

<u>GTTTGCACACGCAAT</u>GGCCTTCCTAGTTTGGCCGCATAATTTGCTTGATC

AAACTGCAAAAATGAATGAGAAGGCCGACACCAATAAAGCTATCAATGTA

GTTGGTCCCTGTACTTAATTTGGTTGGCTCCAAACCATGTGTGCTGCTCT

TGTTTTTGTTTTTTCTTTTTTCTTCTCTCTTTCGGGCACTCTTCAGGACA

TGAAGTGATGATCAGTACTCTTTGCTATCATGTTTTCTGTGCACACCTTC

TATTGTAGGTGTTGTTGTGATGTTGATGCCCAATTGGATAACTGTTGTCG

TTGTTAAAAAAAAAAAAAA

SEQ ID No. 16:
Nucleotide sequence of encoding the Kalata B2 precursor protein. The nucleotide sequences corresponding to the three mature Kalata B2 domais are underlined.
>gi|15667746|gb|AF393828.1|*Oldenlandia affinis* kalata 82 precursor, mRNA, complete cds
GGCACCAGATACAACCCCTTTCTTATAATTTATTGCTTTTCTTATTCCTT

GAAAAAGGAGAAATAATATTGGATCTTCCATGGCTAAGTTCACCAACTGT

CTCGTCCTGAGCTTGCTTCTAGCAGCATTTGTTGGGGCTTTCGGAGCTGA

GTTTTCTGAAGCCGACAAGGCCACCTTGGTCAATGATATCGCTGAGAATA

TCCAAAAAGAGATACTGGGCGAAGTGAAGACTTCTGAAACCGTCCTTACG

ATGTTCCTGAAAGAGATGCAGCTCAAA<u>GGTCTTCCAGTATGCGGCGAGAC</u>

<u>TTGCTTTGGGGGAACTTGCAACACTCCAGGCTGCTCTTGCACCTGGCCTA</u>

<u>TCTGCACACGCGAT</u>AGCCTTCCTATGAGGGCTGGAGGAAAAACATCTGAA

ACCACCCTTCATATGTTCCTGAAAGAGATGCAGCTCAAG<u>GGTCTTCCAGT</u>

<u>TTGCCGCGAGACTTGCTTTGGGGGAACTTGCAACACTCCAGGCTGCTCGT</u>

<u>GCACCTGGCCTATCTGCACACGCGAT</u>AGCCTTCCTATGAGTGCTGGAGGA

AAAACATCTGAAACCACCCTTCATATGTTCCTGAAAGAGATGCAGCTCAA

<u>GGGTCTTCCAGTTTGCGGCGAGACTTGCTTTGGGGGAACTTGCAACACTC</u>

<u>CAGGCTGCTCGTGCACCTGGCCTATATGCACACGTGAT</u>AGCCTTCCTCTT

GTGGCTGCATAATTTGCTTCATCAAACTGCAAATGAATAAGAAGGGACA

CTAAATTAGCTATGAATTTTGTTGGCCCTTGTGTCTGGTAATTTGGTTCC

CGCCAAATTAACCATATGTATGCATTGCTCCTTTTTTCTTTCTTTTTTT

CCCCCTCATTTGGGCACTCTTCATTACATGAAGAGATCATGACGCTTTGT

```
TACTCTGAGCACCCCCTGTTGGTGTTGTTCACATGTTGATGCCCATGTTG

GAATAAACTCTTGTTTTTGTTACCAAAAAAAAAAAAAAAAA

SEQ ID No. 17:
Consensus amino acid sequence of active Cyclotides
(Xxx₁ is any amino acid, non-natural amino acid
or peptidomimetic; Xxx₂ is any amino acid, non-
natural amino acid or peptidomimetic but not Lys;
and Xxx₃ is any amino acid, non-natural
amino acid or peptidomimetic but not Ala or Lys):
Xxx₁-Leu-Pro-Val-Cys-Gly-Glu-Xxx₂-Cys-Xxx₃-Gly- Gly-Thr-Cys-Asn-Thr-Pro-Xxx₁-Cys-Xxx₁-Cys-Xxx₁-

Trp-Pro-Xxx₁-Cys-Thr-Arg-Xxx₁
```

FURTHER REFERENCES

1. Ewing *Immunol Cell Biol* 76, 47-54 (1998).
2. Bernard *Curr Opin Immunol* 4, 760-765 (1992).
3. Onuki *Microsc Res Tech* 52, 731-739 (2001).
4. Ayers *Neurochem Int* 45, 409-419 (2004).
5. Bernard *J Mol Med* 75, 77-88 (1997).
6. Dubois *J Neurol Neurosurg Psychiatry* 74, 946-949 (2003).
7. Krause *Febs J* 274, 86-95 (2007).
8. Reiss *Platelets* 17, 153-157 (2006).
9. Zhou *J Virol* 81, 7517-7528 (2007).
10. dos Santos *J Neuroimmunol* 162, 122-129 (2005).
11. Martin *Nat Biotechnol* 21, 71-76 (2003).
12. Craik *J Mol Biol* 294, 1327-1336 (1999).
13. Craik *Science* 311, 1563-1564 (2006).
14. Craik *Biopolymers* 84, 250-266 (2006).
15. Rosengren *J Biol Chem* 278, 8606-8616 (2003).
16. Simonsen, *J Biol Chem* 283, 9805-9813 (2008).
17. Cemazar *Internat. J. of Peptide Research and Therapeutics* 12, 253-260 (2006).
18. Colgrave *Biochemistry* 43, 5965-5975 (2004).
19. Okuda *J Interferon Cytokine Res* 18, 415-421 (1998).
20. Schnolzer *Int J Pept Protein Res* 40, 180-193 (1992).
21. Dawson *Science* 266, 776-779 (1994).
22. Albouz-Abo *Eur J Biochem* 246, 59-70 (1997).
23. Hvas *Scand J Immunol* 46, 195-203 (1997).
24. Johns *Mol Immunol* 34, 33-38 (1997).
25. Menon *J Neurochem* 69, 214-222 (1997).
26. Liu *Nat Med* 4, 78-83 (1998).
27. Slavin *Autoimmunity* 28, 109-120 (1998).
28. Ichikawa *Int Immunol* 8, 1667-1674 (1996).
29. Ichikawa *J Immunol* 157, 919-926 (1996).
30. Bernard *Clin Exp Immunol* 52, 98-106 (1983).
31. Pedersen *J Neuroimmunol* 5, 251-259 (1983).
32. Bettadapura *J Neurochem* 70, 1593-1599 (1998).
33. Okuda *J Neuroimmunol* 131, 115-125 (2002).
34. Ichikawa *Cell Immunol* 191, 97-104 (1999).
35. Daly *Biochemistry* 38, 10606-10614 (1999).
36. Cemazar *J Biol Chem* 281, 8224-8232 (2006).
37. Owens *Curr Opin Neurol* 16, 259-265 (2003).
38. Nicholson *Curr Opin Immunol* 8, 837-842 (1996).
39. Gonzalo *J Immunol* 166, 1-5 (2001).
40. Henry *Immunol Today* 20, 285-288 (1999).
41. Ihle *Nature* 377, 591-594 (1995).
42. Janeway *Cell* 76, 275-285 (1994).
42. Minami *Annu. Rev. Immunol* 11, 245-268 (1993).
43. Svanborg *Curr Opin Microbiol* 2, 99-105 (1999).
44. DeVries *Semin Immunol* 11, 95-104 (1999).
45. Larsson *Inflammation* 23, 217-230 (1999).
46. Cerdan *Res Immunol* 146, 164-168 (1995).
47. Jain *Curr Opin Immunol* 7, 333-342 (1995).
48. Romagnani *Inflamm Bowel Dis* 5, 285-294 (1999).
49. Orlinick *Cell Signal* 10, 543-551 (1998).
50. Romanic *Lab Invest* 76, 11-23 (1997).
51. Horn *Immunobiology* 202, 151-167 (2000).
52. Callan *J Clin Invest* 106, 1251-1261 (2000).
53. Gründemann *J Nat Prod* 75, 167-174 (2012).
54. Betts *J Immunol Methods* 281, 65-78 (2003).
55. Abraham *Curr Opin Immunol* 10, 330-336 (1998).
56. Ohta *J Immunol* 183, 5487-5493 (2009).

The invention claimed is:

1. Method of screening for and/or selecting an immunosuppressive cyclotide, the method comprising:
   (i) contacting activated immune cells with a cyclotide or a plant extract containing a cyclotide and determining the proliferative activity of said activated immune cells, wherein a reduced proliferative activity as compared to a control is indicative for the immunosuppressive activity of the cyclotide or plant extract containing a cyclotide; or
   (ii) administering to an animal model a pharmaceutically effective amount of a cyclotide or a plant extract containing a cyclotide and determining one or more parameters of the immune system, wherein the reduction of the one or more parameters of the immune system as compared to a control is indicative for the immunosuppressive activity of the cyclotide or plant extract containing a cyclotide.

2. The method of claim 1, comprising introducing a mutation into the cyclotide prior to:
   contacting the activated immune cells with the cyclotide or plant extract; or
   administering to the animal model a pharmaceutically effective amount of the cyclotide or plant extract.

3. The method of claim 2, wherein the mutated cyclotide demonstrates:
   a reduced proliferative activity in activated immune cells as compared to the non-mutated cyclotide; or
   a reduction of one or more parameters of the immune system in the animal model as compared to the non-mutated cyclotide.

4. The method of claim 1, further comprising isolating and/or identifying the immunosuppressive cyclotide from the plant extract.

5. The method of claim 1, wherein the cyclotide is or comprises a non-grafted cyclotide.

6. The method of claim 1 (i), wherein the control comprises:
   determining the proliferative activity of activated immune cells that have not been contacted with the cyclotide or the plant extract containing a cyclotide; or
   determining the proliferative activity of activated immune cells that have been contacted with a known cyclotide that does not have immunosuppressive activity.

7. The method of claim 1 (ii), wherein the control comprises:
   determining the one or more parameters of the immune system in the animal model that have not been administered the cyclotide or the plant extract containing a cyclotide; or
   determining the one or more parameters of the immune system in the animal model that have been administered a known cyclotide that does not have immunosuppressive activity.

8. The method of claim 1 (i), wherein activated immune cells comprise activated human peripheral blood mononuclear cells (PBMCs) or human T-lymphocyte.

9. The method of claim 8, wherein the activated human PBMCs comprises CD107a⁺ CD8⁺ PBMCs.

10. The method of claim 1 (ii), wherein the parameter of the immune system is selected from the group consisting of secretion/production of IL-2, secretion/production of IFN-gamma, secretion/production of TNF-alpha, degranulation/cytotoxicity of CD107a+ CD8+ PBMCs, and expression of IL-2 surface receptor CD25.

11. The method of claim 1 (ii), wherein the animal model comprises an animal model for an autoimmune disease.

12. The method of claim 11, wherein the animal model for an autoimmune disease comprises the Experimental Autoimmune Encephalitis (EAE) mouse model for Multiple Sclerosis (MS).

13. The method of claim 1, wherein the cyclotide comprises a head-to-tail cyclized peptide comprising six conserved cysteine residues capable of forming three disulphide bonds arranged in a cyclic cystine knot (CCK) motif.

14. The method of claim 1, wherein said cyclotide comprises a cyclic backbone having the structure of formula I, wherein formula I comprises the amino acid sequence:

$$\text{Cyclo}(C[X_1 \ldots Xa] \; C[XI1 \ldots XIb] \; C[XII1 \ldots XIIc] \; C[XIII1 \ldots XIIId] \; C[XIV1 \ldots XIVe] \; C[XV1 \ldots XVf]);$$

wherein C is cysteine;

wherein each of [X1 . . . Xa], [XI1 . . . XIb], [XII1 . . . XIIc], [XIII1 . . . XIIId], [XIV1 . . . XIVe], and [XV1 . . . XVf] represents one or more amino acid residues, wherein each one or more amino acid residues within or between the sequence residues may be the same or different; and wherein a, b, c, d, e, and f represent the number of amino acid residues in each respective sequence and each of a to f may be the same or different and range from 1 to about 20.

15. The method of claim 14, wherein a is 3 to 6, b is 4 to 8, c is 3 to 10, d is 1, e is 4 to 8, and/or f is 5 to 13.

16. The method of claim 1, wherein the cyclotide is or comprises a mutant or variant of kalta B.

17. The method of claim 1, wherein said cyclotide comprises an amino acid sequence of formula II; wherein formula II comprises:

(SEQ ID NO. 17)
$\text{Xxx}_1\text{-Leu-Pro-Val-Cys-Gly-Glu-Xxx}_2\text{-Cys-Xxx}_3\text{-Gly-}$ $\text{Gly-Thr-Cys-Asn-Thr-Pro-Xxx}_1\text{-Cys-Xxx}_1\text{-Cys-Xxx}_1\text{-}$ $\text{Trp-Pro-Xxx}_1\text{-Cys-Thr-Arg-Xxx}_1\text{,;}$ wherein $\text{Xxx}_1$ comprises any amino acid, non-natural amino acid or peptidomimetic;

wherein $\text{Xxx}_2$ comprises any amino acid, non-natural amino acid or peptidomimetic but not Lys; and wherein $\text{Xxx}_3$ comprises any amino acid, non-natural amino acid or peptidomimetic but not Ala or Lys.

18. The method of claim 1, wherein said cyclotide comprises an amino acid sequence that is at least 90% identical to any amino acid sequence of SEQ ID NOs: 1, 2, 3, 4, 5, 6, and 7.

19. The method of claim 1, wherein said cyclotide reduces secretion/production of IL-2, reduces secretion/production of IFN-gamma, reduces secretion/production of TNF-alpha, suppresses/reduces degranulation/cytotoxicity of CD107a+ CD8+ PBMCs, and/or suppresses/reduces expression of IL-2 surface receptor CD25.

20. The method of claim 1, wherein the anti-proliferative effect or suppression/reduction is mediated in an IL-2-, IFN-gamma- and/or TNF-alpha-depending manner and/or can be antagonized by IL-2.

\* \* \* \* \*

UNITED STATES PATENT AND TRADEMARK OFFICE
CERTIFICATE OF CORRECTION

PATENT NO.        : 10,357,537 B2
APPLICATION NO.   : 16/174428
DATED             : July 23, 2019
INVENTOR(S)       : Gruber et al.

It is certified that error appears in the above-identified patent and that said Letters Patent is hereby corrected as shown below:

On the Title Page

Item (71), Applicant: Medizinische Universitat Wien, should be "Wien (AT)" and not "Vienna (AT)"

Signed and Sealed this
Third Day of September, 2019

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 29
<212> TYPE: PRT
<213> ORGANISM: Oldenlandia affinis

<400> SEQUENCE: 1

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 2
<211> LENGTH: 29
<212> TYPE: PRT
<213> ORGANISM: Oldenlandia affinis

<400> SEQUENCE: 2

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp
            20                  25
```

```
<210> SEQ ID NO 3
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 3

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 4

Gly Leu Pro Val Cys Gly Glu Thr Cys Val Gly Gly Thr Cys Asn Thr
1               5                   10                  15

Pro Lys Cys Thr Cys Ser Trp Pro Val Cys Thr Arg Asn
            20                  25

<210> SEQ ID NO 5
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 5

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Lys
            20                  25

<210> SEQ ID NO 6
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 6

Lys Leu Pro Val Cys Gly Glu Thr Cys Val Gly Gly Thr Cys Asn Thr
1               5                   10                  15

Pro Gly Cys Lys Cys Ser Trp Pro Val Cys Thr Arg Asn
            20                  25

<210> SEQ ID NO 7
<211> LENGTH:

<210> SEQ ID NO 8
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 8

Gly Leu Pro Val Cys Gly Glu Lys Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 9
<211> LENGTH: 29
<212> TYPE: PRT
<213> ORGANISM: Artificial Sequence
<220> FEATURE:
<223> OTHER INFORMATION: Mutant form of Kalata B1

<400> SEQUENCE: 9

Gly Leu Pro Val Cys Gly Glu Thr Cys Ala Gly Gly Thr Cys Asn Thr
1               5                   10                  15

Pro Gly Cys Thr

<400> SEQUENCE: 13

```
Met Ala Lys Phe Thr Val Cys Leu Leu Cys Leu Leu Leu Ala Ala
1               5                   10                  15

Phe Val Gly Ala Phe Gly Ser Glu Leu Ser Asp Ser His Lys Thr Thr
                20                  25                  30

Leu Val Asn Glu Ile Ala Glu Lys Met Leu Gln Arg Lys Ile Leu Asp
            35                  40                  45

Gly Val Glu Ala Thr Leu Val Thr Asp Val Ala Glu Lys Met Phe Leu
    50                  55                  60

Arg Lys Met Lys Ala Glu Ala Lys Thr Ser Glu Thr Ala Asp Gln Val
65                  70                  75                  80

Phe Leu Lys Gln Leu Gln Leu Lys Gly Leu Pro Val Cys Gly Glu Thr
                85                  90                  95

Cys Val Gly Gly Thr Cys Asn Thr Pro Gly Cys Thr Cys Ser Trp Pro
            100                 105                 110

Val Cys Thr Arg Asn Gly Leu Pro Ser Leu Ala Ala
        115                 120
```

<210> SEQ ID NO 14
<211> LENGTH: 210
<212> TYPE: PRT
<213> ORGANISM: Oldenlandia affinis

<400> SEQUENCE: 14

```
Met Ala Lys Phe Thr Asn Cys Leu Val Leu Ser Leu Leu Leu Ala Ala
1               5                   10                  15

Phe Val Gly Ala Phe Gly Ala Glu Phe Ser Glu Ala Asp Lys Ala Thr
                20                  25                  30

Leu Val Asn Asp Ile Ala Glu Asn Ile Gln Lys Glu Ile Leu Gly Glu
            35                  40                  45

Val Lys Thr Ser Glu Thr Val Leu Thr Met Phe Leu Lys Glu Met Gln
    50                  55                  60

Leu Lys Gly Leu Pro Val Cys Gly Glu Thr Cys Phe Gly Gly Thr Cys
65                  70                  75                  80

Asn Thr Pro Gly Cys Ser Cys Thr Trp Pro Ile Cys Thr Arg Asp Ser
                85                  90                  95

Leu Pro Met Arg Ala Gly Gly Lys Thr Ser Glu Thr Thr Leu His Met
            100                 105                 110

Phe Leu Lys Glu Met Gln Leu Lys Gly Leu Pro Val Cys Gly Glu Thr
        115                 120                 125

Cys Phe Gly Gly Thr Cys Asn Thr Pro Gly Cys Ser Cys Thr Trp Pro
    130                 135                 140

Ile Cys Thr Arg Asp Ser Leu Pro Met Ser Ala Gly Gly Lys Thr Ser
145                 150                 155                 160

Glu Thr Thr Leu His Met Phe Leu Lys Glu Met Gln Leu Lys Gly Leu
                165                 170                 175

Pro Val Cys Gly Glu Thr Cys Phe Gly Gly Thr Cys Asn Thr Pro Gly
            180                 185                 190

Cys Ser Cys Thr Trp Pro Ile Cys Thr Arg Asp Ser Leu Pro Leu Val
        195                 200                 205

Ala Ala
    210
```

<210> SEQ ID NO 15
<211> LENGTH: 724

<212> TYPE: DNA
<213> ORGANISM: Oldenlandia affinis

<400> SEQUENCE: 15

```
ggcaccagca ctttcttaaa atttactgct ttttcttatt tcttgttctg tgcttgcttc    60
ttccatggct aagttcaccg tctgtctcct cctgtgcttg cttcttgcag catttgttgg   120
ggcgtttgga tctgagcttt ctgactccca caagaccacc ttggtcaatg aaatcgctga   180
gaagatgcta caaagaaaga tattggatgg agtggaagct actttggtca ctgatgtcgc   240
cgagaagatg ttcctaagaa agatgaaggc tgaagcgaaa acttctgaaa ccgccgatca   300
ggtgttcctg aaacagttgc agctcaaagg acttccagta tgcggtgaga cttgtgttgg   360
gggaacttgc aacactccag ctgcacttg ctcctggcct gtttgcacac gcaatggcct   420
tcctagtttg gccgcataat ttgcttgatc aaactgcaaa aatgaatgag aaggccgaca   480
ccaataaagc tatcaatgta gttggtccct gtacttaatt tggttggctc caaaccatgt   540
gtgctgctct tgttttgtt ttttcttttt tcttctctct ttcgggcact cttcaggaca   600
tgaagtgatg atcagtactc tttgctatca tgttttctgt gcacaccttc tattgtaggt   660
gttgttgtga tgttgatgcc caattggaat aaactgttgt cgttgttaaa aaaaaaaaa   720
aaaa                                                               724
```

<210> SEQ ID NO 16
<211> LENGTH: 993
<212> TYPE: DNA
<213> ORGANISM: Oldenlandia affinis

<400> SEQUENCE: 16

```
ggcaccagat acaaccccctt tcttataatt tattgctttt cttattcctt gaaaaaggag    60
aaataatatt ggatcttcca tggctaagtt caccaactgt ctcgtcctga gcttgcttct   120
agcagcattt gttggggctt tcggagctga gttttctgaa gccgacaagg ccaccttggt   180
caatgatatc gctgagaata ccaaaaaga gatactgggc gaagtgaaga cttctgaaac   240
cgtccttacg atgttcctga aagagatgca gctcaaaggt cttccagtat gcggcgagac   300
ttgctttggg ggaacttgca acactccagg ctgctcttgc acctggccta tctgcacacg   360
cgatagcctt cctatgaggg ctggaggaaa acatctgaa ccaccccttc atatgttcct   420
gaaagagatg cagctcaagg gtcttccagt ttgcggcgag acttgctttg ggggaacttg   480
caacactcca ggctgctcgt gcacctggcc tatctgcaca cgcgatagcc ttcctatgag   540
tgctggagga aaacatctg aaaccaccct tcatatgttc ctgaaagaga tgcagctcaa   600
gggtcttcca gtttgcggcg agacttgctt tgggggaact tgcaacactc caggctgctc   660
gtgcacctgg cctatatgca cacgtgatag ccttcctctt gtggctgcat aatttgcttc   720
atcaaactgc aaaatgaata agaagggaca ctaaattagc tatgaatttt gttggcccttt   780
gtgtctggta atttggttcc cgccaaatta accatatgta tgcattgctc ctttttttct   840
tcttttttttt cccctcatt tgggcactct tcattacatg aagagatcat gacgctttgt   900
tactctgagc accccctgtt ggtgttgttc acatgttgat gcccatgttg aataaactc   960
ttgttttttgt taccaaaaaa aaaaaaaaaa aaa                              993
```

<210> SEQ ID NO 17
<211> LENGTH: 29
<212> TYPE: PRT
<213> ORGANISM: Artificial Sequence
<220> FEATURE:

```
<223> OTHER INFORMATION: Mutant form of Kalata B1
<220> FEATURE:
<221> NAME/KEY: variant
<222> LOCATION: (1)..(1)
<223> OTHER INFORMATION: Xaa can be any amino acid
<220> FEATURE:
<221> NAME/KEY: variant
<222> LOCATION: (8)..(8)
<223> OTHER INFORMATION: Xaa can be Ala, Cys, Asp, Glu, Phe, Gly, His,
      Ile, Leu, Met, Asn, Pro, Gln, Arg, Ser, Thr, Val, Trp, Tyr
<220> FEATURE:
<221> NAME/KEY: variant
<222> LOCATION: (10)..(10)
<223> OTHER INFORMATION: Xaa can be Cys, Asp, Glu, Phe, Gly, His, Ile,
      Leu, Met, Asn, Pro, Gln, Arg, Ser, Thr, Val, Trp, Tyr
<220> FEATURE:
<221> NAME/KEY: variant
<222> LOCATION: (18)..(18)
<223> OTHER INFORMATION: Xaa can be any amino acid
<220> FEATURE:
<221> NAME/KEY: variant
<222> LOCATION: (20)..(20)
<223> OTHER INFORMATION: Xaa can be any amino acid
<220> FEATURE:
<221> NAME/KEY: variant
<222> LOCATION: (22)..(22)
<223> OTHER INFORMATION: Xaa can be any amino acid
<220> FEATURE:
<221> NAME/KEY: variant
<222> LOCATION: (25)..(25)
<223> OTHER INFORMATION: Xaa can be any amino acid
<220> FEATURE:
<221> NAME/KEY: variant
<222> LOCATION: (29)..(29)
<223> OTHER INFORMATION: Xaa can be any amino acid

<400> SEQUENCE: 17

Xaa Leu Pro Val Cys Gly Glu Xaa Cys Xaa Gly Gly Thr Cys Asn Thr
1               5                   10                  15

Pro Xaa Cys Xaa Cys Xaa Trp Pro Xaa Cys Thr Arg Xaa
            20                  25
```